(12) United States Patent
Wallberg et al.

(10) Patent No.: US 8,338,471 B2
(45) Date of Patent: *Dec. 25, 2012

(54) (2,5-DIOXOIMIDAZOLIDIN-1-YL)-N-HYDROXY-ACETAMIDES AS METALLOPROTEINASE INHIBITORS

(75) Inventors: Hans Wallberg, Huddinge (SE);
 Ming-Hua Xu, Shanghai (CN);
 Guo-Qiang Lin, Shanghai (CN);
 Xin-Sheng Lei, Lianyungang (CN);
 Piaoyang Sun, Lianyungang (CN);
 Kevin Parkes, Essex (GB); Tony Johnson, Essex (GB); Bertil Samuelsson, Huddinge (SE)

(73) Assignee: Medivir AB, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/222,883

(22) Filed: Aug. 31, 2011

(65) Prior Publication Data
US 2012/0015994 A1 Jan. 19, 2012

Related U.S. Application Data

(62) Division of application No. 12/097,192, filed as application No. PCT/EP2006/012019 on Dec. 13, 2006, now Pat. No. 8,022,092.

(30) Foreign Application Priority Data

Dec. 14, 2005 (EP) ..................................... 05112144

(51) Int. Cl.
 *A61K 31/4166* (2006.01)
 *C07D 233/02* (2006.01)
(52) U.S. Cl. ..................................... 514/401; 548/319.5
(58) Field of Classification Search ................. 548/319.5
 See application file for complete search history.

(56) References Cited

U.S. PATENT DOCUMENTS 6,462,063 B1 10/2002 Ho et al.
2003/0134827 A1 7/2003 Duan et al.
2005/0171096 A1 8/2005 Sheppeck et al.

FOREIGN PATENT DOCUMENTS

WO WO-02/28829 A2 4/2002

OTHER PUBLICATIONS

Whittaker, M., et al, Chem Rev, (1999), v. 99(9), pp. 2735-2776.
Whittaker, M., et al, Expert Opin Ther Patents, (2004), v. 14(11), pp. 1637-1640.
Vippagunta, et al., Advanced Drug Delivery Reviews, 48 (2001), pp. 3-26.
Document No. 136: 310184, CAPLUS, retrieved Jul. 28, 2010.

*Primary Examiner* — Shawquia Young
(74) *Attorney, Agent, or Firm* — Birch, Stewart, Kolasch & Birch, LLP

(57) ABSTRACT

The invention provides compounds of the formula (I)

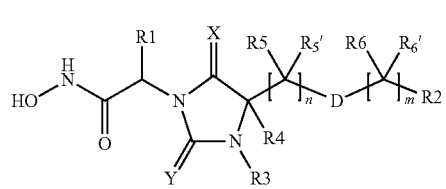

wherein the variables are as defined in the specification.

The compounds of the invention are inhibitors of metalloproteinase MMP-12 and are among other things useful for the treatment of obstructive airway diseases, such as chronic obstructive pulmonary disease (COPD).

9 Claims, No Drawings

(2,5-DIOXOIMIDAZOLIDIN-1-YL)-N-HYDROXY-ACETAMIDES AS METALLOPROTEINASE INHIBITORS

This application is a Divisional of co-pending application Ser. No. 12/097,192 filed on Mar. 24, 2009, and for which priority is claimed under 35 U.S.C. §120. Application Ser. No. 12/097,192 is the national phase of PCT International Application No. PCT/EP2006/012019 filed on Dec. 13, 2006 under 35 U.S.C. §371. This application also claims priority of Application No. 05112144.0 filed in Europe on Dec. 14, 2005 under 35 U.S.C. §119. The entire contents of each of which are hereby incorporated by reference.

TECHNICAL FIELD

This invention relates to novel compounds which are selective inhibitors of matrix metalloproteinases, especially metalloproteinase 12 (MMP-12), processes for their preparation, pharmaceutical compositions containing them and their use in therapy.

BACKGROUND TO THE INVENTION

Metalloproteinases represent a super family of proteinases (enzymes), whose numbers have increased dramatically in recent years. Based on structural and functional considerations, these enzymes have been classified into families and subfamilies N. M. Hooper, FEBS letters 354, 1-6 (1994). Examples of metalloproteinases include the matrix metalloproteinases (MMPs), which is a family of zinc containing endopeptidases, such as the collagens (MMP-1, MMP-8, MMP-13, MMP-18), the gelatinases (MMP-2, MMP-9), the stromelysins (MMP-3, MMP-10, MMP-11), matrilysin (MMP-7, MMP-26), metalloelastase (MMP-12) enamelysin (MMP-20), the MT-MMPs (MMP-14, MMP-15, MMP-16, MMP-17, MMP-24, MMP-25).

The MMPs is a family of zinc containing endopeptidases which are capable of cleaving large biomolecules like the collagens, proteoglycans and fibronectins, a process necessary for the growth and remodelling of tissues such as embryonic development and bone formation under normal physiological conditions. Expression is upregulated by pro-inflammatory cytokines and/or growth factors. The MMP's are secreted as inactive zymogens which, upon activation, are subject to control by endogenous inhibitors, for example, tissue inhibitor of metalloproteinases (TIMP) and α-macroglobulin. Chapman, K. T. et al., J. Med. Chem. 36, 4293-4301 (1993); Beckett, R. P. et al., DDT 1, 16-26 (1996). The characterizing feature of diseases involving the enzymes appears to be a stoichiometric imbalance between active enzymes and endogenous inhibitors, leading to excessive tissue disruption, and often degradation. McCachren, S. S., Arthritis Rheum. 34, 1085-1093 (1991).

Over-expression and activation of MMPs have been linked with a wide range of diseases such as cancer, tumour metastasis, rheumatoid arthritis, osteoarthritis, chronic inflammatory disorders such as emphysema, cardiovascular disorders such as atherosclerosis, corneal ulceration, dental diseases such as gingivitis and periodontal disease, and neurological disorders such as multiple sclerosis. Chirivi, R. G. S. et al., Int. J. Cancer, 58, 460-464 (1994); Zucker, S., Cancer Research, 53, 140-144 (1993). In addition, a recent study indicates that MMP-12 is required for the development of smoking-induced emphysema in mice. Science, 277, 2002 (1997). MMP-12, also known as macrophage elastase or metalloelastase, was initially cloned in the mouse by Shapiro et al., J. Biological Chemistry, 267, 4664 (1992) and in man by the same group in 1995. Structurally, the proMMP-12 consists of a pro-domain, a catalytic domain containing the zinc binding site and a C-terminal hemopexin-like domain. Recombinant human MMP-12 can be activated by autocatalysis as described below and reviewed by Shapiro et al "Macrophage Elastase" in Handbook of Proteolytic Enzymes 2004 (Eds A J Barrett et al) pp 540-544 Academic Press, San Diego.

MMP-12 is preferentially expressed in activated macrophages and its expression in monocytes can be induced by cytokines such as GM-CSF and CD-40 signalling. In addition to elastin, MMP-12 can degrade a broad spectrum of substrates, including type IV collagen, fibronectin, laminin, vitronectin, proteoglycans, chondroitin sulphate, myelin basic protein, alpha-one chymotrypsin and plasminogen. It can also activate MMP-2 and MMP-3. MMP-12 is required for macrophage mediated proteolysis and matrix invasion in mice. MMP-12 is proposed to have a direct role in the pathogenesis of aortic aneurisms and in the development of pulmonary emphysema that results from chronic inhalation of cigarette smoke, wood smoke and urban smogs.

MMP-12 has been shown to be secreted from alveolar macrophages from smokers Shapiro et al., J. Biological Chemistry, 268, 23824, (1993) as well as in foam cells in atherosclerotic lesions Matsumoto et al., Am. J. Pathol, 153, 109, (1998). A mouse model of COPD is based on challenge of mice with cigarette smoke for six months, two cigarettes a day six days a week. Wildtype mice developed pulmonary emphysema after this treatment. When MMP-12 knock-out mice were tested in this model they developed no significant emphysema, strongly indicating that MMP-12 is a key enzyme in the COPD pathogenesis. The role of MMPs such as MMP-12 in COPD (emphysema and bronchitis) is discussed in Anderson and Shinagawa, Current Opinion in Anti-inflammatory and Immunomodulatory Investigational Drugs: 29-38 (1999). It was recently discovered that smoking increases macrophage infiltration and macrophage-derived MMP-12 expression in human carotid artery plaques Kangavari (Matetzky S, Fishbein M C et al., Circulation 102, (18), 36-39 Suppl. S, October 31, (2000).

Apart from the role of these potentially very destructive enzymes in pathology, the MMPs play an essential role in cell regrowth and turnover in healthy tissue. Broad spectrum inhibition of the MMPs in the clinical setting results in musculoskeletal stiffness and pain. H. S. Rasmussen and P. P. McCann, Pharmacol. Ther., 75, 69-75 (1997). This side effect and others associated with broad spectrum inhibition may be enhanced in chronic administration. Thus, it would be advantageous to provide selective MMP inhibitors.

The inhibition of such MMP-12 activities is considered to contribute to the improvement and prevention of the above discussed diseases caused by or related to the activity of MMP-12. Therefore, the development of MMP-12 inhibitors has been desired.

A number of metalloproteinase inhibitors are known and described in the literature, (see for example the reviews of MMP inhibitors by Beckett R. P. and Whittaker M., 1998, Exp. Opin. Ther. Patents, 8 (3):259-282.

Whittaker M. et al, 1999, Chemical Reviews 99 (9): 2735-2776) review a wide range of known MMP inhibitor compounds. They state that an effective MMP inhibitor requires a zinc binding group, i.e. a functional group capable of chelating the active site zinc(II) ion, at least one functional group which provides a hydrogen bond interaction with the enzyme backbone, and one or more side chain which undergo effective van der Waals interactions with the enzyme subsites. Zinc binding groups in known MMP inhibitors include carboxylic acid groups, hydroxamic acid groups, sulfhydryl groups or mercapto groups.

Despite the potent affinity of hydroxamic acid as zinc coordinator, hydroxamic acid inhibitors demonstrate a considerable degree of specificity within the MMP family: a potent inhibitor of one member of the MMP family, may have only minimal potency against another MMP family member. This exhibited specificity typically relies on the identity of the other parts of the inhibitors, e.g. the P1, P2, P3 and P4 units. Without in any way wishing to be bound by theory, or the ascription of tentative binding modes for specific variables, the notional concepts P1, P2, P3 and P4 are used herein for convenience only and have substantially their conventional meanings, as illustrated by Schechter & Berger, (1976) Biochem Biophys Res Comm 27 157-162, and denote those portions of the inhibitor believed to fill the S1, S2, S3 and S4 subsites respectively of the enzyme, where S1 is adjacent the cleavage site and S4 remote from the cleavage site.

There are several patents which disclose hydroxamate-based inhibitors of metalloproteases or analogous enzymes.

WO02/028829 describes inhibitors of peptide deformylase (PDF) useful for example in the development of new antibacterial drugs. PDF is a bacterial enzyme which shares several structural features in common with zinc metalloproteases. PDF does not cleave a peptide bond, but rather cleaves off the N-formyl group from the terminal N-formyl methionine which characterises the nascent bacterial polypeptide chain. Despite the fact that the compounds of WO02/028829 comprise a hydroxamic acid group the SAR (structure activity relationship) exhibited by these inhibitors is not helpful to the design of specific inhibitors of the endopeptidase MMP-12. An endopeptidase cleaves within a peptide chain, and therefore the protease typically recognises a number of amino acid residues around the intended cleavage site. In contrast PDF is intended to cleave a terminal group on the first amino acid of bacterial proteins of very different sequence. Accordingly the selectivity of PDF is predicated on recognition of the N-formyl.methionine terminal residue rather than the identity of the adjacent amino acids.

US 3003/0134827 discloses compounds having a hydroxyacetamide moiety linked to a broad range of cyclic amides as inhibitors of MMPs in particular MMP-3, aggrecanase and TNF-α-converting enzyme (TACE). Although hydantoin is postulated as one of many such cyclic amides, US 2003/0134827 discloses no concrete examples of compounds within the scope of this invention. As demonstrated in the following biological examples, the compounds of the invention achieve potent MMP-12 inhibition while at the same time being highly selective against the enzymes addressed in US 2003/0134827.

U.S. Pat. No. 6,462,063 discloses substituted hydantoin hydroxamates capable of inhibiting C-proteinase. In contrast to the compounds of the invention defined below, the compounds of U.S. Pat. No. 6,462,063 have a hydroxamic acid linked to a carbon atom of the hydantoin ring via a chain comprising, apart from the acid function, at least three atoms. By varying the length of the hydroxamic acid carrying chain and the substitution pattern of the hydantoin ring, the binding properties to the enzyme and hence the specificity of the inhibitor will be altered. The hydroxamate function of U.S. Pat. No. 6,462,063 is thus sitting on the other side of the hydantoin ring compared to the compounds of the invention defined below and is also disposed further out from the hydantoin These kind of structural variations between the class of compounds disclosed in U.S. Pat. No. 6,462,063 and inhibitors based on hydantoin hydroxamates wherein the hydroxamic acid is linked to a nitrogen atom of a hydantoin group via a one atom chain, will render the SAR exhibited by the compounds of U.S. Pat. No. 6,462,063 of no relevance to the design of specific inhibitors of MMP-12

WO02/074750 discloses a new class of compounds that act as MMP inhibitors wherein the zinc binding group of the inhibitor is constituted of a five membered ring structure such as a hydantoin group. The zinc binding ring structure is attached to one or more functional groups or side chains which are disposed at an appropriate angle and distance to recognise the characteristic sequence around the appropriate MMP12 cleavage site. The mode of binding to the enzyme of this class of zinc-binding inhibitors will thus differ substantially from that of compounds having other zinc binding groups, such as hydroxamic acid adjacent a hydantoin core, in that coordination of the hydroxamate zinc binding group will displace the hydantoin away from the structural zinc. Any further substituents opposed from the hydroxamate will also be displaced away from the structural zinc and will interact with other parts of the enzyme. Due to this different binding mode of the compounds disclosed in WO02/074750 compared to hydantoin hydroxamates, the SAR found for the P1, P2, P3 and P4 units of the compounds of WO02/074750 is not relevant to the design of new MMP inhibitors based on a hydantoin hydroxamate scaffold.

Similarly, US 2005/0171096 discloses hydantoin derivatives alleged to be inhibitors of matrix metalloproteinases and TACE although no guidance as to the specificity of the inhibitors is given. The compounds of US 2005/0171096 do not bear a hydroxamic acid or conventional zinc-binding group. This suggests that that the hydantoin is the zinc binding group and hence the SAR exhibited by the P1, P2 and P3 units of these compounds is different from that of an inhibitor based on a hydantoin substituted with a hydroxamic acid carrying side chain.

As foreshadowed above, we have now discovered a particular configuration of hydroxamic hydantoins that are inhibitors of metalloproteinases and are of particular interest in selectively inhibiting MMPs such as MMP-12 and have desirable activity profiles. The compounds of this invention have beneficial potency, selectivity and/or pharmacokinetic properties.

DISCLOSURE OF THE INVENTION

In accordance with the present invention, there is provided a compound of formula (I) or a pharmaceutically acceptable salt or solvate thereof:

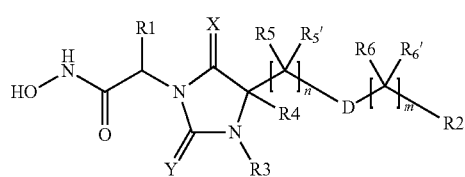

wherein;
$R^1$ is $C_1$-$C_6$alkyl, $C_0$-$C_3$alkandiylcarbocyclyl, $C_0$-$C_3$alkandiylheterocyclyl,
$R^2$ is carbocyclyl or heterocyclyl;
$R^3$ is H or $C_1$-$C_4$alkyl;
$R^4$ is H or $C_1$-$C_4$alkyl;
each $R^5$ and $R^{5'}$ is independently H, $C_1$-$C_4$alkyl or halo; or
$R^4$ and an adjacent $R^{5'}$ together define a double bond;

each $R^6$ and $R^{6'}$ is independently H, $C_1$-$C_4$alkyl or halo; or $R^5$ and an adjacent $R^6$ together define a double bond; or $R^5$, $R^{5'}$ and an adjacent $R^6$ and $R^{6'}$ together define a triple bond;

n is 1-3, m is 0-3;

D is absent, or D is an ether, thioether, amine, amide, carbamate, urea or sulphonamide linkage; whereby the group $(CR^5R^{5'})_n$-D-$(CR^6R^{6'})_m$ has at least 2 chain atoms;

X and Y are independently O or S;

and wherein each $C_1$-$C_4$alkyl is optionally substituted with 1 to 3 halo or an hydroxyl;

each $C_1$-$C_6$alkyl, carbocyclyl or heterocyclyl (including those in any $C_0$-$C_3$alkanediylcarbocyclyl or $C_0$-$C_3$alkanediylheterocyclyl group) is independently optionally substituted with 1 to 3 substituents selected from halo, oxo, cyano, azido, nitro, $C_1$-$C_6$alkyl, $C_0$-$C_3$Alkdiylcarbocyclyl, $C_0$-$C_3$Alkdiylheterocyclyl, Z—NRaRb, Z—O—Rb, Z—S—Rb, Z—C(=NOH)Rb, Z—C(=O)Rb, Z—(C=O)NRaRb, Z—NRaC(=O)Rb, Z—NRaSO$_p$Rb, Z—S(=O)$_p$Rb, Z—S(=O)$_p$ NRaRb, Z—C(=O)ORb, Z—OC(=O)Rb, Z—NRaC(=O)ORb or Z—OC(=O)NRaRb; wherein;

each $C_0$-$C_3$Alkdiyl is independently a bond, a $C_1$-$C_3$ straight or branched, saturated carbon chain or a $C_2$-$C_3$ straight or branched unsaturated carbon chain; the carbocyclyl or heterocyclyl moiety of any $C_0$-$C_3$Alkdiylcarbocyclyl, $C_0$-$C_3$Alkdiylheterocyclyl is optionally substituted 1 to 3 times with substituents selected from halo, oxo, cyano, azido, nitro, $C_1$-$C_4$alkyl, Z—NRaRc, Z—O—Rc, Z—S—Rc, Z—C(=O)Rc, Z—(C=O)NRaRc, Z—NRaC(=O)Rc, Z—NRaSO$_p$Rc, Z—S(=O)$_p$Rc, Z—S(=O)$_p$NRaRc, Z—C(=O)ORc, Z—OC(=O)Rc, Z—NRaC(=O)ORc or Z—OC(=O)NRaRc;

each Z is independently a bond or $C_1$-$C_3$alkanediyl;

each Ra is independently H or $C_1$-$C_4$alkyl;

each Rb is independently H or $C_1$-$C_6$alkyl, $C_0$-$C_3$Alkdiylcarbocyclyl, $C_0$-$C_3$Alkdiylheterocyclyl;

or Ra and Rb together with an adjacent N atom define pyrrolidine, piperidine, morpholine, piperazine or N-methyl piperazine;

Rc is H or $C_1$-$C_4$alkyl;

or Rc and Ra together with an adjacent N atom define pyrrolidine, piperidine, morpholine, piperazine or N-methyl piperazine each p is independently 1 or 2;

and pharmaceutically acceptable salts and solvates thereof.

In one embodiment of the invention the $R^1$ group comprises an optionally substituted alkyl chain, especially branched $C_2$-$C_6$alkyl chains. Preferably the branch occurs at position 1, adjacent the backbone of the inhibitor, as shown in the partial structure:

where R1' is $CH_3$, $CH_2CH_3$, $C_1$haloalkyl, halo, hydroxy; R1" is H, $CH_3$, $CH_2CH_3$, $C_1$haloalkyl, halo, hydroxyl;

$R^{1*}$ is $C_1$-$C_5$ optionally substituted alkyl, for example substituted with 1-3 substituents independently selected from carbocyclyl, heterocyclyl, ZNRaRb, nitro, hydroxyl, cyano, carboxy, oxo, halo, $C_1$-haloalkyl, $C_1$-$C_4$alkyl, $C_1$-$C_4$alkoxy, $C_1$-$C_4$alkanoyl or carbamoyl groups.

Representative values of $R^1$ thus include 1-methylpropyl, 1,1-dimethylpropyl, 1-ethyl-1-methylpropyl, 1,1dimethylbutyl, 1,1-diethylpropyl, 1-ethylpropyl, 1-methylbutyl, 1,2-dimethylpropyl. Currently preferred values of $R^1$ include i-propyl, sec.butyl and tert.butyl.

A moiety such as an optionally substituted carbocyclyl or an optionally substituted heterocyclyl distanced 1-5 atoms from the backbone of the inhibitor at the position of $R^1$ can be used to alter the lipophilicity of the compounds of the invention. It is believed that an appropriate choice of this moiety will confer any lipophilic/hydrophilic characteristics to the inhibitors required to improve certain properties, i.a. their DMPK properties.

Accordingly, suitable values for $R^{1*}$ are $C_1$-$C_5$alkyl substituted with carbocyclyl or $C_1$-$C_5$alkyl substituted with heterocyclyl wherein said carbocyclyl and heterocyclyl are optionally substituted 1-4 times with substituents selected from $C_1$-$C_3$alkyl, oxo and halo. Preferred structures for $R^1$ thus include:

wherein n is 0, 2, 3 or 4.

In other embodiments of the invention, the $C_0$-$C_3$alkandiylcarbocyclyl as $R^1$ has methylene as the $C_0$-$C_3$alkandiyl component and a $C_5$ or $C_6$ monocyclic ring as the carbocyclyl component. Representative values of $R^1$ in this embodiment thus include (optionally substituted): benzyl, cyclohexylmethyl-, 1-methylcyclohexylmethyl-, cyclopentylmethyl-, 1-methylcyclopentylmethyl, where the optional substituents are as outlined above.

In a preferred embodiment of the invention, the $C_0$-$C_3$alkandiylcarbocyclyl as $R^1$ has a bond as the $C_0$-$C_3$alkandiyl component and a $C_5$ or $C_6$ monocyclic ring as the carbocyclyl component. Representative values of $R^1$ in this embodiment thus include (optionally substituted): phenyl, or preferably cyclohexyl or cyclopentyl, where the optional substituents are as outlined above.

In other embodiments of the invention, the $C_0$-$C_3$alkandiylheterocyclyl as $R^1$ has methylene as the $C_0$-$C_3$alkandiyl component and a 5 or 6 membered aromatic, partially saturated, or unsaturated monocyclic ring as the heterocyclyl component. Representative values of $R^1$ in this embodiment thus include (optionally substituted): pyrrolylmethyl-, pyrrolinylmethyl-, pyrrolidinylmethyl-, thiazolylmethyl, pyridylmethyl-, pyrimidinylmethyl-, piperidylmethyl-, piperazinylmethyl- or morpholinylmethyl, where the optional substituents are as outlined above.

In other embodiments of the invention, the $C_0$-$C_3$alkandiylheterocyclyl as $R^1$ has a bond as the $C_0$-$C_3$alkandiyl component and a 5 or 6 membered aromatic, partially saturated, or unsaturated monocyclic ring as the heterocyclyl component. Representative values of $R^1$ in this embodiment thus include (optionally substituted): pyrrolyl, pyrrolinyl, pyrrolidinyl, thiazolyl, pyridyl, pyrimidinyl, piperidyl-, piperazinyl or morpholinyl; where the optional substituents are as outlined above.

In typical embodiments of the invention the chiral center to which the $R^1$ group is attached has the R stereochemistry as shown in the partial structure:

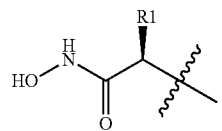

This stereochemistry corresponds to a D-amino acid, which is unexpected in the context of an inhibitor of an enzyme such as a protease. Such enzymes cleave proteins which are universally composed of L-amino acids. The recognition sites of most proteases thus prefer L-configurations. The compounds of the invention may be administered as the racemate at $R^1$, but are preferably administered as pure or substantially enantiomerically pure preparations, such as at least 90% ee at $R^1$, preferably at least 95%, such as >97% ee.

In some embodiments of the invention both of X and Y are =S or one of X and Y is =S and the other is =O, especially wherein X is =O. It is currently preferred that both X and Y are =O.

In typical embodiments of the invention, the steric center of the imidazoline ring to which the —$(CR^5R^{5'})_n$-D-$(CR^6R^{6'})_m$—$R^2$ group is attached has the S stereochemistry, as depicted in the partial structure:

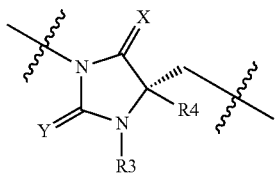

The compounds of the invention may be administered as the racemate at this position, but are preferably administered as pure or substantially enantiomerically pure preparations, such as at least 90% ee at this position, preferably at least 95%, such as >97% ee.

In other embodiments of the invention, $R^4$ and an adjacent $R^5$ together define an olefinic bond forming part of the linkage to $R^2$:

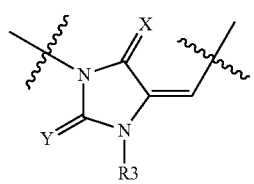

In this embodiment, D will typically be absent, m will be 1 or 2 and each $R^6$/$R^{6'}$ is H.

It is currently preferred that the stereochemistry at the chiral center to which $R^1$ is attached and at the chiral center to which the —$(CR^5R^{5'})_n$-D-$(CR^6R^{6'})_m$—$R^2$ group is attached have the R and S stereochemistries respectively.

Representative values of D include S, NH, NMe, NH(C=O)C(=O)NH, NH(=O)NH, NH(C=O)O and OC(=O)NH.

Currently preferred values for D include O, i.e. an ether linkage or D is absent (i.e. the $(CR^5R^{5'})_n$-D-$(CR^6R^{6'})_m$ function is a $C_1$-$C_6$alkandiyl chain.

Conveniently the —$(CR^5R^{5'})_n$-D-$(CR^6R^{6'})_m$— group has in total 2 or 3 chain atoms, especially:
—$CH_2CH_2$— (2), —$CH_2CH_2CH_2$— (3),
—$CH_2O$— (2), —$CH_2OCH_2$— (3), —$CH_2CH_2O$— (3),
—$CH_2$—NH— (2), —$CH_2CH_2NH$— (2),
—$CH_2OC(=O)NH$— (4), —$CH_2NH(C=O)O$— (4).

The numbers in brackets after each —$(CR^5R^{5'})_n$-D-$(CR^6R^{6'})_m$ group indicate the number of chain atoms.

It is currently preferred that n and m are each 1 and D is absent, i.e. the —$(CR^5R^{5'})_n$-D-$(CR^6R^{6'})_m$— group is —$CH_2CH_2$—.

In some embodiments of the invention each $R^5$, $R^{5'}$ and each $R^6$, $R^{6'}$ (if present) are H, but the invention extends to branched or substituted structures, such as those wherein $R^5$ and/or $R^{5'}$ on any one carbon atom is, for example methyl, i-propyl, t-butyl or fluoro. To avoid asymmetric centers it can be advantageous that both $R^5$ and $R^{5'}$ and/or $R^6$ and $R^{6'}$ on any one carbon atom are the same, typically, H, F or Me.

In some embodiments of the invention, D is absent and adjacent $R^5$ and $R^6$ together define a cis or trans double bond:

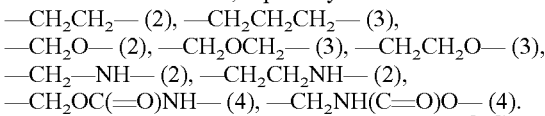

In this embodiment n and m are typically 1 and the adjacent $R^{5'}$ and $R^{6'}$ are H. In the event that n or m is >1 the $R^5$, $R^{5'}$ $R^6$ and $R^{6'}$ of any such further chain atoms are generally H.

In other embodiments of the invention, D is absent and adjacent $R^5$, $R^{5'}$ $R^6$ and $R^{6'}$ together define a triple bond:

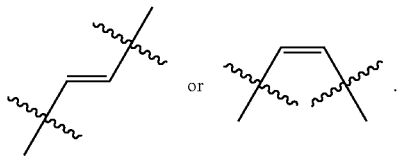

In one embodiment of the invention $R^2$ as carbocyclyl is an optionally substituted aromatic ring structure, such as naphthyl or indanyl and especially phenyl.

In another embodiment of the invention $R^2$ as heterocyclyl is an optionally substituted, aromatic ring structure, such as a monocyclic ring selected from pyrrole, furan, thiophene, pyrazole, pyrazoline, imidazole, oxazole, isooxazole, thiazole, isothiazole, triazole, oxadiazole, furazan, thiadiazole, tetrazole, pyridine, pyridazine, pyrimidine, pyrazine, thiazine, triazine; or a bicyclic ring selected from thienobifuran, indole, isoindole, benzofuran, isobenzofuran, indoline, isoindoline, benzothiophene, isobenzothiophene, indazole, benzimidazole, benzthiazole, purine, quinoline, isoquinoline, chromane, isochromane, cinnolene, quinazoline, quinoxaline, napthyridine, phthalazine or pteridine.

It is currently preferred that $R^2$ is an optionally substituted, aromatic monocyclic ring, especially optionally substituted: pyrrolyl, thiazolyl, pyridyl or pyrimidinyl, and particularly optionally substituted phenyl.

In some embodiments an optional substituent to $R^2$ is located at the para, ortho or meta position relative to the —$(CR^5R^{5'})_n$-D-$(CR^6R^6)_m$— linkage. Typical such substituents include $C_1$-$C_4$alkyl, such as methyl, halo$C_1$-$C_2$alkyl, such as fluoromethyl and trifluoromethyl, —O$C_1$-$C_4$alkyl, such as methoxy, —C(=O)$C_1$-$C_4$alkyl, such as acetyl, or halo, such as fluoro. A preferred structure for $R^2$ is phenyl substituted with fluoro in the ortho position which phenyl is optionally further substituted in the meta or preferably para position.

In some embodiments an optional substituent to $R^2$ is in the para position relative to the —$(CR^5R^{5'}_n$-D-$(CR^6R^{6'})_m$— linkage and comprises an aromatic, monocyclic ring such as those defined above for $R^2$, especially optionally substituted: phenyl, pyrrolyl, thiazolyl, pyridyl or pyrimidinyl. This optional substituent is typically bonded directly to the $R^2$ ring or via a methylene, ethylene or ether linkage; as shown below

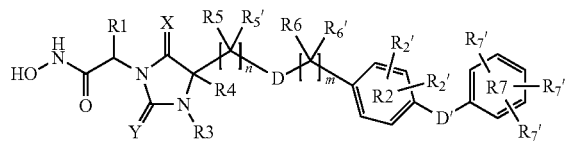

II

In the structure II, the $R^2$ ring has been depicted for the purposes of illustration only as phenyl, but other ring systems will be equally applicable. It will be seen that the ring $R^2$ has one, but may also have two additional substituents $R^{2'}$ which is the ortho or meta substituent described in the immediately preceding paragraph.

Where $R^2$ is a 5-membered ring, the ring substituent of this aspect of the invention will, of course not be at the para position, but rather at a corresponding position disposed distally from the —$(CR^5R^{5'})_n$-D-$(CR^6R^{6'}H_2)_m$— linkage.

In structure II, the ring substituent of this aspect of the invention is depicted as $R^7$ and has been illustrated for the purposes of illustration only as phenyl, but other heteroaromatic monocyclic ring systems will also be applicable. Typical $R^7$ rings include phenyl, pyrrolyl, thiazolyl, pyridyl or pyrimidinyl. As elaborated below, the ring $R^7$ and its linkage D' constitutes a value for $C_0$-$C_3$Alkdiylcarbocyclyl, $C_0$-$C_3$Alkdiylheterocyclyl or —Z—ORb, where Rb is $C_0$-$C_3$Alkdiylcarbocyclyl, $C_0$-$C_3$Alkdiylheterocyclyl. Ring $R^7$ is thus optionally substituted with 1 to 3 substituents selected from halo, oxo, cyano, azido, nitro, $C_1$-$C_4$alkyl, Z—NRaRc, Z—O-Rc, Z—S—Rc, Z—C(=O)Rc, Z—(C=O)NRaRc, Z—NRaC(=O)Rc, Z—NRaSO$_p$Rc, Z—S(=O)$_p$Rc, Z—S(=O)$_p$NRaRc, Z—C(=O)ORc, Z—OC(=O)Rc, Z—NRaC(=O)ORc or Z—OC(=O)NRaRc.

Representative substituents for ring $R^7$ include, for example one or two substituents selected from $C_1$-$C_4$alkyl, such as methyl, halo$C_1$-$C_2$alkyl, such as fluoromethyl and trifluoromethyl, —O$C_1$-$C_3$alkyl, such as methoxy, —C(=O)$C_1$-$C_3$alkyl, such as acetyl, or halo, such as fluoro.

The linkage to ring $R^7$ is marked D' in structure II and typically comprises a bond, methylene or ethylene linkage (i.e. $R^7$ is $C_0$-$C_3$Alkdiylcarbocyclyl or $C_0$-$C_3$Alkdiylheterocyclyl as a substituent to $R^2$) or an ether linkage (i.e. $R^7$ is Z—O—Rb, where Z is a bond or methylene, O is the ether linkage and Rb is $C_0$-$C_3$Alkdiylcarbocyclyl or $C_0$-$C_3$Alkdiylheterocyclyl).

Further preferred structures for the linkage D' include C(=O)CH$_2$ and CH$_2$C(=O).

Unless otherwise defined, the scientific and technological terms and nomenclature used in the foregoing and hereinafter have the same meaning as commonly understood by a person of ordinary skill to which this invention pertains, in addition, the following definitions apply unless otherwise noted.

'$C_1$-$C_6$alkyl' (occasionally abbreviated to $C_1$-$C_6$alk and also used in compound expressions such as $C_1$-$C_6$alkyloxy etc) as applied herein is meant to include straight and branched aliphatic carbon chain substituents containing from 1 to 6 carbon atoms, such as methyl, ethyl, n-propyl, isopropyl, n-butyl, isobutyl, t-butyl, pentyl, isopentyl, hexyl and any simple isomers thereof. Me denotes a methyl group.

'$C_1$-$C_4$alkyl' (occasionally abbreviated to $C_1$-$C_4$alk, and used in composite expressions) as applied herein is meant to include methyl, ethyl, propyl, isopropyl, cyclopropyl, butyl, 1-methyl-cyclopropyl.

'$C_0$-$C_3$alkanediyl' as applied herein is meant to include a bond ($C_0$) bivalent straight and branched saturated carbon chains such as methylene, ethanediyl, 1,3-propanediyl and 1,2-propanediyl.

'$C_0$-$C_3$Alkdiyl' as applied herein is meant to include a bond ($C_0$), bivalent $C_1$-$C_3$ straight and branched saturated carbon chains such as methylene, ethanediyl, 1,3-propanediyl and 1,2-propanediyl, or $C_2$-$C_3$ straight and branched unsaturated carbon chains such as ethenediyl, ethynediyl, 1,3-propenediyl and 1,2-propenediyl and propynediyl.

'$C_0$-$C_3$alkanediyl-O—$C_1$-$C_4$alkyl' (occasionally abbreviated to $C_0$-$C_3$alk-O—$C_1$-$C_4$alk) as applied herein is meant to include $C_1$-$C_4$alkoxy groups such as methoxy, ethoxy, n-propoxy, isopropoxy directly bonded (i.e. $C_0$) or through an intermediate methylene, ethanediyl, 1,3-propanediyl or 1,2-propanediyl chain.

'amide linkage' as applied herein is meant to include —NRfC(=O)— and —C(=O)NRf— wherein Rf is $C_1$-$C_4$alkyl such as Me, or preferably H.

'amine linkage' as applied herein is meant to include —NH— or —NRe—, where Re is $C_1$-$C_4$alkyl or C(=O)$C_1$-$C_4$alkyl.

'carbamate linkage' as applied herein is meant to include —OC(C=O)NRf— and —NRfC(=O)O—, wherein Rf is $C_1$-$C_4$alkyl such as Me, or preferably H.

'sulphonamide linkage' as applied herein is meant to include —NRfS(=O)$_2$— and —S(=O)$_2$NRf— wherein Rf is $C_1$-$C_4$alkyl such as Me, or preferably H.

'Amino' is meant to include NH$_2$, and mono- and dialkylamino such as NHC$_1$-$C_6$alkyl and N(C$_1$-$C_6$alkyl)$_2$ groups especially NHC$_1$-$C_3$alkyl and N(C$_1$-$C_3$alkyl)$_2$, or the two alkyl groups of dialkylamino together form a saturated cyclic amine such as pyrrolidinyl, piperidinyl, piperazinyl, N-methylpiperazinyl and morpholinyl.

'Amido' is meant to include NHC(=O)$C_1$-$C_6$alkyl, NC$_1$-$C_6$alkylC(=O)$C_1$-$C_6$alkyl.

'Carbamoyl' is meant to include C(=O)NH$_2$, and mono- and dialkylcarbamoyl, such as C(=O)NHC$_1$-$C_6$alkyl and C(=O)N(C$_1$-$C_6$alkyl)$_2$, especially C(=O)NHC$_1$-$C_3$alkyl and C(=O)N(C$_1$-$C_3$alkyl)$_2$, or the two $C_1$-$C_6$alkyl groups of the dialkylcarbamoyl together form a saturated cyclic amine such as pyrrolidinyl, piperidinyl, piperazinyl and morpholniyl.

'Halo' or halogen as applied herein is meant to include F, Cl, Br, I, particularly chloro and preferably fluoro.

Haloalkyl as applied herein means an alkyl in which 1-3 hydrogen atoms per carbon have been replaced with halo, preferably fluoro. Representative examples include difluoromethyl and 2,2-difluoroethyl, 2,2,2-trifluoroethyl and 2-fluoroethyl. Preferred examples include trifluoromethyl and fluoromethyl.

'$C_0$-$C_3$alkanediylaryl' as applied herein is meant to include a phenyl, naphthyl or phenyl fused to $C_3$-$C_7$cycloalkyl such as indanyl, which aryl is directly bonded (i.e. $C_0$) or through an intermediate methylene, ethanediyl, 1,3-propanediyl or 1,2-propanediyl group as defined for $C_0$-$C_3$alkaneyl above. Unless otherwise indicated the aryl and/or its fused cycloalkyl moiety is optionally substituted with 1-3 substituents selected from halo, hydroxy, nitro, cyano, carboxy, $C_1$-$C_6$alkyl, $C_1$-$C_4$alkoxy, $C_0$-$C_3$alkanediyl$C_1$-$C_4$alkoxy, $C_1$-$C_4$alkanoyl, amino, amido, carbamoyl, azido, oxo, mercapto, $C_0$-$C_3$alkanediylcarbocyclyl, $C_0$-$C_3$alkanediylheterocyclyl, it being understood that when the substituent is $C_0$-$C_3$alkanediylcarbocyclyl or $C_0$-$C_3$alkanediylheterocyclyl said carbocyclyl or heterocyclyl is typically not further substituted with $C_0$-$C_3$alkanediylcarbocyclyl or $C_0$-$C_3$alkanediylheterocyclyl. "Aryl" has the corresponding meaning, i.e. where the $C_0$-$C_3$alkanediyl linkage is absent.

'$C_0$-$C_3$alkanediylcarbocyclyl' as applied herein is meant to include $C_0$-$C_3$alkanediylaryl and $C_0$-$C_3$alkanediyl$C_3$-$C_7$cycloalkyl, and $C_0$-$C_3$alkanediyl$C_3$-$C_7$cycloalkyl further comprising an additional fused $C_3$-$C_7$cycloalkyl ring. Unless otherwise indicated the aryl or cycloalkyl group is optionally substituted with 1-3 substituents selected from halo, hydroxy, nitro, cyano, carboxy, $C_1$-$C_6$alkyl, $C_1$-$C_4$alkoxy, $C_0$-$C_3$alkanediyl$C_1$-$C_4$alkoxy, $C_1$-$C_4$alkanoyl, amino, amido, carbamoyl, azido, oxo, mercapto, $C_0$-$C_3$alkanediylcarbocyclyl and $C_0$-$C_3$alkanediylheterocyclyl, it being understood that when the substituent is $C_0$-$C_3$alkanediylcarbocyclyl or $C_0$-$C_3$alkanediylheterocyclyl said carbocyclyl or heterocyclyl is typically not further substituted with $C_0$-$C_3$alkanediylcarbocyclyl or $C_0$-$C_3$alkanediylheterocyclyl. "Carbocyclyl" has the corresponding meaning, i.e. where the $C_0$-$C_3$alkanediyl linkage is absent.

'$C_0$-$C_3$alkanediylheterocycylyl' as applied herein is meant to include a mono- or bicyclic, saturated or unsaturated, heteroatom-containing ring system, bonded directly i.e. ($C_0$), or through an intermediate methylene, ethanediyl, 1,3-propanediyl, or 1,2-propanediyl group as defined for $C_0$-$C_3$alkanediyl above. The ring system is derived by abstraction of a hydrogen from a monocyclic heteroatom containing ring such as pyrrole, furan, pyrroline, pyrrolidine, tetrahydrofuran, thiophene, tetrahydrothiophene, pyrrazole, imidazole, oxazole, isoxazole, pyrazoline, imidazoline, pyrazolidine, imidazolidine, dioxolane, thiazole, isothiazole, thiazolidine, isoxazolidine, 1,2,3-triazole, 1,2,4-triazole, 1,2,3-oxadiazole, furazan, thiadiazole, tetrazole, pyridine, pyran, dihydropyran, piperidine, pyridazine, pyrimidine, pyrazine, piperazine, morpholine, dioxane, thiazine, thiomorpholine, or from a saturated or unsaturated, heteroatom-containing bicyclic ring system such as pyrrolizine, thienofurane, indole, isoindole, benzofuran, isobenzofuran, indoline, isoindoline, benzothiophene, isobenzothiophene, indazole, benzimidazole, benzthiazole, purine, quinoline, isoquinoline, 4H-quinolizine, chromene, chromane, isochromane, cinnoline, quinazoline, quinoxaline, naphtyridine, phtalazine, pteridine etc. Any such non-saturated ring system having an aromatic character may be referred to as heteroaryl herein. Unless otherwise indicated the hetero ring system is optionally substituted with 1-3 substituents selected from halo, hydroxy, nitro, cyano, carboxy, $C_1$-$C_6$alkyl, $C_1$-$C_4$alkoxy, $C_0$-$C_3$alkanediyl$C_1$-$C_4$alkoxy, $C_1$-$C_4$alkanoyl, amino, amido, carbamoyl, azido, oxo, mercapto, $C_0$-$C_3$alkanediylcarbocyclyl, $C_0$-$C_3$alkanediylheterocyclyl, it being understood that when the substituent is $C_0$-$C_3$alkanediylcarbocyclyl or $C_0$-$C_3$alkanediylheterocyclyl said carbocyclyl or heterocyclyl is typically not further substituted with $C_0$-$C_3$alkanediylcarbocyclyl or $C_0$-$C_3$alkanediylheterocyclyl. "Heterocyclyl" and "Heteroaryl" has the corresponding meaning, i.e. where the $C_0$-$C_3$alkanediyl linkage is absent.

Typically the terms 'optionally substituted $C_0$-$C_3$alkanediylcarbocyclyl' and 'optionally substituted $C_0$-$C_3$alkanediylheterocyclyl' refers preferably to substitution of the carbocyclic or heterocyclic ring.

Typically heterocyclyl and carbocyclyl groups are thus a monocyclic ring with 5 or especially 6 ring atoms, or a bicyclic ring structure comprising a 6 membered ring fused to a 4, 5 or 6 membered ring.

Typical such groups include $C_3$-$C_8$cycloalkyl, phenyl, benzyl, tetrahydronaphthyl, indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be optionally substituted as defined herein.

The saturated heterocycle thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione, whereas the unsaturated heterocycle include radicals with an aromatic character such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl or carbocyclyl ring to form a bicyclic ring system.

It should be noted that the radical positions on any molecular moiety used in the definitions may be anywhere on such a moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

The invention relates to the compounds of formula (I) per se, the prodrugs, N-oxides, addition salts, quaternary amines, metal complexes, and stereochemically isomeric forms thereof.

The invention further relates to methods for the preparation of the compounds of formula (I), the prodrugs, N-oxides, addition salts, quaternary amines, metal complexes, and stereochemically isomeric forms thereof, its intermediates, and the use of the intermediates in the preparation of the compounds of formula (I).

It will be appreciated that the compounds according to the invention may contain one or more asymmetrically substituted carbon atoms. The presence of one or more of these asymmetric centres (chiral centres) in compounds according to the invention can give rise to stereoisomers, and in each case the invention is to be understood to extend to all such stereoisomers, including enantiomers and diastereomers, and mixtures including racemic mixtures thereof. Racemates may be separated into individual optically active forms using known procedures (cf. Advanced Organic Chemistry: 3rd Edition: author J March, pp 104-107) including for example the formation of diastereomeric derivatives having convenient optically active auxiliary species followed by separation and then cleavage of the auxiliary species.

Where optically active centres exist in the compounds of the invention, we disclose all individual optically active forms and combinations of these as individual specific embodiments of the invention, as well as their corresponding racemates.

Where tautomers exist in the compounds of the invention, we disclose all individual tautomeric forms and combinations of these as individual specific embodiments of the invention. The compounds of the invention may be provided as pharmaceutically acceptable salts, solvates, prodrugs, N-oxides, quaternary amines, metal complexes, or stereochemically isomeric forms. These include acid addition salts such as hydrochloride, hydrobromide, citrate, tosylate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine. Examples of solvates include hydrates.

The compounds of formula (I) have activity as pharmaceuticals. As previously outlined the compounds of the invention are metalloproteinase inhibitors, in particular they are inhibitors of MMP-12 and may be used in the treatment of diseases or conditions mediated by MMP-12 such as asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), psoriasis and hematological disorders.

The compounds of the invention typically show a favourable selectivity profile. Whilst we do not wish to be bound by theoretical considerations, the compounds of the invention are believed to show selective inhibition for any one of the above indications relative to any MMP-1 inhibitory activity, by way of non-limiting example they may show in excess of 100 fold selectivity over any MMP-1 inhibitory activity.

Accordingly, the present invention provides a compound of formula (I), or a pharmaceutically acceptable salt, a solvate, prodrug, N-oxide, quaternary amine, metal complex, or stereochemically isomeric form thereof, as hereinbefore defined for use in therapy. In another aspect, the invention provides the use of a compound of formula (I), or a pharmaceutically acceptable salt, a solvate, prodrug, N-oxide, quaternary amine, metal complex, or stereochemically isomeric form thereof, as hereinbefore defined in the manufacture of a medicament for use in therapy.

In the context of the present specification, the term "therapy" also includes "prophylaxis" unless there are specific indications to the contrary. The terms "therapeutic" and as "therapeutically" should be construed accordingly.

The invention further provides a method of treating a disease or condition mediated by MMP-12 which comprises administering to a patient a therapeutically effective amount of a compound of formula (I) or a pharmaceutically acceptable salt, a solvate, prodrug, N-oxide, quaternary amine, metal complex, or stereochemically isomeric form thereof, as hereinbefore defined.

The invention also provides a method of treating an obstructive airways disease (e.g. asthma or COPD) which comprises administering to a patient a therapeutically effective amount of a compound of formula (I) or a pharmaceutically acceptable salt or solvate thereof as hereinbefore defined.

For the above-mentioned therapeutic uses the dosage administered will, of course, vary with the compound employed, the mode of administration, the treatment desired and the disorder indicated. The daily dosage of the compound of formula I/salt/solvate (active ingredient) may be in the range from 0.001 mg/kg to 75 mg/kg, in particular from 0.5 mg/kg to 30 mg/kg. This daily dose may be given in divided doses as necessary. Typically unit dosage forms will contain about 1 mg to 500 mg of a compound of this invention.

The compounds of formula (I) and pharmaceutically acceptable salts, solvates, prodrugs, N-oxides, quaternary amines, metal complexes, or stereochemically isomeric forms thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition. A representative tablet within the scope of the pharmaceutical composition of the invention could have a mass of 500-1500 mg with a loading of active ingredient in the range 35-75%, with the balance being excipients, such as binders, disintegrants, antioxidants and the like.

Thus, the present invention also provides a pharmaceutical composition comprising a compound of formula (I) or a pharmaceutically acceptable salt or solvate thereof as hereinbefore defined in association with a pharmaceutically acceptable adjuvant, diluent or carrier. The invention further provides a process for the preparation of a pharmaceutical composition of the invention which comprises mixing a compound of formula (I) or a pharmaceutically acceptable salt or, a solvate, prodrug, N-oxide, quaternary amine, metal complex, or stereochemically isomeric form, thereof as hereinbefore defined with a pharmaceutically acceptable adjuvant, diluent or carrier.

The pharmaceutical compositions of this invention may be administered in standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or is aerosols for inhalation, and for parenteral use (including intravenous, intramuscular or infusion) sterile aqueous or oily solutions or suspensions or sterile emulsions.

The inhaled (including aerosol & nebulised) route is convenient, especially for compounds of formula I with a rapid metabolism. A large number of appropriate devices able to dose and entrain the pharmaceutical active and deliver it to the lungs of the patient are now available, even for COPD patients with a reduced respiratory capacity. See for example Byron's review in Proc. Am. Thorac. Soc. 2004: 1(4) 321-328 or Caprioti's review in Medsurg. Nurs. 2005: 14(3) 185-194.

The oral delivery route, particularly capsules or tablets is favoured, especially for advanced COPD patients with severely compromised respiratory capacity.

In addition to the compounds of the present invention the pharmaceutical composition of this invention may also contain, or be co-administered (simultaneously or sequentially) with, one or more pharmacological agents of value in treating one or more diseases or conditions referred to hereinabove. A representative example is inhaled steroids such as are conventionally used in asthma, for example budesonide and "Symbicort" (trade mark).

A general route to compounds according to the present invention wherein X and Y are both O is shown in scheme 1.

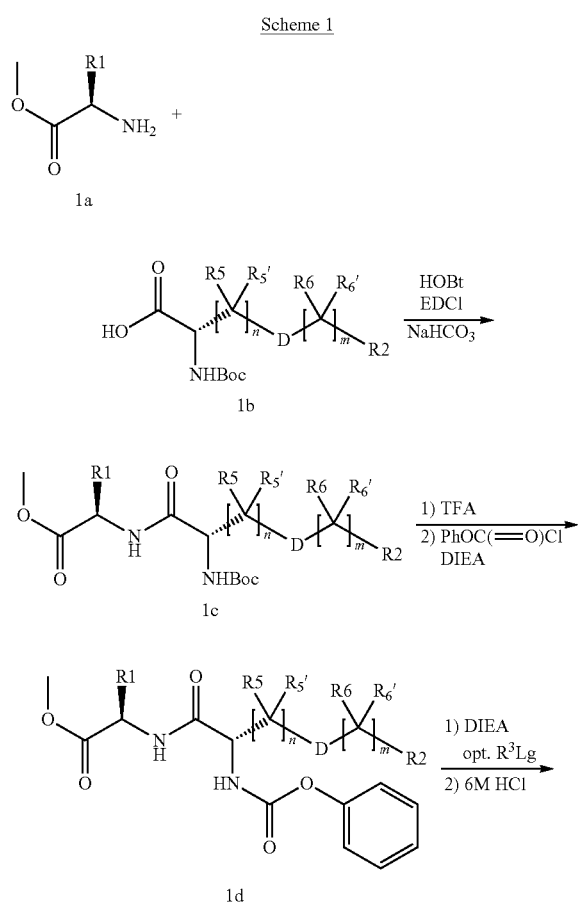

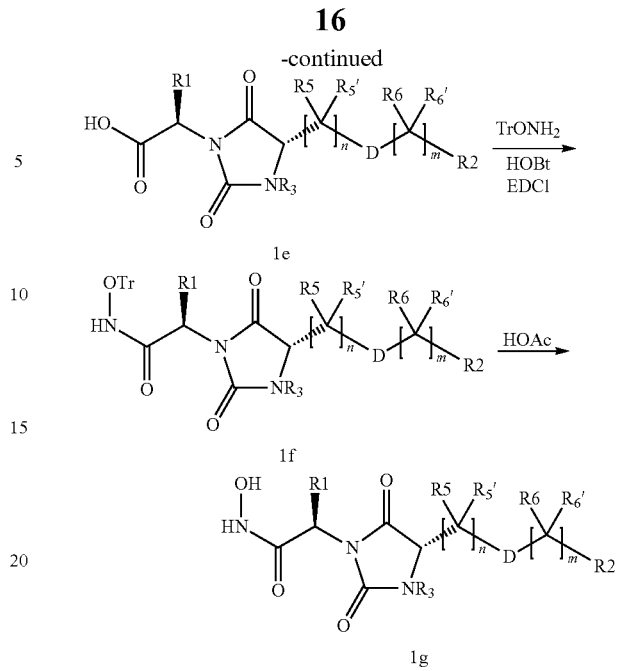

Coupling of two amino acids (1a) and (1b) carrying the appropriate side chains, $R^1$ and $(CR^5R^{5'})_n D(CR^6R^{6'})_m R^2$, by standard peptide coupling conditions like using couplings agents such as HOBt and EDCl or the like in the presence of a base such as DIEA, NaHCO$_3$ or the like in a solvent like DMF provides the dipeptide (1c). The hydantoin derivative (1e) can then be achieved by removal of the Boc group according to conventional procedures such as treatment with an acid for instance TFA or formic acid or the like in a solvent like dichloromethane, followed by formylation of the formed primary amine with a formylating agent such as phenyl chloroformate or phosgene or the like in the presence of a base like DIEA or NaHCO$_3$ and finally ring closure of the dipeptide effected for example by treatment of the afforded formyl derivative (1d) with a base such as DIEA or the like and subsequent hydrolysis of the methyl ester by treatment with an acid such as HCl. If an alkyl substituent, $R^3$ on the secondary nitrogen of the hydantoin ring is desired, this alkylation is conveniently performed subsequent to the ring closure of compound 1d and prior to the ester hydrolysis, by reaction with a desired alkylating agent such as $R^3$-Lg, wherein Lg is a leaving group such as a halide like a chloride, bromide or iodide or Lg is a derivative of sulphonic acid such as a triflate, tosylate mesylate or the like, optionally in the presence of a base such as t-BuOK. Coupling of hydroxylamine hydrochloride or a suitably protected hydroxylamine, for example, O-tritylhydroxylamine or O-bensylhydroxylamine using standard peptide coupling conditions such as using coupling agents like BOP and NMM in a solvent like DMF or as described above or by using any other convenient reagents, provides the hydroxamic acid derivative (1f). The free acid (1g) is then achieved after removal of the optional hydroxy protecting group carried out by using the appropriate conditions according to the protecting group, such as by acidic treatment in the case of a trityl protecting group.

Amino acids carrying the appropriate side chains for use in scheme 1 are commercially available or they can be prepared by the skilled person according to literature procedures. For example, amino acids carrying a side chain containing a thioether, amine, ether or carbamate group suitable for the preparation of compounds of general formula I wherein D is a thioether, amine, ether or amide linkage respectively, can be prepared from suitably protected, commercially available α-hydroxyalkyl amino acids as illustrated in scheme 2.

Scheme 2

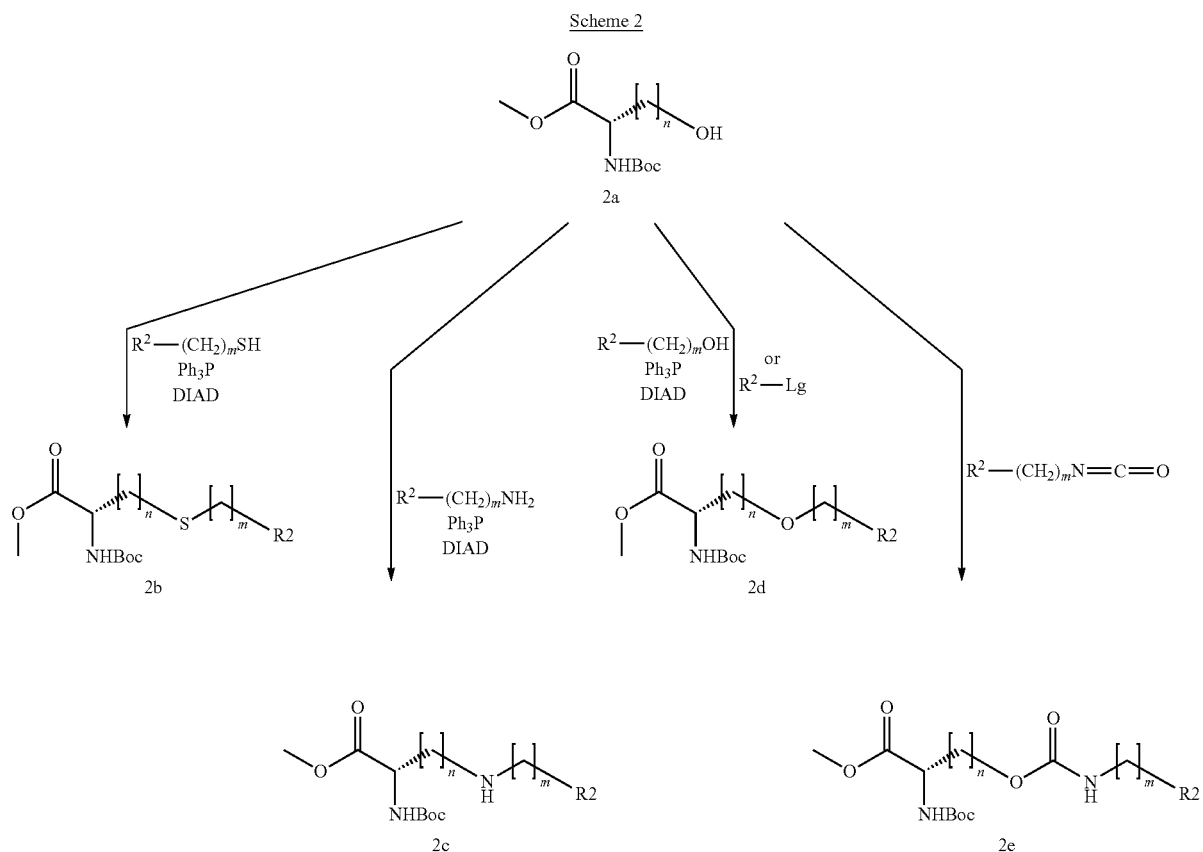

The hydroxy group of amino acid (2a) can be converted to a thioether, amine or ether function for instance by way of a Mitsunobu reaction, i.e. reaction of the hydroxy group of the alcohol (2a) with an azodicarboxylate such as DIAD or the like in the presence of triphenylphosphine or the like followed by displacement with a desired thiol, amine or alcohol to provide the thioether derivative (2b), the amine (2c) or the ether (2d) respectively. A big variety of thiols, amines and alcohols are available commercially or in the literature. An alternative method to obtain the amine derivative (2c) is to oxidize the hydroxy group of the alcohol (2a) to the corresponding aldehyde, effected for example by treatment with Dess-Martin periodinane or by any other suitable oxidation reagent, followed by a reductive amination with the desired amino derivative $R^2(CH_2)_mNH_2$. Ether derivatives (2d) can alternatively be achieved by alkylation of the hydroxy group of the alcohol (2a) by a displacement reaction with a suitable alkylating agent $R^2$-Lg, where Lg is a leaving group such as a trichloroimidate, a halide like a chloride, bromide or iodide, or a derivative of sulphonic acid such as a mesylate, triflate, tosylate or the like, in the presence of a base such as sodium hydride, $Ag_2O$, t.BuOK or the like in a solvent like DMF or THF or the like. Amino acids carrying a carbamate containing side chain can be prepared by reaction of amino acid (2a) with a suitable isocyanate $R^2N=C=O$ in the presence of a base like t.BuOK in a solvent like DMF or THF. Alternatively, compounds carrying a carbamate containing side chain can be prepared by reacting the hydroxy group of the amino acid (2a) with a formylating agent such phosgene or a suitable chlorocarbamate in the presence of a base like sodium hydrogen carbonate in a solvent like dichloromethane or toluene, followed by reaction with a desired amine $R^2$—$(CH_2)_mNH_2$. Derivatives substituted with the groups $R^4$, $R^5$, $R^{5'}$, $R^6$ and/or $R^{6'}$, can be prepared according to the above described method by using the appropriately substituted amino acids and alkylating agents.

Amino acids carrying an amide, carbamate, urea or sulponamide containing side chain, i.e. D is an amide, carbamate urea or sulpnonamide linkage respectively in compound (1b), can be prepared from α-aminoalkyl amino acids as illustrated in scheme 3. α-Aminoalkyl amino acids are commercially available or they can be prepared from the corresponding α-hydroxyalkyl amino acids according to literature procedures.

Scheme 3

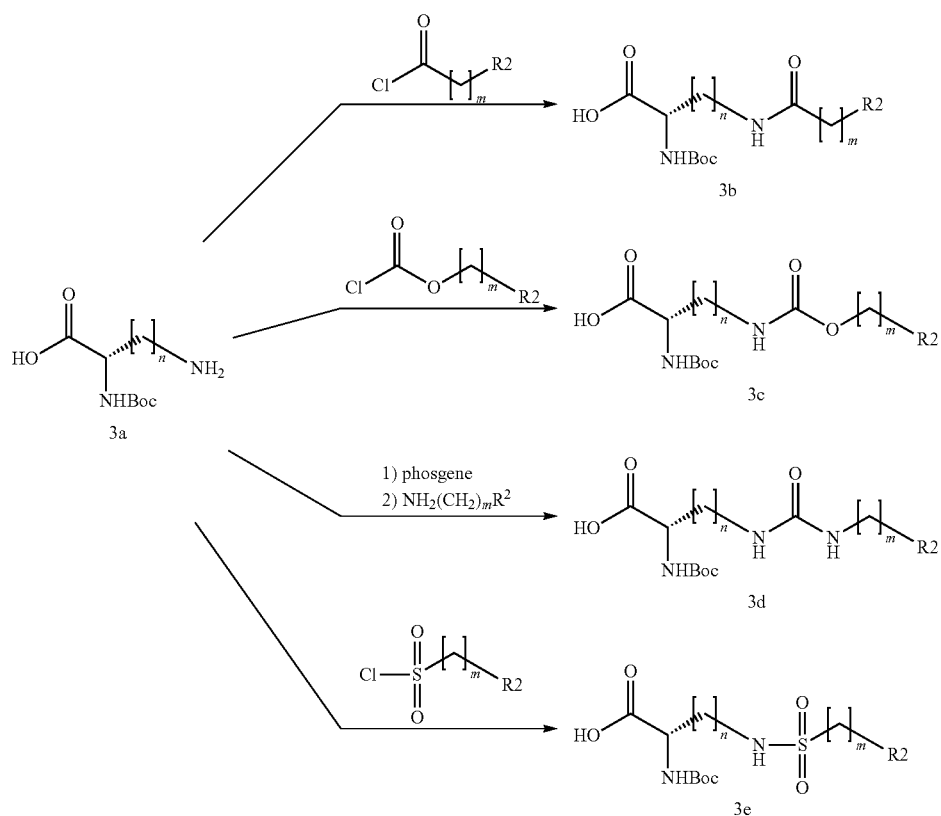

Reaction of the α-aminoalkyl amino acid (3a) with an appropriate acid chloride $R^2(CH_2)_m(C=O)Cl$ in a solvent like pyridine or dichloromethane optionally in the presence of a base like 4-dimethylaminopuridine or the like provides the amide (3b), reaction of the amine (3a) with a desired chloroformate $R^2(CH_2)_mO(C=O)Cl$ provides the carbamate (3c), whereas formylation of the amine (3a) using a convenient formylating agent for instance phosgene, p-nitrochloroformate, CDI or the like optionally in the presence of a base such as sodium hydrogen carbonate followed by reaction with the desired amino derivative $NH_2(CH_2)_mR^2$ provides the urea (3d) and finally, sulphonamides (3e) are obtained by reaction of the amine (3a) with a suitable sulphonyl chloride $R^2(CH_2)_m(S=O)_2Cl$ in a solvent like pyridine or dichloromethane optionally in the presence of a base like 4-dimethylaminopuridine. Secondary amines may also be achieved from the primary amine (3a) by alkylation of the nitrogen using any suitable alkylating agent such as an alkyl halide or an alkyl derivative of sulphonic acid as described above. Derivatives substituted with the groups $R^4$, $R^5$, $R^{5'}$, $R^6$ and/or $R^{6'}$, can be prepared according to the above described method by using the appropriately substituted amino acids and alkylating, acylating, sulphonylating or aminating agents.

Amino acids (1b) used in scheme 1 carrying a saturated or unsaturated all carbon side chain suitable for the preparation of compounds according to general formula I wherein D is absent and $R^2$ is a carbocyclic or heterocyclic aromatic system, are commercially available or they can be prepared from suitably protected α-amino-ω-hydroxy acids or the corresponding α-amino-ω-carboxy acids. An example is shown in scheme 3A.

Scheme 3A

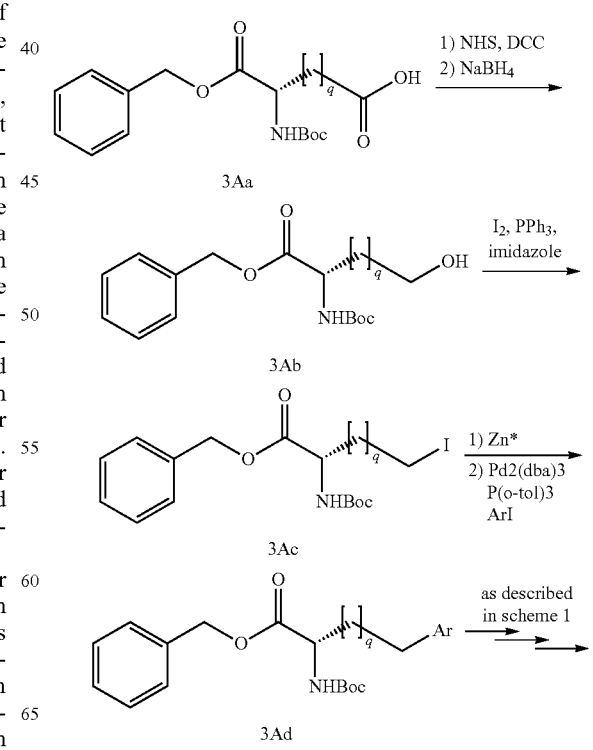

-continued

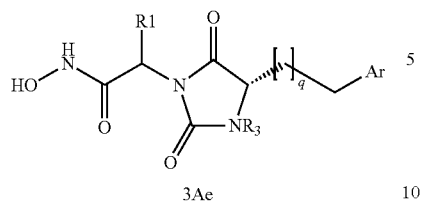

3Ae

Ar is a carbocyclic or heterocyclic aromatic system;
q is 0, 1, 2, 3, 4 or 5

The acid (3Aa) which is available commercially or in the literature, can be reduced to the corresponding alcohol (3Ab) by any suitable method known in the field of synthetic organic chemistry, for example the acid can be transformed to a suitable ester or acid halide like the N-hydroxysuccinimide followed by treatment with a reducing agent such as LiBH$_4$. The afforded alcohol (3Ab) can then be further reacted with iodine in the presence of triphenylphosphine and imidazole to provide the iodo derivative (3Ac). Conversion of the iodo derivative to the corresponding zink derivative by reaction with zink activated with 1,2-dibromoethane and chlorotrimethylsilane followed by a palladium catalyzed displacement reaction with a desired aryl iodide derivative, using for example tris(dibenzylideneacetone)palladium(0) as catalyst in the presence of a phosphine ligand like tri(o-tolyl)phosphine, gives the arylated amino acid (3Ad). Removal of the Boc group, coupling of an amino acid, ring closure, hydrolysis of the benzyl ester and introduction of the hydroxylamine moiety as described in scheme 1 gives the hydantoin derivative (3Ae).

Amino acids containing an α,β-unsaturated all carbon side chain useful for the preparation of compounds according to general formula I wherein R$^4$ and R$^5$ together form an olefinic bond, can be prepared for example as shown in scheme 3B.

Scheme 3B

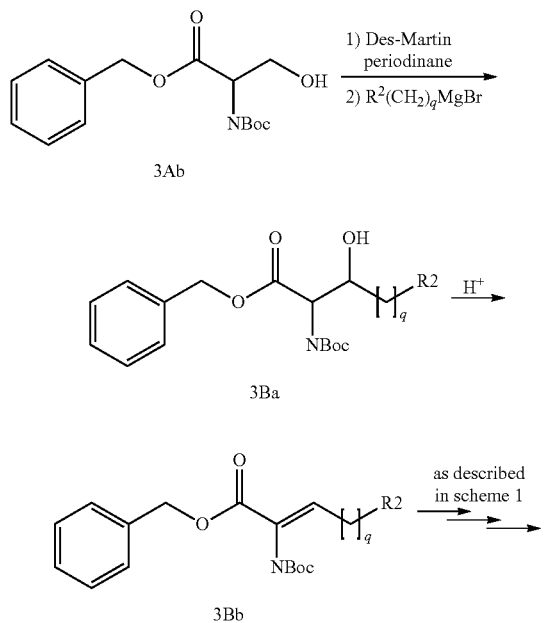

-continued

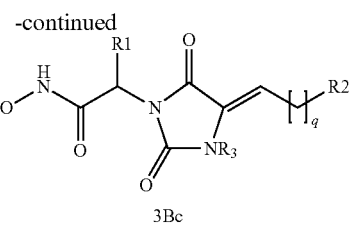

3Bc q is 0, 1, 2, 3, 4 or 5

Oxidation of the alcohol (3Ab) using an oxidizing agent such as Dess Martin periodinate to the corresponding aldehyde followed by a Grignard reaction or the like of with a desired Grignard reagent, R$^2$(CH$_2$)$_m$MgBr provides the hydroxy derivative (3Ba). Dehydration effected for instance by acidic treatment provides the unsaturated compound (3Bb) which subsequently can be treated as described in scheme 1 to give the desired hydantoin derivative (3Bc). The same strategy can also be applied in order to obtain compounds with other side chains such as alternative position of the olefinic bond or heteroatom containing side chains by choosing the appropriate hydroxyalkyl substituted amino acid and Grignard reagent.

Compounds containing a substituted R$^2$ moiety can be achieved by using an amino acid (1b) carrying the desired R$^2$-substituent in scheme 1, or the substituent can be introduced at a later stage of the synthesis. When the substituent is linked to R$^2$ by a carbon-carbon bond, it is conveniently introduced by a palladium catalyzed coupling reaction. Scheme 3C illustrates a method employing a Suzuki coupling.

Scheme 3C

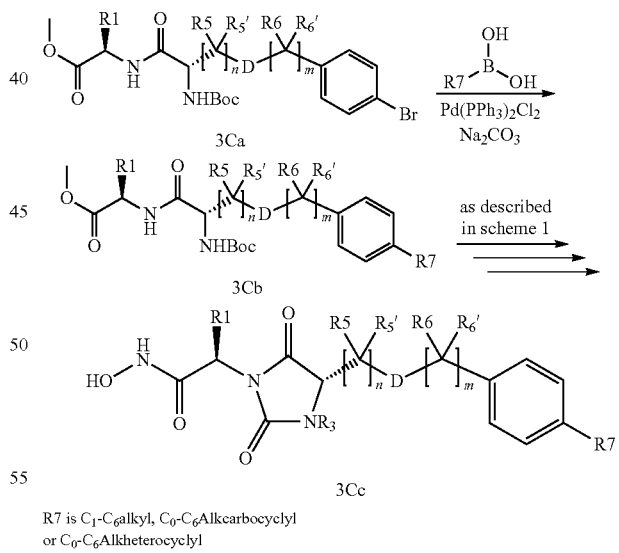

R7 is C$_1$-C$_6$alkyl, C$_0$-C$_6$Alkcarbocyclyl or C$_0$-C$_6$Alkheterocyclyl

Coupling of the dipeptide (3Ca) with the boronic acid derivative R$^7$B(OH)$_2$ of the desired substituent in the presence of a palladium catalyst such as Pd(PPh$_3$)$_2$Cl$_2$ or the like and a base like sodium carbonate provides the R$^7$-substituted dipeptide (3Cb). Removal of the Boc group, coupling of an amino acid, ring closure, hydrolysis of the benzyl ester and introduction of the hydroxylamine moiety as described in scheme 1 gives the hydantoin derivative (3Cc). Other palladium catalyzed coupling reactions known from the literature may alternatively be used for the introduction of a carbon linked substituent to R². For instance, a Heck coupling reaction wherein a desired activated alkene is coupled to an aromatic or vinylic R² moiety using a catalyst such as Pd(OAc)₂ or the like in the presence of a base such as triethylamine or potassium carbonate or the like provides alkene substituted compounds.

Although the method in scheme 3C is illustrated with a bromobenzene ring as R² group it should be understood that the same strategy is applicable to other R² groups such as substituted and unsubstituted carbocycles and heterocycles.

An alternative strategy for the preparation of the compounds of the invention is to first prepare a suitable hydantoin derivative and subsequently elongate the side chain and thus introduce the desired linkage D. Hydantoin derivatives carrying a hydroxyalkyl or aminoalkyl side chain whereto the various functional groups can be attached are suitable intermediates for this strategy. An example of their preparation is illustrated in scheme 4.

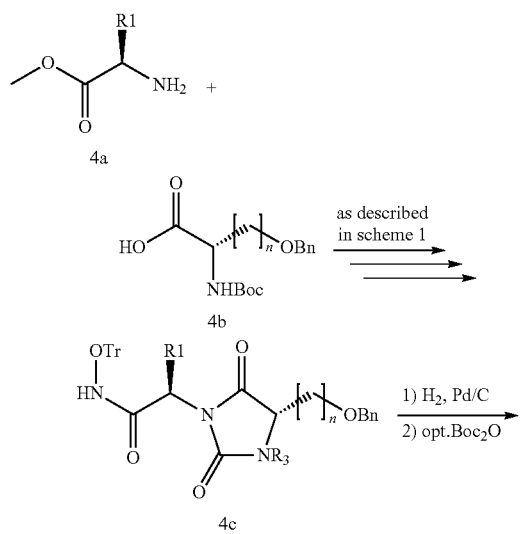

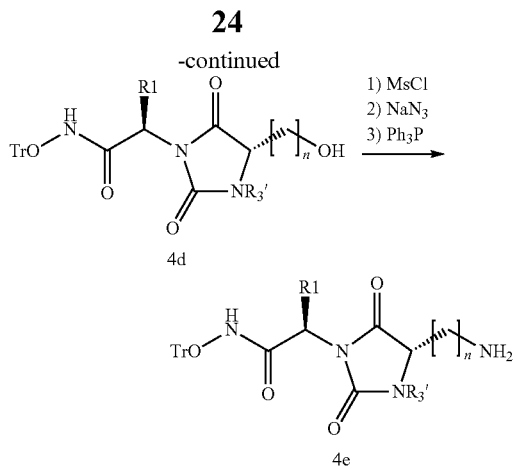

$R^{3'}$ is $C_1$-$C_4$alkyl or boc

The hydantoin derivative (4c) can be prepared from the two amino acids (4a) and (4b) as described in scheme 1. Removal of the benzyl group for example by catalytic hydrogenation using a catalyst such as palladium on carbon optionally in the presence of a base like sodium hydrogen carbonate and in the case of $R^3$ being hydrogen, protection of the ring nitrogen with any suitable amino protecting group such as a boc group using standard methods well known in the art, gives the hydroxyalkyl derivative (4d). The corresponding aminoalkyl derivative (4e) can then be prepared by conversion of the hydroxy group to an amino group for example by transforming the hydroxy group to a leaving group such as a mesylate or the like by treatment with mesylchloride in a solvent like pyridine optionally in the presence of a base such as triethylamine followed by displacement of the leaving group with azide and finally reduction of the azide to an amine by any suitable reduction method such as treatment with Ph₃P. Derivatives substituted with the groups $R^4$, $R^5$ and/or $R^{5'}$ can be prepared according to the above described method by using the appropriately substituted amino acid instead of the unsubstituted amino acid (4b).

Subsequent elongation of the hydroxyalkyl side chain in order to obtain a thioether, amine, ether or carbamate containing side chain can be performed as illustrated in scheme 5.

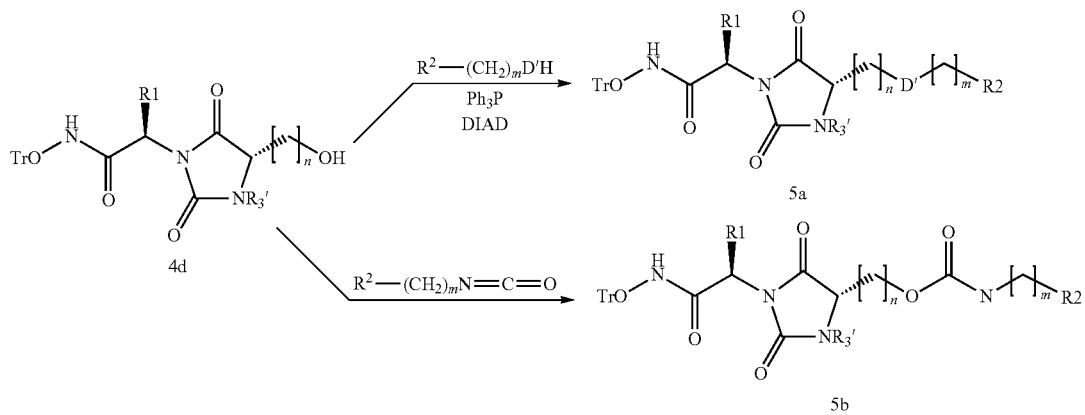

D' is O, NH or S
R3' is $C_1$-$C_4$alkyl or boc

The hydroxy group of the hydantoin (4d) can be converted to a thioether, amine or ether function for instance by way of a Mitsunobu reaction, i.e. reaction of the hydroxy group of the alcohol (4d) with an azodicarboxylate such as DIAD or the like in the presence of triphenylphosphine or the like followed by displacement with a desired thiol, amine or alcohol to provide the thioether, amine or the ether derivative respectively. A big variety of thiols, amines and alcohols are available commercially or in the literature. An alternative method to obtain amine derivatives, i.e. D' is NH, is to oxidize the hydroxy group of the alcohol (4d) to the corresponding aldehyde, effected for example by treatment with Dess-Martin periodinane or by any other suitable oxidation reagent, followed by a reductive amination with the desired amino derivative $R^2(CH_2)_mNH_2$. Ether derivatives, i.e. D' is O, can alternatively be achieved by alkylation of the hydroxy group of the alcohol (4d) by a displacement reaction with a suitable alkylating agent $R^2$-Lg, where Lg is a leaving group such as a trichloroimidate or a halide like a chloride, bromide or iodide, or a derivative of sulphonic acid such as a mesylate, triflate, tosylate or the like, in the presence of a base such as sodium hydride, $Ag_2O$ t.BuOK or the like in a solvent like DMF or THF or the like. Amino acids carrying a carbamate containing side chain can be prepared by reaction of hydantoin (4d) with a suitable isocyanate $R^2(CH_2)_mN=C=O$ in the presence of a base like t.BuOK in a solvent like DMF or THF. Alternatively, compounds carrying a carbamate containing side chain can be prepared by reacting the hydroxy group of the hydantoin (4d) with a formylating agent such phosgene in the presence of a base like sodium hydrogen carbonate in a solvent like dichloromethane or toluene, followed by reaction with a desired amine $R^2(CH_2)_mNH_2$.

Hydantoins carrying an amide, carbamate, urea or sulphonamide containing side chain, i.e. D is an amide, carbamate, urea or sulphonamide linkage respectively in general formula (I), can be prepared from α-aminoalkyl amino acids (4e) as illustrated in scheme 6.

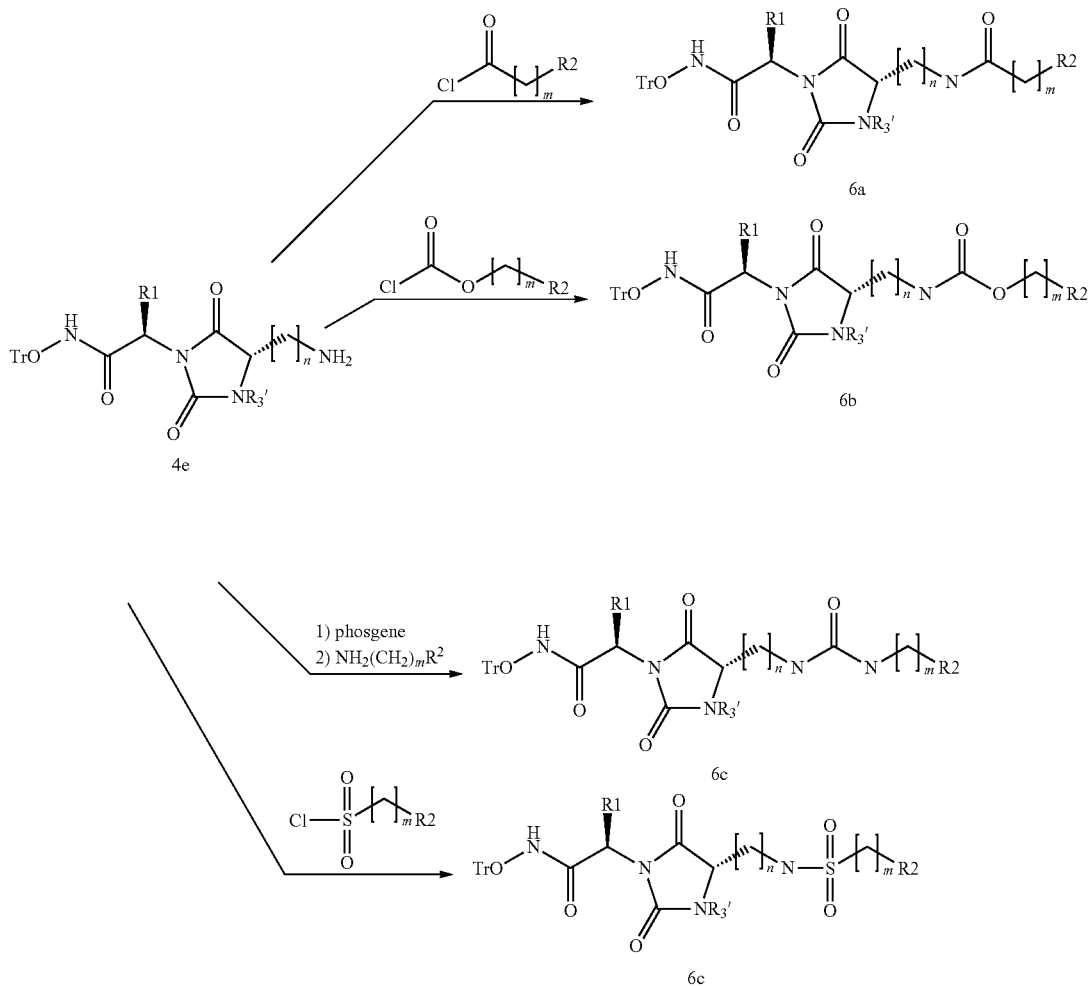

Scheme 6

$R^{3'}$ is $C_1$-$C_4$ alkyl or boc

Reaction of the α-aminoalkyl hydantoin (4e) with an appropriate acid chloride $R^2(CH_2)_m(C=O)Cl$ in a solvent like pyridine or dichloromethane optionally in the presence of a base like 4-dimethylaminopyridine or the like provides the amide (6a), reaction with a desired chloroformate $R^2(CH_2)_m O(C=O)Cl$ provides the carbamate (6b) whereas formylation of the amine (4e) using a convenient formylating agent, for instance phosgene, p-nitrochloroformate, CDI or the like optionally in the presence of a base such as sodium hydrogen carbonate followed by reaction with the desired amino derivative $NH_2(CH_2)_mR^2$ provides the urea (6c) and finally, sulphonamides (6d) are obtained by reaction of the amine (4e) with a suitable sulphonyl chloride $R^2(CH_2)_m(S=O)_2Cl$ in a solvent like pyridine or dichloromethane optionally in the presence of a base like 4-dimethylaminopyridine. Secondary amines, i.e. D is an amino linkage in general formula I, may also be prepared from the primary amine (4e) by alkylation of the nitrogen using any suitable alkylating agent such as an alkyl halide or an alkyl derivative of sulphonic acid as described above. Removal of the protecting groups, boc and trityl, by standard methods such as acidic treatment then provides the unprotected hydroxamic acids. Derivatives substituted with the groups $R^4$, $R^5$, $R^{5'}$, $R^6$ and/or $R^{6'}$, can be prepared according to the above described method by using the appropriately substituted amino acid and acylating, sulphonylating or aminating agents.

Compounds according to the present invention wherein one or both of the carbonyl groups of the hydantoin moiety is replaced by thiocarbonyl are conveniently prepared from thiopeptides. Various methods for the preparation of thiopeptides are described in the literature and one example, described by R. Michelot et al. in Bioorganic & Medicinal Chemistry Vol. 4, No 12 1996 p. 2201-2209, is shown in Scheme 7.

amino acid with isobutylchloroformate and N-methylmorpholine in a solvent like THF followed by treatment with $H_2S$ and subsequent acidifying with for instance HCl. Coupling of the afforded amino thioacid with a natural or unnatural amino acid (7b) under standard peptide coupling conditions such as using a coupling reagent like BOP-Cl or PyBOP or the like in the presence of a base such as DIEA or the like in a solvent like THF provides the thiodipeptide (7c).

Alternatively, the thiodipeptide (7c) can be achieved from the amino acid (2b, 2c, 2d or 2e) by converting the acid function to a nitrile by using for instance a reagent like trimethylsilanecarbonitrile in the presence of a Lewis acid such as $BF_3$—$OEt_2$ followed by treatment as described by C. H. Williams et al. in J. Chem. Soc. Perkin Trans. I, 1988, p. 1051-1055 and finally coupling of the second amino acid (7b) as described above.

A further alternative to the thiodipeptide (7c) is by conversion of the dipeptide (1c) by using the thionation reagent 2,4-bis(4-methoxyphenyl)-1,2,3,4-dithiadiphosphetane 2,4-disulfide described by K. Clausen et al. in Tetrahedron, Vol. 37, 1981, p. 3635-3639.

Amino thioacids substituted with the groups $R^4$, $R^5$, $R^{5'}$, $R^6$ and/or $R^{6'}$, can be prepared according to the above described methods by starting from the appropriately substituted compounds corresponding to amino acids (2b-2e) carrying the desired substituents.

A thiohydantoin derivative can then be formed by taking the thiodipeptide (7c) through the steps described for the dipeptide (1c) in scheme 1. An example is shown in scheme 8.

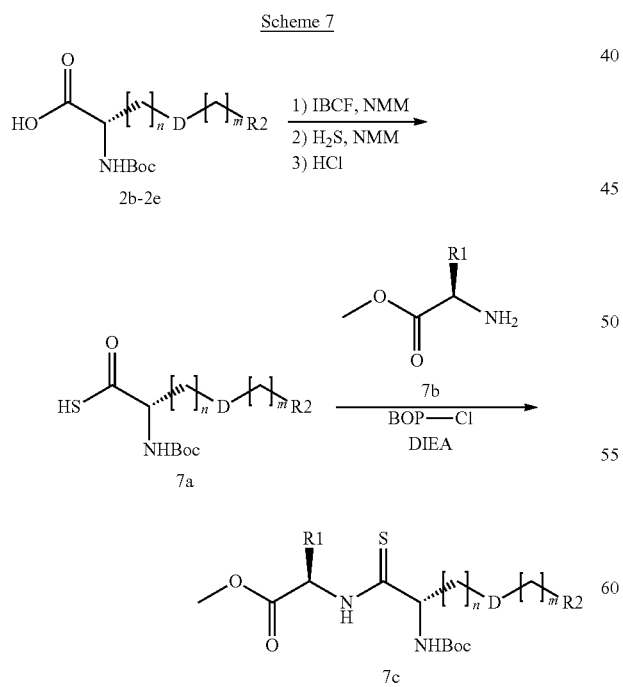

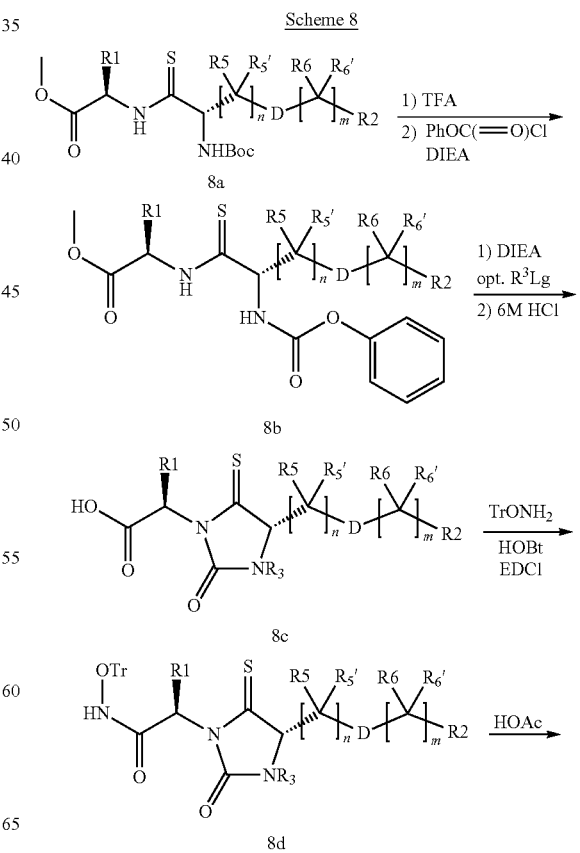

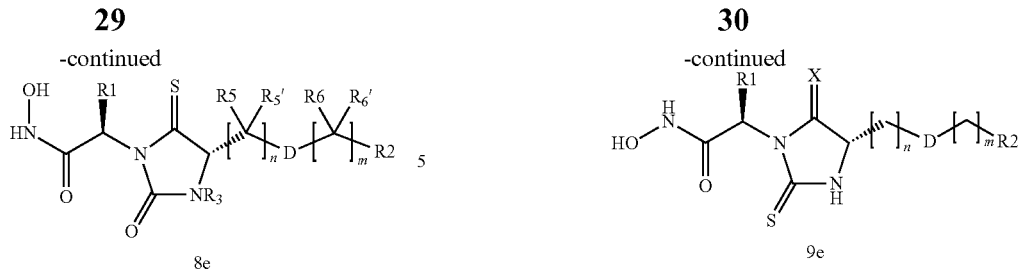

8e

Removal of the Boc group from thiodipeptide (8a) by treatment with an acid for instance TFA or formic acid in a solvent like dichloromethane, followed by formylation of the formed primary amine with a formylating agent such as phenyl chloroformate or phosgene or the like in the presence of a base like DIEA or NaHCO$_3$ yields the carbamate (8b). Ring closure of the thiodipeptide effected for example by treatment with a base such as DIEA or the like and subsequent hydrolysis of the methyl ester by treatment with an acid such as HCl gives the carboxylic acid (8c). Coupling of hydroxylamine hydrochloride or a suitably protected hydroxylamine, for example, O-tritylhydroxylamine or O-bensylhydroxylamine using standard peptide coupling conditions such as using coupling reagents like BOP and NMM in a solvent like DMF or as described above or any other convenient reagents, provides the hydroxamic acid (8c). The free acid (8e) is then achieved after removal of the optional hydroxy protecting group carried out by using the appropriate conditions according to the protecting group, such as by acidic treatment in the case of a trityl protecting group.

Scheme 9 illustrates a method to prepare compounds according to general formula I wherein Y is S and X is O or S.

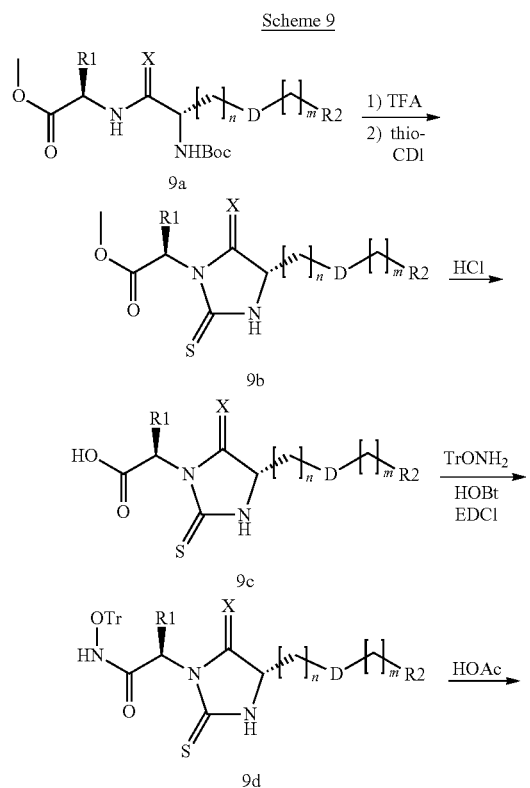

Removal of the Boc group from thiodipeptide (9a), prepared as described in scheme 1 or 7, by treatment with an acid for instance TFA or formic acid or the like in a solvent like dichloromethane, followed by ring closure effected for example by reaction with thiocarbonyl diimidazole or the like provides the hydantoin derivative (9b). Subsequent hydrolysis of the methyl ester by treatment with an acid such as HCl gives the carboxylic acid (9c). Coupling of hydroxylamine hydrochloride or a suitably protected hydroxylamine, for example, O-tritylhydroxylamine or O-bensylhydroxylamine using standard peptide coupling conditions such as using coupling reagents like BOP and NMM in a solvent like DMF or as described above or any other convenient reagents, provides the hydroxamic acid (9d). The free acid (9e) is then achieved after removal of the optional hydroxy protecting group carried out by using the appropriate conditions according to the protecting group, such as by acidic treatment in the case of a trityl protecting group.

It will be readily apparent that the above described methods are not limited to the stereochemistries indicated. The same methods are also applicable to reactants having other sterochemistries and to racemates, the obtained product will have the configuration corresponding to the one of the reactants.

Any functional groups present on any of the constituent compounds used in the preparation of the compounds of the invention are appropriately protected where necessary. For example functionalities on the natural or non-natural amino acids are typically protected as is appropriate in peptide synthesis. Those skilled in the art will appreciate that the selection and use of appropriate protecting groups depend upon the reaction conditions. Suitable protecting groups are described in Greene, "Protective Groups in Organic Synthesis", John Wiley & Sons, New York (1981) and "The Peptides: Analysis, Synthesis, Biology", Vol. 3, Academic Press, New York (1981), the disclosure of which are hereby incorporated by reference.

DETAILED DESCRIPTION

Various embodiments of the compounds of the invention and key intermediates towards such compounds will now be described by way of illustration only with reference to the accompanying non-limiting chemistry and biology examples.

Method A

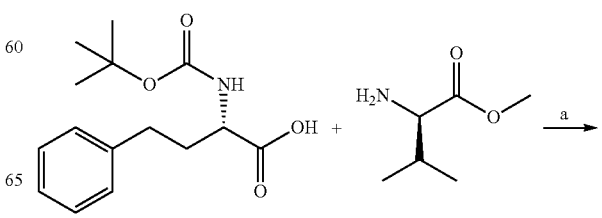

31
-continued

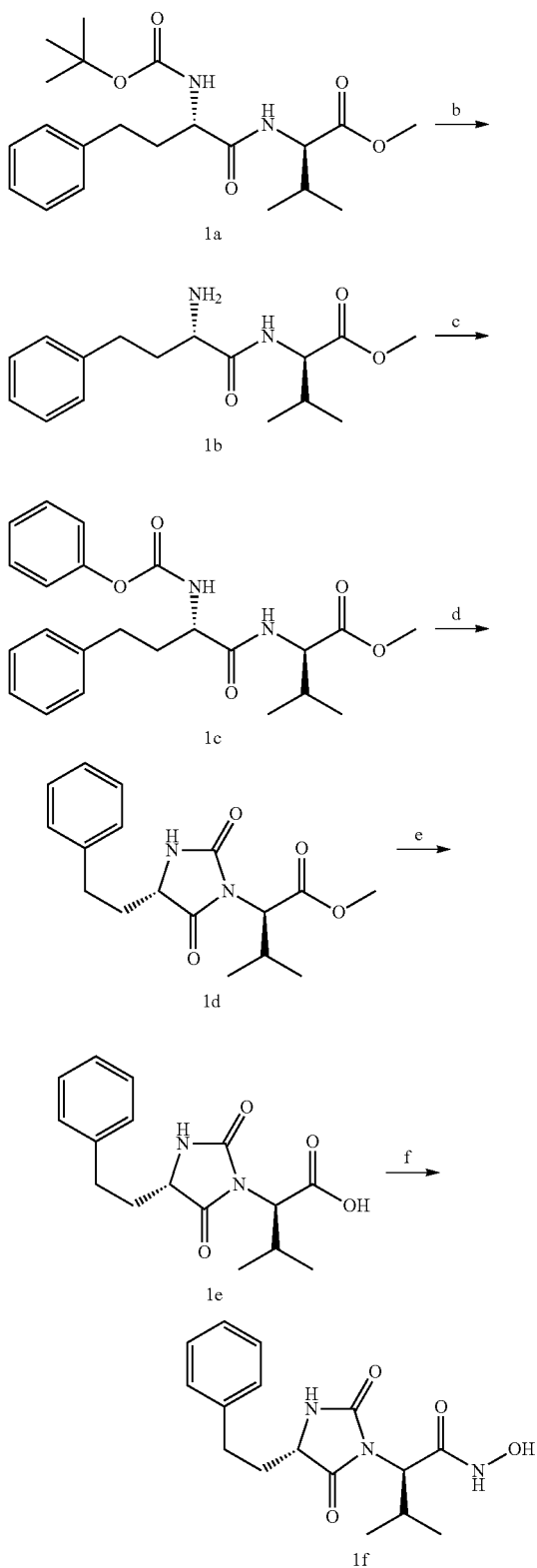

a) HOBt, EDC, NMM, DMF; b) TFA/CH₂Cl₂; c) DIEA,
PhOC(=O)Cl, dioxane/H₂O; d) DIEA, DMF; e) 6M HCl; f) BOP, DMF, NMM,
NH₂OHxHCl

32

Example 1

Step a

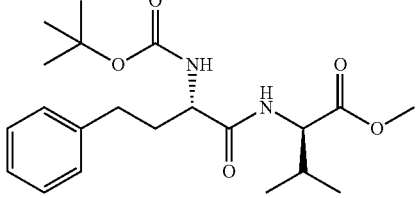

2-(2-Tert-butoxycarbonylamino-4-phenyl-butyry-lamino)-3-methylbutyric acid methyl ester (1a)

To an ice-cooled solution of D-valine methyl ester hydrochloride (1000 mg, 3.58 mmol) and HOBt (in DMF (14 mL) was added EDCl (755 mg, 3.94 mmol). After the mixture was stirred for 30 min, N-boc-L-homophenylalanine (600 mg, 3.58 mmol) and N-methylmorpholine (1 mL, 8.95 mmol) were added. The mixture was warmed to room temperature and stirred overnight. The solvent was removed and the residue was partitioned between water and EtOAc. The aqueous layer was extracted with EtOAc and the combined organic phases were dried over anhydrous Na₂SO₄. After concentration under reduced pressure, the crude title compound (2000 mg) was obtained and used in the next step without further purification.

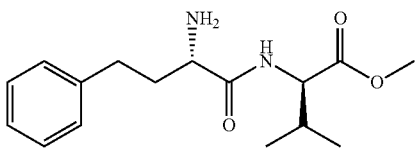

Step b 2-(2-Amino-4-phenyl-butyrylamino)-3-methylbutyric acid methyl ester (1b)

To a solution of the crude compound obtained in step a above (2000 mg) in CH₂Cl₂ (10 mL) was added TFA (10 mL). After stirring for 1.5 h at room temperature, the mixture was concentrated. The residue was diluted with EtOAc whereafter 10% NaOH was added to adjust the pH to 14. The aqueous layer was extracted with EtOAc and the combined organic phases were dried over anhydrous Na₂SO₄. After concentration under reduced pressure, the crude title product (1400 mg) was obtained for next step without further purification.

Step c

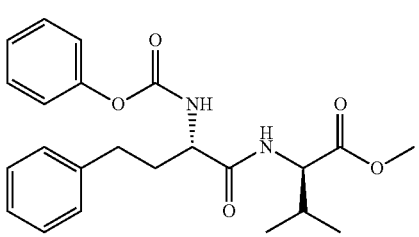

3-Methyl-2-(2-phenoxycarbonylamino-4-phenyl-butyrylamino)-butyric acid methyl ester (1c)

To a mixture of the crude compound obtained in step b above (1400 mg) in dioxane (18 mL) and water (2 mL) was added phenyl chloroformate (0.9 mL, 7.16 mmol) and DIEA (1.6 mL, 8.95 mmol). The mixture was stirred at room temperature for 3 h and concentrated under reduced pressure. The residue was partitioned between water and EtOAc. The aqueous layer was extracted with EtOAc, the combined organic phases were dried and concentrated. The residue was purified by silica gel column chromatography to afford the title compound as a white solid (1165 mg, 79% yield, three steps).

$^1$H NMR (300 MHz, CDCl$_3$): δ 0.89 (d, J=6.6 Hz, 3H); 0.94 (d, J=6.6 Hz, 3H); 2.00-2.35 (m, 3H); 2.70-2.80 (m, 2H); 3.73 (s, 3H); 4.30-4.45 (m, 1H); 4.30-4.45 (m, 1H); 4.57 (dd, J=8.1, 9.0 Hz, 1H); 5.84 (d, J=8.1 Hz, 1H); 5.84 (d, J=8.1 Hz, 1H); 6.65 (d, J=9.0 Hz, 1H); 7.10-7.40 (m, 10H).

Step d

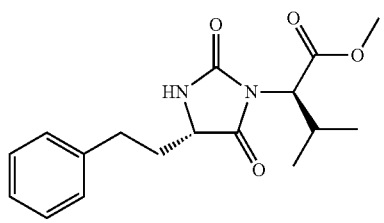

2-(2,5-Dioxo-4-phenethyl-imidazolidin-1-yl)-3-methyl-butyric acid methyl ester (1d)

To a solution of the compound obtained in step c above (1140 mg) in DMF (14 mL) was added DIEA (0.6 mL, 3.30 mmol). After stirring overnight at room temperature, the solvent was removed. The residue was diluted with EtOAc and washed with water. The organic layer was dried and concentrated under reduced pressure. The residue was purified by silica gel column chromatography to afford the title compound as a colourless oil (672 mg, 77%).

$^1$H NMR (300 MHz, CDCl$_3$): δ 0.92 (d, J=6.9 Hz, 3H); 1.12 (d, J=6.9 Hz, 3H); 1.95-2.35 (m, 2H); 2.60-2.85 (m, 3H); 3.71 (s, 3H); 4.00-4.10 (m, 1H); 4.35 (d, J=8.4 Hz, 1H); 7.00 (s, 1H); 7.10-7.35 (m, 5H).

Step e

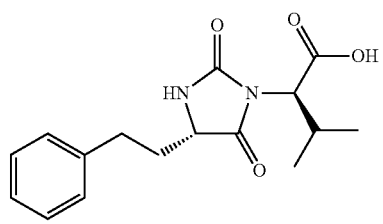

2-(2,5-Dioxo-4-phenethyl-imidazolidin-1-yl)-3-methyl-butyric acid (1e)

A mixture of the compound obtained in step d above (482 mg, 1.52 mmol) and 6 N HCl (20 mL) was stirred at 70° C. for 3 h. The reaction mixture was cooled to room temperature and extracted with CH$_2$Cl$_2$. The combined organic phases were washed with brine, dried and concentrated. The residue was purified by silica gel column chromatography to afford the title compound as a colorless oil (210 mg, 46% yield) with a recover of starting material (200 mg).

$^1$H NMR (300 MHz, CD$_3$OD): δ 0.86 (d, J=6.8 Hz, 3H); 1.01 (d, J=6.8 Hz, 3H); 1.94-2.20 (m, 2H); 2.50-2.80 (m, 3H); 4.10-4.15 (m, 1H); 4.27 (d, J=8.4 Hz, 1H); 7.10-7.30 (m, 5H).

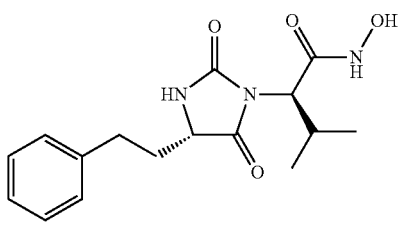

Step f 2-(2,5-Dioxo-4-phenethyl-imidazolidin-1-yl)-N-hydroxy-3-methyl-butyramide (1f)

To a solution of the compound obtained in step e above (109 mg, 0.36 mmol) in DMF (1.8 mL) was added BOP (190 mg, 0.43 mmol) at 0° C. After stirring for 30 min, HONH$_2$× HCl (50 mg, 11.38 mmol) and N-methylmorpholine (0.16 mL, 1.44 mmol) were added. The mixture was warmed to room temperature and stirred overnight. The solvent was removed and the residue was partitioned between EtOAc and a saturated solution of NH$_4$Cl. The aqueous layer was extracted with EtOAc, dried and concentrated. The residue was purified by silica gel column chromatography to afford the title compound as a white solid (63 mg, 55% yield).

$^1$H NMR (300 MHz, CD$_3$OD): δ0.89 (d, J=6.8 Hz, 3H); 1.01 (d, J=6.8 Hz, 3H); 1.94-2.20 (m, 2H); 2.60-2.80 (m, 2H); 2.80-3.00 (s, 1H); 4.00-4.10 (m, 2H); 7.10-7.30 (m, 5H).

Example 2

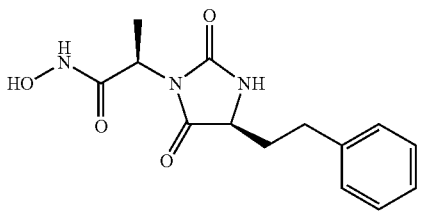

2-(2,5-Dioxo-4-phenethyl-imidazolidin-1-yl)-N-hydroxy-propionamide (2)

The procedure described in method A was followed but using D-alanine methyl ester hydrochloride instead of D-valine methyl ester hydrochloride which gave the title compound (8 mg)

¹H NMR (300 MHz, CD₃OD): δ 1.56 (dd, J=2.7, 7.2 Hz, 3H), 1.90-2.20 (m, 2H), 2.72 (dd, J=7.8, 7.8 Hz, 2H), 4.00-4.15 (m, 1H), 4.60-4.15 (m, 1H), 7.10-7.35 (m, 5H).

Example 4

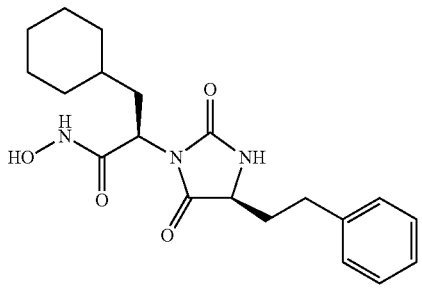

3-Cyclohexyl-2-(2,5-dioxo-4-phenethyl-imidazolidin-1-yl-N-hydroxy-propionamide (4)

The procedure described method A was followed but using D-cyclohexyl-alanine methyl ester hydrochloride instead of D-valine methyl ester hydrochloride which gave the title compound (3 mg).

¹H NMR (300 MHz, CDCl₃): δ 0.80-2.10 (m, 16H), 2.72 (s, 2H), 4.09 (s, 1H), 4.70-4.75 (m, 1H), 6.98 (s, 1H), 7.10-7.35 (m, 5H), 10.06 (s, 1H).

Example 5

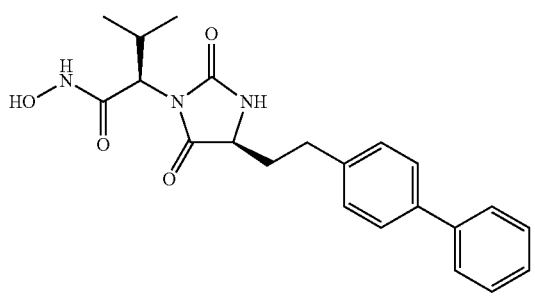

2-[4-(2-Biphenyl-4-yl-ethyl)-2,5-dioxo-imidazolidin-1-yl]-N-hydroxy-3-methyl-butyramide (5)

The procedure described method A was followed but using 4-biphenyl-4-yl-2-tert-butoxycarbonylamino-butyric acid instead of N-boc-L-homophenylalanine, which gave the title compound (6 mg).

¹H NMR (300 MHz, CDCl₃): δ 0.84 (d, J=6.0 Hz, 3H), 1.03 (d, J=6.0 Hz, 3H), 1.94-2.30 (m, 2H), 2.50-2.80 (m, 3H), 4.10-4.15 (m, 1H), 4.25 (d, J=11.4 Hz, 1H), 6.30-6.50 (m, 1H), 7.10-7.60 (m, 9H), 10.10 (s, 1H).

Example 6

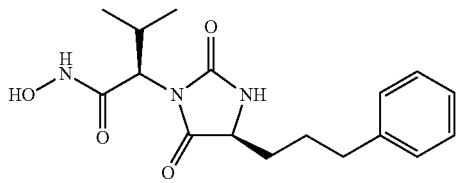

2-[2,5-Dioxo-4-(3-phenylpropyl)-imidazolidin-1-yl]-N-hydroxy-3-methyl-butyramide (6)

The procedure described method A was followed but using 2-tert-butoxycarbonylamino-5-phenyl-pentanoic acid instead of N-boc-L-homophenylalanine, which gave the title compound (8 mg).

¹H NMR (300 MHz, CDCl₃): δ 0.93 (d, J=6.6 Hz, 3H), 1.03 (d, J=6.6 Hz, 3H), 1.90-2.10 (m, 4H), 2.55-2.85 (m, 3H), 4.00-4.15 (m, 1H), 4.27 (d, J=11.4 Hz, 1H), 6.30 (s, 1H), 7.15-7.35 (m, 5H), 8.12 (s, 1H).

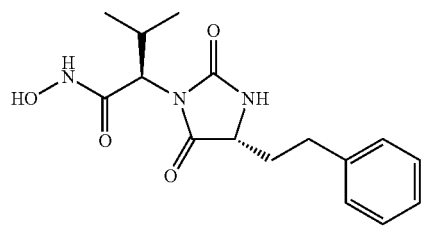

Example 7

2-(2,5-Dioxo-4-phenethyl-imidazolidin-1-yl)-N-hydroxy-3-methyl-butyramide (7)

The procedure described method A was followed but using N-boc-D-homophenylalanine instead of N-boc-L-homophenylalanine, which gave the title compound (10 mg).

¹H NMR (300 MHz, CDCl₃): δ 0.83 (d, J=6.6 Hz, 3H), 1.03 (d, J=6.6 Hz, 3H), 1.90-2.10 (m, 1H), 2.20-2.30 (m, 1H), 2.60-2.80 (m, 3H), 4.00-4.20 (m, 1H), 4.27 (d, J=11.4 Hz, 1H), 6.30 (s, 1H), 7.15-7.40 (m, 5H), 8.12 (s, 1H).

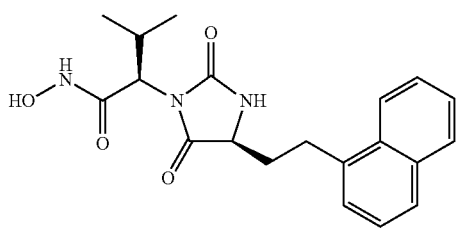

Example 8

N-Hydroxy-3-methyl-2-[4-(2-naphtalen-1-yl-ethyl)-(2,5-dioxo-imidazolidin-1-yl)-butyramide (8)

The procedure described method A was followed but using 2-tert-butoxycarbonylamino-4-naphtalen-1-yl-butyric acid instead of N-boc-L-homophenylalanine, which gave the title compound (20 mg).

$^1$H NMR (300 MHz, CDCl$_3$): δ 0.85 (d, J=6.6 Hz, 3H), 1.04 (d, J=6.6 Hz, 3H), 2.00-2.30 (m, 2H), 2.50-2.70 (m, 1H), 3.10-3.30 (m, 2H), 4.10-4.25 (m, 1H), 4.29 (d, J=11.1 Hz, 1H), 6.03 (s, 1H), 7.10-8.00 (m, 9H), 10.10 (s, 1H).

Example 9

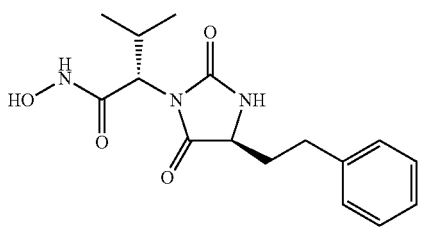

2-(2,5-Dioxo-4-phenethyl-imidazolidin-1-yl)-N-hydroxy-3-methyl-butyramide (9)

The procedure described method A was followed but using L-valine methyl ester hydrochloride instead of D-valine methyl ester hydrochloride, which gave the title compound (15 mg).

$^1$H NMR (300 MHz, CD$_3$OD): δ 0.88 (d, J=6.4 Hz, 3H), 1.02 (d, J=6.5 Hz, 3H), 1.97-1.92 (m, 1H), 2.11-2.06 (m, 1H), 2.72-2.67 (m, 2H), 2.92-2.86 (m, 1H), 4.10-4.03 (m, 2H), 7.30-7.18 (m, 5H).

Example 10

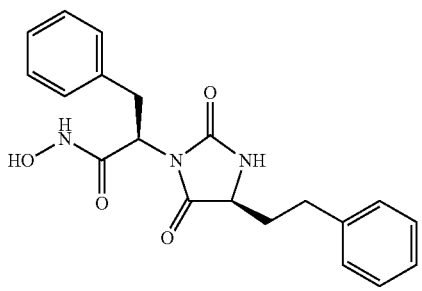

2-(2,5-Dioxo-4-phenethyl-imidazolidin-1-yl)-N-hydroxy-3-phenhyl-propionamide (10)

The procedure described method A was followed but using D-phenylalanine methyl ester hydrochloride instead of D-valine methyl ester hydrochloride, which gave the title compound (3 mg).

$^1$H NMR (300 MHz, CD$_3$OD): δ 1.64-1.61 (m, 1H), 1.95-1.91 (m, 1H), 2.49-2.45 (m, 2H), 3.42-3.39 (m, 2H), 3.93-3.85 (m, 1H), 4.97-4.90 (m, 1H), 6.90-6.75 (m, 1H), 7.26-7.00 (m, 10H).

Example 11

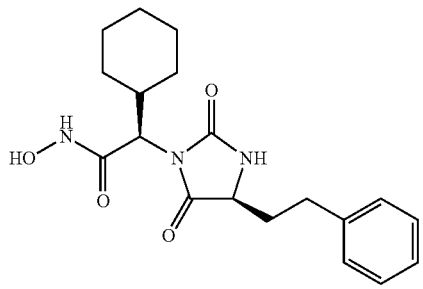

2-Cyclohexyl-2-(2,5-dioxo-4-phenethyl-imidazolidin-1-yl)-N-hydroxy-acetamide (11)

The procedure described method A was followed but using D-cyclohexylglycine methyl ester hydrochloride instead of D-valine methyl ester hydrochloride, which gave the title compound (4 mg).

$^1$H NMR (300 MHz, CDCl$_3$): δ 1.49-0.84 (m, 6H), 1.81-1.66 (m, 4H), 2.06-1.96 (m, 1H), 2.38-2.23 (m, 2H), 2.80-2.76 (m, 2H), 4.11-3.99 (m, 1H), 4.32-4.28 (m, 1H), 6.79 (s, 1H), 7.34-7.20 (m, 5H).

Example 12

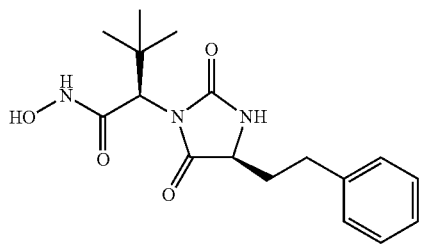

2-(2,5-Dioxo-4-phenethyl-imidazolidin-1-yl)-N-hydroxy-3,3-dimethyl-butyramide (12)

The procedure described method A was followed but using D-tert.butylglycine methyl ester hydrochloride instead of D-valine methyl ester hydrochloride, which gave the title compound (2 mg).

$^1$H NMR (300 MHz, CD$_3$OD): δ 1.11 (s, 9H), 2.01-1.89 (m, 1H), 2.18-2.07 (m, 1H), 2.75-2.70 (m, 2H), 4.05 (dd, J$_1$=6.9 Hz, J$_2$=2.1 Hz, 1H), 4.41 (s, 1H), 7.30-7.15 (m, 5H).

Method B

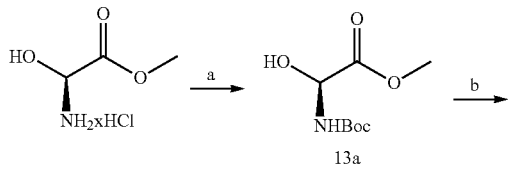

Example 13

Step a

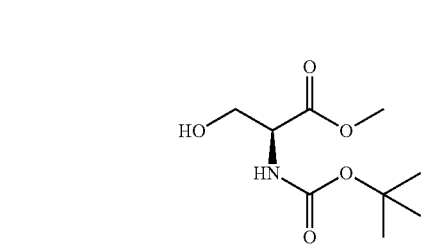

2-Tert-butoxycarbonylamino-3-hydroxy-propionic acid methyl ester (13a)

To a solution of L-serine methyl ester hydrochloride (10.00 g, 64.5 mmol) and Boc$_2$O (28.12 g, 129 mmol) in THF (258 mL) was slowly added Et$_3$N (27 mL, 194 mmol) at room temperature. The reaction was stirred overnight, then quenched with saturated NaHCO$_3$ and brine, concentrated under vacuum and diluted with CH$_2$Cl$_2$ and brine. The mixtures were separated and the aqueous layers were extracted with CH$_2$Cl$_2$ three times, the combined organic phases were washed with brine, dried and concentrated, the residue was purified by silica gel column chromatography which gave the title compound as colourless oil (14.147 g, 86% yield).

Step b

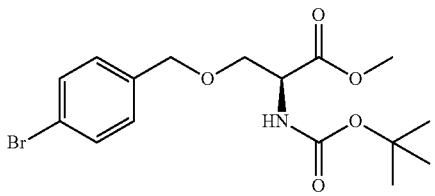

O-(4-bromo)-benzyl-boc-L-serine methyl ester (13b)

A solution of 1-bromo-4-(bromomethyl)benzene (7.5 g, 30.24 mmol) in Et$_2$O (60 ml) was added to a mixture of the compound obtained in step a above (2.27 g, 10.30 mmol) and Ag$_2$O (7.007 g, 30.24 mmol) in Et$_2$O (400 ml) at room temperature. After being stirred for 4 days, the reaction mixture was filtered through celite and washed with CH$_2$Cl$_2$, concentrated under vacuum to give crude product. The crude product was purified by silica gel column chromatography to give the title compound as colourless oil (2.567 g, 64%).

Step c

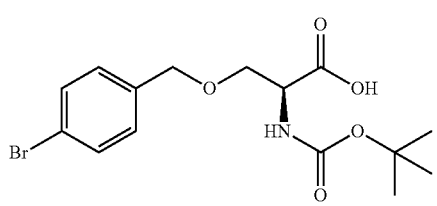

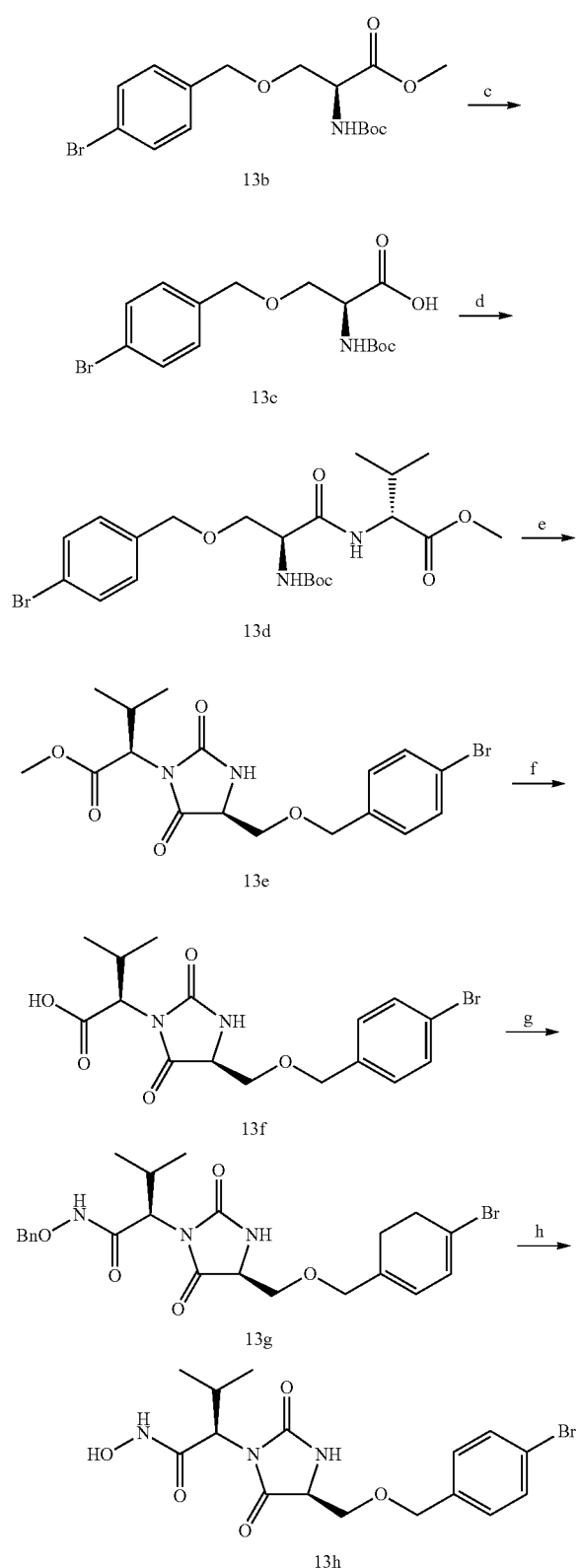

a) Boc$_2$O, Et$_3$N, THF; b) p-BrC$_6$H$_4$CH$_2$Br, Ag$_2$O, Et$_2$O; c) LiOH, THF/H$_2$O; d) (R)-methyl 2-amino-3-methylbutanoate x HCl, HOBt, EDC, NMM, DMF; e-i) TFA; e-ii) PhOC(=O)Cl, DIEA; e-iii) DIEA, DMF; f) 2M HCl; g) HOBt, EDC, NMM, BnONH$_2$; h) H$_2$, Pd/C

O-(4-bromo)-benzyl-boc-L-serine (13c)

To a solution of O-(4-bromo)-benzyl-boc-L-serine (13b) (2567 mg, 6.633 mmoL) in THF (40 mL) was added a solution of LiOH (238 mg, 9.95 mmol) in water (10 mL) at 0° C., the reaction was stirred for 5 h. 0.5 N HCl was added to neutralize, the mixture was then concentrated under vacuum. The residue was diluted with EtOAc and washed with brine. The combined organic layers were dried and concentrated; the crude product was purified by silica gel column chromatography which gave the title compound as colourless oil (2330 mg, 91%).

Step d

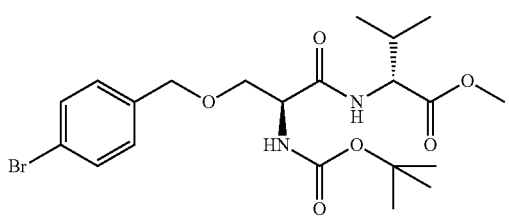

2-[3-(4-Bromobenzyloxy)-2-tert-butoxycarbonylamino]-3-methylbutyric acid methyl ester (13d)

To a mixture of the compound obtained in step c above (2.330 g, 6.25 mmol), NMM (1.5 mL, 13.4 mmol) and HOBt (1.433 g, 10.62 mmol) in DMF (15 mL) at −15° C. was added EDCl (1.017 g, 6.87 mmol). After the reaction was stirred for 30 minutes, it was allowed to warm to room temperature, (R)-methyl 2-amino-3-methylbutanoate hydrochloride (1.147 g, 6.87 mmol) was then added and the reaction was stirred overnight. The solvent was removed under vacuum; the residue was diluted with EtOAc and washed with brine. The combined organic layers were dried and concentrated; the crude product was purified by silica gel column chromatography which gave the title compound as colourless oil (2.246 g, 74%).

Step e

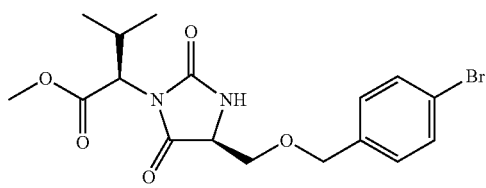

2-[4-(4-Bromobenzyloxymethyl)-2,5-dioxo-imidazolidin-1-yl]-3-methyl-butyric acid methyl ester (13e)

The compound obtained in step d above (1246 mg, 2.56 mmol) was stirred in TFA (5 mL) at 0° C. for 5 h, then concentrated under vacuum. The residue was diluted with CH$_2$Cl$_2$, washed with saturated NaHCO$_3$ and brine, dried over anhydrous Na$_2$SO$_4$, concentrated to give crude product. The obtained crude product was stirred in dioxane (9 mL) and water (1 mL) at 0° C., DIEA (990 mg, 7.68 mmol) and phenyl chloroformate (479 mg, 3.07 mmol) were added and the mixture was stirred for 2 h. The solvent was removed under vacuum; the residue was diluted with EtOAc and washed with brine. The combined organic layers were dried and concentrated to give yellow oil. The obtained oil was then stirred with DIEA (990 mg, 7.68 mmol) in DMF (10 mL) for 24 h. After general workup, the crude product was purified by silica gel column chromatography which gave the title compound as colourless oil (623 mg, 59%).

Step f

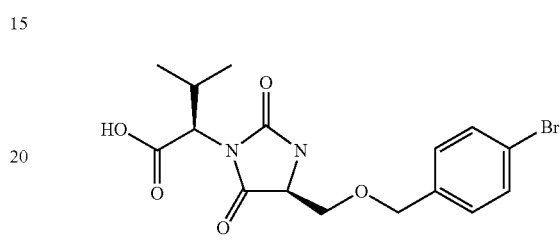

2-[4-(4-Bromobenzyloxymethyl)-2,5-dioxo-imidazolidin-1-yl]-3-methyl-butyric acid (13f)

A mixture of the compound obtained in step e above (623 mg, 1.512 mmol) and 2 N HCl (20 mL) was refluxed for 2 h. The reaction mixture was cooled down and then extracted with EtOAc. The combined organic layers were dried and concentrated; the crude product was purified by silica gel column chromatography which gave the title compound as colourless oil (409 mg, 68%).

Step q

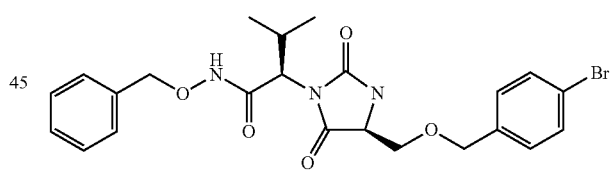

N-Benzyloxy-2-[4-(4-bromobenzyloxymethyl)-2,5-dioxo-imidazolidin-1-yl]-3-methyl-butyramide (13g)

To a mixture of the compound obtained in step f above (409 mg, 1.020 mmol), NMM (0.4 mL, 3.58 mmol) and HOBt (234 mg, 1.734 mmol) in DMF (10 mL) at −15° C. was added EDCl (214 mg, 1.123 mmol). After the reaction was stirred for 30 minutes, it was allowed to warm to room temperature, BnONH$_2$HCl (179 mg, 1.123 mmol) was then added and the reaction was stirred overnight. The solvent was removed under vacuum; the residue was diluted with EtOAc and washed with brine. The combined organic layers were dried and concentrated; the crude product was purified by silica gel column chromatography which gave the title compound as an oil (426 mg, 83% yield).

Step h

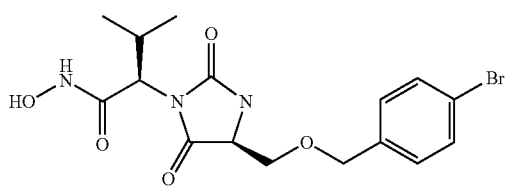

2-[4-(4-Bromobenzyloxymethyl)-2,5-dioxo-imidazolidin-1-yl]-N-hydroxy-3-methyl-butyramide (13h)

The oil obtained in step g above and 10% Pd/C (42 mg) were stirred in MeOH (15 mL) at room temperature for 2 h under $H_2$ atmosphere, the mixture was filtered through celite, washed with MeOH for several times and then concentrated. The residue was purified by silica gel column chromatography which gave the title compound as an oil (217 mg, 62% yield).
$^1$H NMR (300 MHz, $CD_3OD$): δ 0.79 (d, J=6.6 Hz, 3H), 0.97 (d, J=6.6 Hz, 3H), 2.79-2.95 (m, 1H), 3.71-3.78 (m, 1H), 3.84-3.92 (m, 1H), 4.02 (d, J=10.8 Hz, 1H), 4.18-4.22 (m, 1H), 4.61 (s, 2H), 7.48 (d, J=8.4 Hz, 2H), 7.62 (d, J=8.4 Hz, 2H).

Example 14

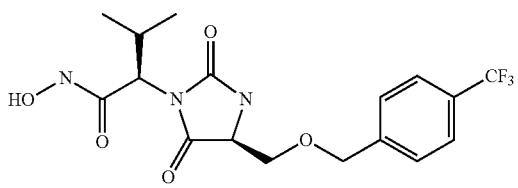

2-[2,5-Dioxo-4-(4-trifluoromethyl-bezyloxymethyl)-imidazolidin-1-yl]-N-hydroxy-3-methyl-butyramide (14)

The procedure described in method B was followed, but using 4-(trifluoromethyl)benzyl bromide instead of 4-bromobenzyl bromide, which gave the title compound (10 mg).
$^1$H-NMR (300 Hz, $CD_3OD$): δ 0.80 (m, 3H), 0.98 (m, 3H), 2.87 (m, 1H), 3.74 (m, 1H), 3.88 (m, 1H), 4.00 (m, 1H), 4.21, (m, 1H), 4.61, (m, 2H), 7.64-7.47 (m, 5H).

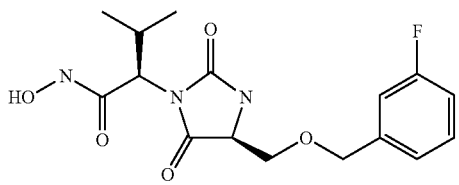

Example 15

2-[4-(3-Fluorobenzyloxymethyl)-2,5-dioxo-imidazolidin-1-yl]-N-hydroxy-3-methyl-butyramide (15)

The procedure described in method B was followed, but using 3-fluorobenzyl bromide instead of 4-bromobenzyl bromide, which gave the title compound (16 mg).
$^1$H-NMR (300 Hz, $CD_3OD$): δ 0.80 (m, 3H), 0.98 (m, 3H), 2.87 (m, 1H), 3.72 (m, 1H), 3.85 (m, 1H), 4.01 (m, 1H), 4.19, (m, 1H), 4.55, (m, 2H), 7.40-6.96 (m, 4H).

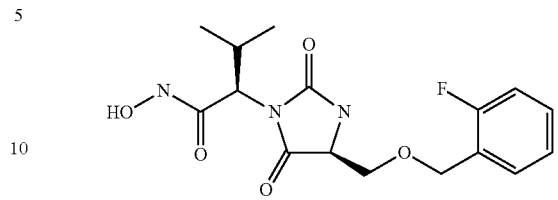

Example 16

2-[4-(2-Fluorobenzyloxymethyl)-2,5-dioxo-imidazolidin-1-yl]-N-hydroxy-3-methyl-butyramide (16)

The procedure described in method B was followed, but using 2-fluorobenzyl bromide instead of 4-bromobenzyl bromide, which gave the title compound (21 mg).
$^1$H-NMR (300 Hz, $CD_3OD$): δ 0.77 (m, 3H), 0.96 (m, 3H), 3.30 (m, 1H), 3.75 (m, 1H), 3.84 (m, 1H), 4.18 (m, 1H), 4.60, (m, 2H), 7.37-7.05 (m, 4H).

Example 17

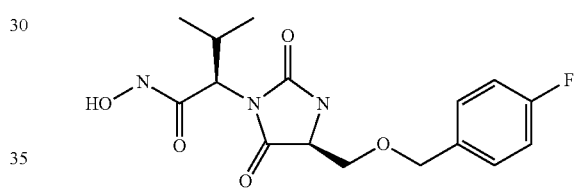

2-[4-(4-Fluorobenzyloxymethyl)-2,5-dioxo-imidazolidin-1-yl]-N-hydroxy-3-methyl-butyramide (15)

The procedure described in method B was followed, but using 4-fluorobenzyl bromideinstead of 4-bromobenzyl bromide, which gave the title compound (9 mg).
$^1$H-NMR (300 Hz, $CD_3OD$): δ 0.78 (m, 3H), 0.93 (m, 3H), 2.82 (m, 1H), 3.72 (m, 1H), 3.84 (m, 1H), 4.06 (m, 1H), 4.18, (m, 1H), 4.52, (m, 2H), 7.12-7.03 (m, 2H), 7.38-7.29 (m, 2H).

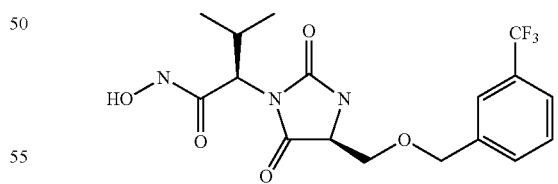

Example 18

2-[2,5-Dioxo-4-(3-trifluoromethyl-bezyloxymethyl)-imidazolidin-1-yl]-N-hydroxy-3-methyl-butyramide (18)

The procedure described in method B was followed, but using 3-(trifluoromethyl)benzyl bromide instead of 4-bromobenzyl bromide, which gave the title compound (14 mg).

¹H-NMR (300 Hz, CD₃OD): δ 0.76 (m, 3H), 0.96 (m, 3H), 2.84 (m, 1H), 3.77 (m, 1H), 3.87 (m, 1H), 4.00 (m, 1H), 4.21, (m, 1H), 4.60, (m, 2H), 7.60-7.54 (m, 4H).

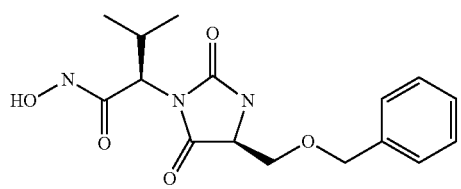

Example 19

2-(4-Benzyloxymethyl-2,5-dioxo-imidazolidin-1-yl)-N-hydroxy-3-methyl-butyramide (19)

The procedure described in method B was followed, but using benzyl bromide instead of 4-bromobenzyl bromide, which gave the title compound (11 mg).

¹H-NMR (300 Hz, CDCl₃): δ 0.83 (d, J=6.6 Hz, 3H), 1.04 (d, J=6.6 Hz, 3H), 2.61 (m, 1H), 3.75 (m, 2H), 4.22 (m, 1H), 4.32 (d, J=11.4 Hz, 1H), 4.54 (m, 2H), 7.34 (m, 5H).

Method C

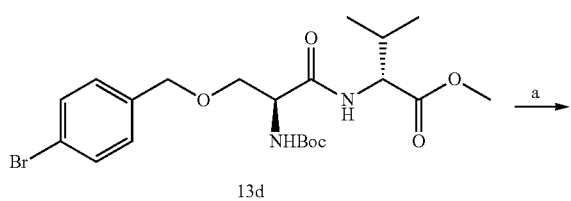

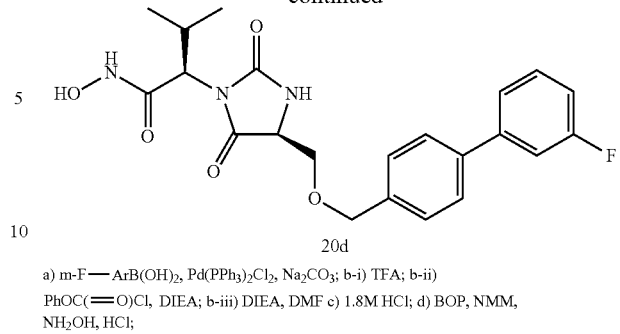

20d a) m-F—ArB(OH)₂, Pd(PPh₃)₂Cl₂, Na₂CO₃; b-i) TFA; b-ii) PhOC(=O)Cl, DIEA; b-iii) DIEA, DMF c) 1.8M HCl; d) BOP, NMM, NH₂OH, HCl;

Example 20

Step a

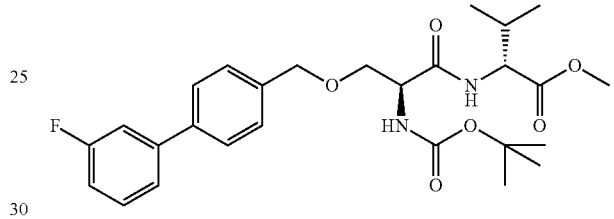

2-[2-tert-Butoxycarbonylamino-3-(3'-fluorobiphenyl-4-ylmethoxy)-propionylamino]-3-methylbutyric acid methyl ester (20a)

A mixture of the compound obtained in Example 13, step d (948 mg, 1.951 mmol), Pd (PPh₃)₂Cl₂ (136 mg, 0.1951 mmol) and 3-fluorophenylboronic acid (328 mg, 2.341 mmol) in toluene (10 mL) were stirred under an atmosphere of argon at room temperature. A solution of 2 M Na₂CO₃ aqueous (4 mL) was added and the reaction were heated to reflux for 5 h. After cooling, the reaction was diluted with EtOAc and brine, the aqueous layer was extracted with EtOAc, and the combined organic layers were dried over anhydrous NaSO₄ and concentrated. The residue was purified by silica gel column chromatography to give the title compound as a white solid (813 mg, 83%).

Step b

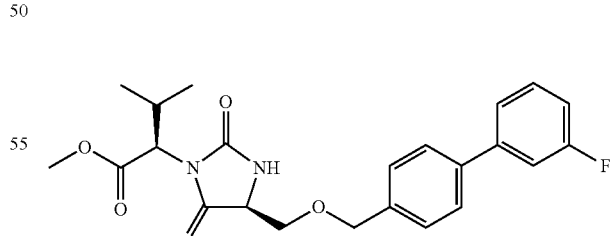

2-[4-(3'-Fluorobiphenyl-4-ylmethoxymethyl)-2,5-dioxo-imidazolidin-1-yl-3-methyl-butyric acid methyl ester (20b)

The compound obtained in step a above (20a) (813 mg, 1.619 mmol) was stirred in TFA (4 mL) at 0° C. for 5 h, then

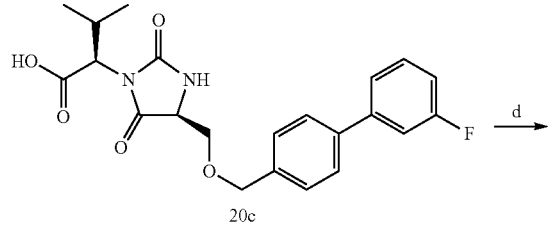

concentrated under vacuum. The residue was diluted with CH₂Cl₂, washed with saturated NaHCO₃ and brine, dried over anhydrous Na₂SO₄ and concentrated which gave the crude product. The obtained crude product was stirred in dioxane (9 mL) and water (1 mL) at 0° C. DIEA (610 mg, 4.86 mmol) and phenyl chloroformate (379 mg, 2.429 mmol) were added, and the mixture was stirred for 2 h. The solvent was removed under vacuum; the residue was diluted with EtOAc and washed with brine. The combined organic layers were dried and concentrated to give a yellow oil. The obtained oil was then stirred with DIEA (610 mg, 4.86 mmol) in DMF (10 mL) for 24 h. After general workup, the crude product was purified by silica gel column chromatography which gave the title compound as a white solid (374 mg, 54% yield).

Step c

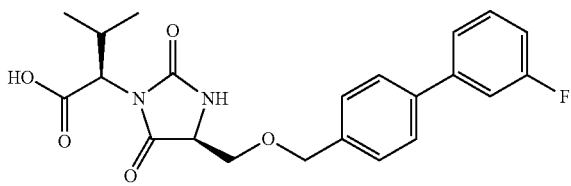

2-[4-(3'-Fluorobiphenyl-4-ylmethoxymethyl)-2,5-dioxo-imidazolidin-1-yl-3-methyl-butyric acid (20c)

A mixture of the compound obtained in step b above (20b) (374 mg, 0.874 mmol) and 2 N HCl (15 mL) was refluxed for 2 h. The reaction mixture was cooled down and then extracted with EtOAc. The combined organic layer was dried and concentrated; the crude product was purified by silica gel column chromatography to give the title compound as colorless oil (166 mg, 46%).

Step d

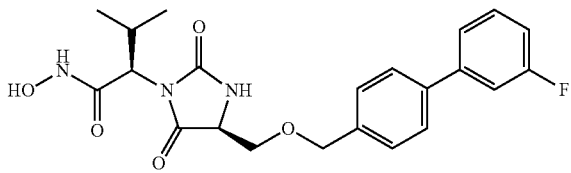

2-[4-(3'-Fluorobiphenyl-4-ylmethoxymethyl)-2,5-dioxo-imidazolidin-1-yl-N-hydroxy-3-methyl-butyramide (20d)

To a solution of the compound obtained in step c above (20c) (166 mg, 0.401 mmol) in DMF (5 mL) was added BOP reagent (213 mg, 0.481 mmol) at 0° C. After stirring for 30 min, HONH₂×HCl (50 mg, 11.38 mmol) and N-methylmorpholine (0.15 mL, 1.34 mmol) were added. The mixture was warmed to room temperature and stirred overnight. The solvent was removed and the residue was partitioned between EtOAc and saturated NH₄Cl solution. The aqueous layer was extracted with EtOAc, the organic layer was dried and concentrated. The residue was purified by silica gel column chromatography to afford the title compound as a white solid (60 mg, 35%).

¹H-NMR (300 Hz, CD₃OD): 0.82 (d, J=6.6 Hz, 3H), 0.97 (d, J=6.3 Hz, 3H), 2.82 (m, 1H), 3.76 (m, 1H), 3.84 (m, 1H), 4.03 (m, 1H), 4.20, (m, 1H), 4.58, (m, 2H), 7.61-7.58 (m, 3H), 7.45-7.37 (m, 5H).

Example 21

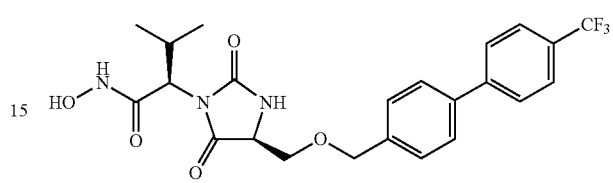

2-[2,5-Dioxo-4-(4'-trifluoromethylbiphenyl-4-yl-methoxymethyl)-imidazolidin-1-yl-N-hydroxy-3-methyl-butyramide (21)

The procedure described in method C was followed, but using 4-(trifluoromethyl)phenylboronic acid instead of 3-fluorophenylboronic acid, which gave the title compound (6 mg).

¹H-NMR (300 Hz, CD₃OD): 0.82 (m, 3H), 0.96 (m, 3H), 2.82 (m, 1H), 3.72 (m, 1H), 3.76 (m, 1H), 4.01 (m, 1H), 4.21, (m, 1H), 4.59, (m, 2H), 7.43-7.40 (m, 2H), 7.82-7.64 (m, 4H).

Method D

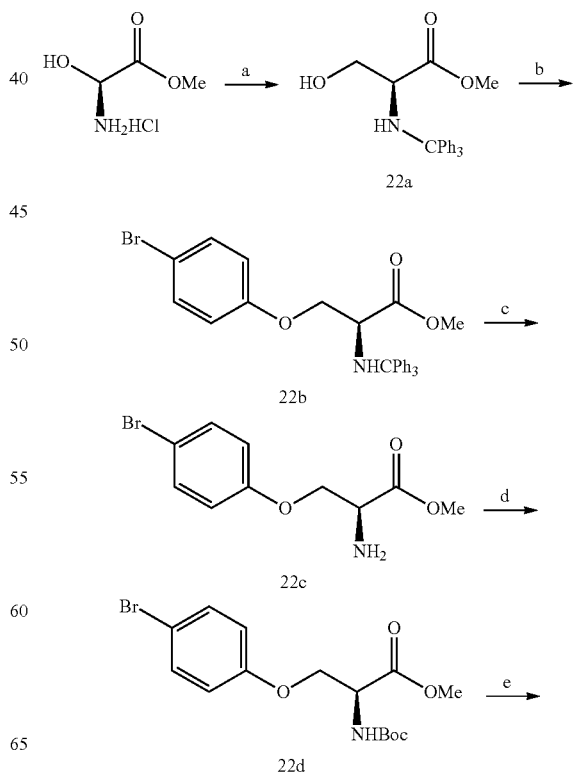

49

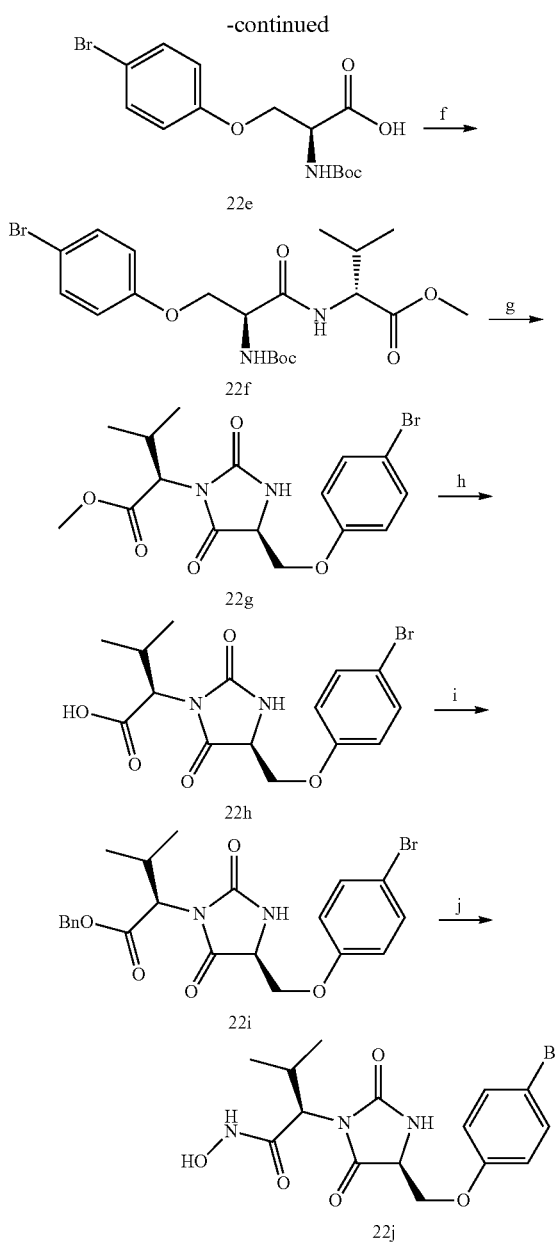

22j a) Ph₃CCl, Et₃N; b) Br—C₆H₅OH, PPh₃, DEAD; c) TFA, CH₂Cl₂; d) Boc₂O, Et₃N, DMAP, CH₂Cl₂; e) LiOH, THF/H₂O; f) (R)-methyl 2-amino-3-methylbutanoate x HCl, HOBt, EDCl, NMM, DMF; g-i) TFA; g-ii) PhOC=O)Cl, DIEA, dioxane/H₂O; g-iii) DIEA, DMF; h) 3M HCl; i) HOBt, EDC, NMM, DMF, BnONH₂HCl; j) H₂, Pd/C

Example 22

Step a

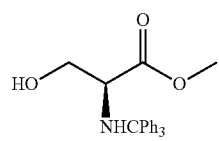

50

3-Hydroxy-2-(tritylamino)-propionic acid methyl ester (22a)

A solution of Et₃N (13.4 mL, 96.78 mmol) in CH₂Cl₂ (40 mL) was added to a solution of L-serine methyl ester hydrochloride (5.0 g, 32.26 mmol) and Ph₃CCl (13.5 g, 48.39 mmol) in CH₂Cl₂ (129 mL) at 0° C. under N₂ atmosphere. The reaction was then allowed to warm to room temperature and was stirred overnight. The reaction was quenched with saturated NaHCO₃, the aqueous layer was extracted with CH₂Cl₂, and the combined organic layers were washed with brine, dried and concentrated, the residue was purified by silica gel column chromatography which gave the title compound as a colourless solid (11.41 g, 98%).

Step b

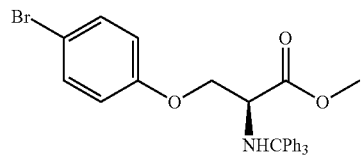

3-(4-Bromophenoxy)-2-(tritylamino)-propionic acid methyl ester (22b)

Under N₂ atmosphere, to a solution of the solid obtained in step a above (4.17 g, 11.55 mmol), PPh₃ (3.72 g, 12.71 mmol) and 4-bromophenol (2.20 g, 12.71 mmol) in toluene (25 mL) was slowly added a solution of DEAD (2.21 g, 12.71 mmol) in toluene (20%). The reaction mixture was heated to 80° C. After being stirred for 3 days, the reaction was diluted with EtOAc, the organic layer was washed with 0.3 N HCl, saturated NaHCO₃ and brine. The solvent was removed under vacuum, and the residue was purified by silica gel column chromatography to give the title compound (4.41 g, 74%).

Step c

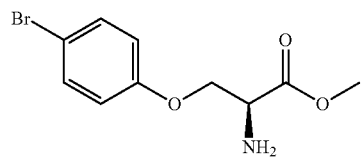

2-Amino-3-(4-bromophenoxy)-propionic acid methyl ester (22c)

The compound obtained in step b above (22b) (2.21 g, 4.10 mmol) was stirred in TFA (8 mL) and CH₂Cl₂ (10 mL) at 0° C.→rt for 1 h, the solvent was removed under vacuum. MeOH (10 mL) was added and then NaHCO₃ (344 mg, 4.10), the mixture was stirred at room temperature for 4 h and then concentrated. The residue was dissolved in CH$_2$Cl$_2$ and washed with brine, dried and concentrated to give crude title compound (1.07 g, 91%).

Step d

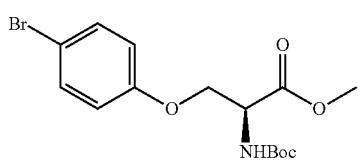

3-(4-Bromophenoxy)-2-tert-butoxycarbonylamino-propionic acid methyl ester (22d)

The crude product obtained in step c above (22c) was dissolved in CH$_2$Cl$_2$ (30 mL), a solution of Boc$_2$O (1.34 g, 6.15 mmol) in CH$_2$Cl$_2$ (10 mL) and Et$_3$N (1.15 mL, 8.20 mmol) was slowly added. After being stirred for 20 h, the reaction was quenched with saturated NaHCO$_3$; the aqueous phase was extracted with CH$_2$Cl$_2$. The combined organic layers were dried and concentrated. The residue was purified by silica gel column chromatography to give the title compound (1.32 g, 86% yield).

Step e

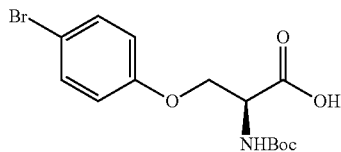

3-(4-Bromophenoxy)-2-tert-butoxycarbonylamino-propionic acid (22e)

To a solution of the compound obtained in step d above (22d) (1.087 g, 2.91 mmoL) in THF (40 mL) at 0° C. was added a solution of LiOH H$_2$O (244 mg, 5.82 mmol) in water (10 mL). After being stirred for 6 h, 0.5 N HCl (5 mL) was added and the reaction was concentrated under vacuum. The residue was diluted with EtOAc and washed with brine. The combined organic layers were dried over Na$_2$SO$_4$ and concentrated; the residue was purified by silica gel column chromatography to give the title compound as a colourless oil (816 mg, 78% yield).

Step f

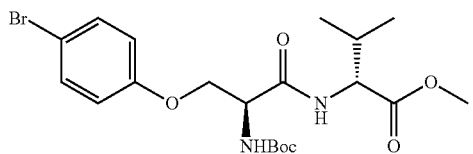

2-[3-(4-Bromophenoxy)-2-tert-butoxycarbonylamino-propionylamino]-3-methyl-butyric acid methyl ester (22f)

A solution of the compound obtained in step e above (22e) (816 mg, 2.27 mmol), NMM (0.55 mL, 4.922 mmol) and HOBt (521 mg, 3.864 mmol) in DMF (10 mL) was stirred at 0° C. for 10 minutes, then the reaction was cooled to −15° C., and EDCl (478 mg, 2.497 mmol) was added. The reaction was stirred for 30 minutes at −15° C. and then allowed to warm to room temperature, (R)-methyl 2-amino-3-methylbutanoate hydrochloride (417 mg, 2.497 mmol) was added. After being stirred overnight, the reaction mixture was concentrated under vacuum; the residue was diluted with EtOAc and washed with brine. The combined organic layers were dried and concentrated; the residue was purified by silica gel column chromatography to give the title compound as colourless oil (900 mg, 84%).

Step g

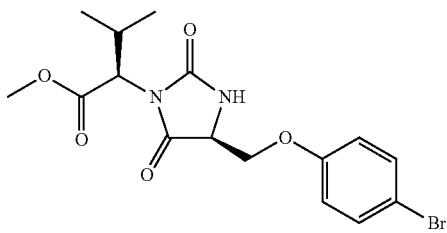

2-[4-(4-Bromophenoxymethyl)-2,5-dioxo-imidazolidin-1-yl]-3-methyl-butyric acid methyl ester (22g)

The compound obtained in step f above (22f) (900 mg, 1.907 mmol) was stirred in TFA (8 mL) at 0° C. for 5 h, and then concentrated under vacuum. The residue was diluted with CH$_2$Cl$_2$, washed with saturated NaHCO$_3$ and brine, dried over anhydrous Na$_2$SO$_4$, concentrated to give the crude product. The obtained crude product was stirred in dioxane (9 mL) and water (1 mL) at 0° C., DIEA (737 mg, 5.72 mmol) and phenyl chloroformate (446 mg, 2.861 mmol) were added, and the mixture was stirred for 1.5 h. The solvent was removed under vacuum; the residue was diluted with EtOAc and washed with brine. The combined organic layers were dried and concentrated to give a yellow oil. The obtained oil was then stirred with DIEA (737 mg, 5.72 mmol) in DMF (10 mL) for 24 h. After general workup, the crude product was purified by silica gel column chromatography to give the title compound as colorless oil (245 mg, 32% from step f).

Step h

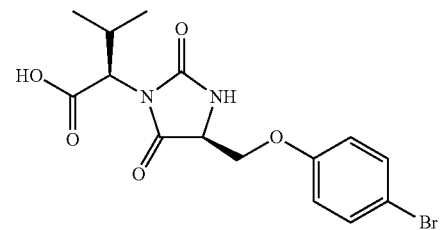

2-[4-(4-Bromophenoxymethyl)-2,5-dioxo-imidazolidin-1-yl]-3-methyl-butyric acid (22h)

A mixture of the compound obtained in step g above (22g) (759 mg, 1.907 mmol) and 3 N HCl (20 mL) was stirred at 80° C. for 2 h. The reaction mixture was cooled down and then extracted with EtOAc. The combined organic layers were dried and concentrated; the crude product was purified by silica gel column chromatography which gave the title compound as colorless oil (300 mg, 41%).

Step i

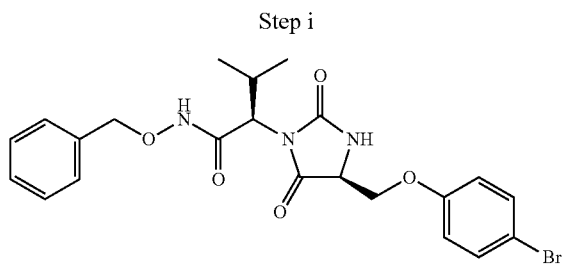

N-benzyloxy-2-[4-(4-bromophenoxymethyl)-2,5-dioxo-imidazolidin-1-yl]-3-methylbutyramide (22i)

A solution of the compound obtained in step h above (22h) (300 mg, 0.782 mmol), NMM (0.19 mL, 1.72 mmol) and HOBt (179 mg, 1.329 mmol) in DMF (11 mL) were stirred at 0° C. for 10 minutes, then the reaction was cooled to −15° C., and EDCl (165 mg, 0.860 mmol) was added. The reaction was stirred for 30 minutes at −15° C. and then allowed to warm to room temperature, BnONH$_2$HCl (137 mg, 0.860 mmol) was added. After being stirred overnight, the reaction mixture was concentrated under vacuum, and the residue was diluted with EtOAc and washed with brine. The combined organic layers were dried and concentrated; the residue was purified by silica gel column chromatography which gave the title compound as colorless oil (426 mg, 83% yield).

Step j

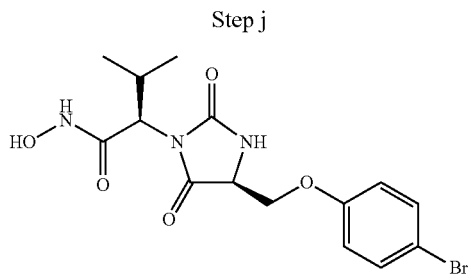

2-[4-(4-Bromophenoxymethyl)-2,5-dioxo-imidazolidin-1-yl]-N-hydroxy-3-methylbutyramide (22j)

The oil obtained in step i above (22i) (271 mg, 0.571 mmol) and 10% Pd/C (31 mg) were stirred in MeOH (25 mL) at room temperature for 3 h under H$_2$ atmosphere, the mixture was filtered through celite, washed with MeOH for several times and then concentrated. The residue was purified by silica gel column chromatography which gave the title compound as an oil (118 mg, 52% yield). % yield).

$^1$H NMR (300 MHz, CD$_3$OD): δ 0.95 (d, J=6.6 Hz, 3H), 1.02 (d, J=6.6 Hz, 3H), 2.83-3.01 (m, 1H), 4.07 (d, J=10.8 Hz, 1H), 4.23-4.29 (dd, J$_1$=2.7 Hz, J$_2$=13.5 Hz, 2H), 4.40 (s, 1H), 6.84 (d, J=9.3 Hz, 2H), 7.38 (d, J=9.3 Hz, 2H).

Example 23

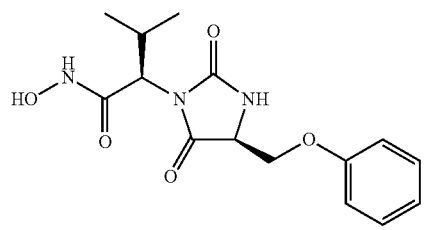

2-(2,5-Dioxo-4-phenoxymethyl-imidazolidin-1-yl)-N-hydroxy-3-methyl-butyramide (23)

The procedure described in method D was followed, but using phenol instead of 4-bromophenol, which gave the title compound (7 mg).

$^1$H-NMR (300 Hz, CD$_3$OD): 1.04-0.96 (m, 6H), 2.95 (m, 1H), 4.10 (m, 1H), 4.29-4.24 (m, 21H), 4.40 (m, 1H), 7.28-6.87 (m, 5H).

Method E

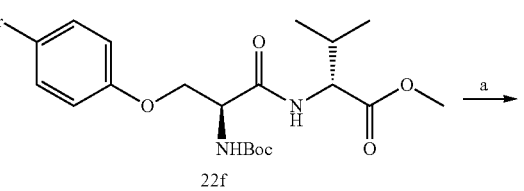

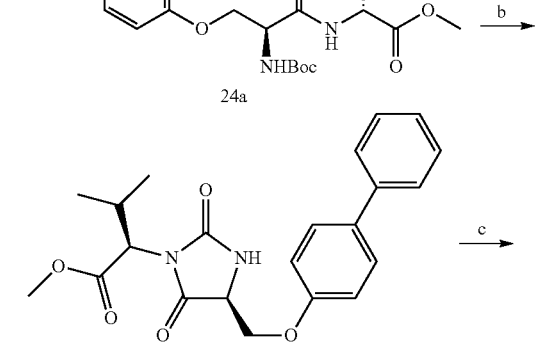

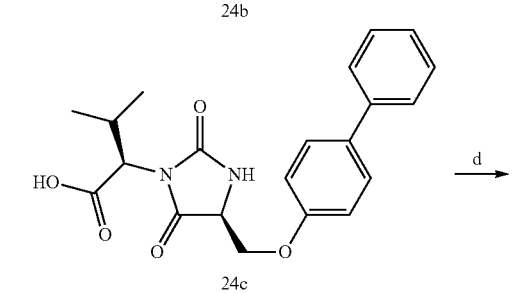

-continued

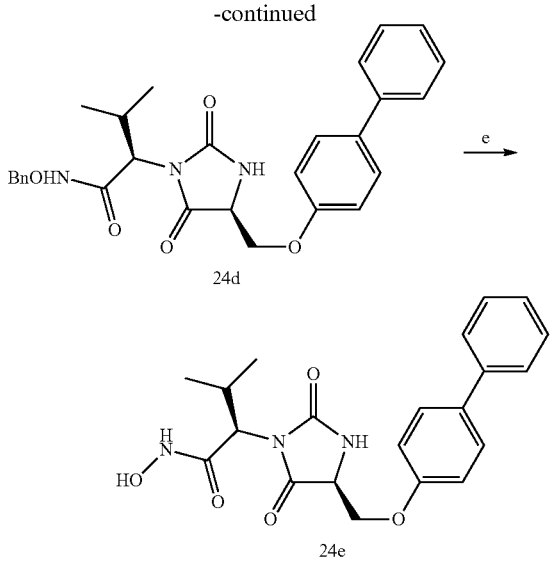

a PhB(OH)₂; b-i) TFA; b-ii) PhOC(=O)Cl, DIEA; b-iii) DIEA; c) 3M HCl; d) HOBt, EDC, NMM, BnOH₂xHCl; e) H₂, Pd/C Example 24

Step a

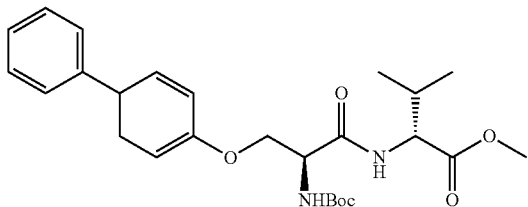

2-[2-tert-Butoxycarbonylamino-3-(4-phenyl-cyclohexa-1,5-dienyloxy)-propionylamino]-3-methylbutyric acid methyl ester (24a)

A solution of 2 M Na₂CO₃ (4 mL) was added at room temperature under an atmosphere of Argon to a mixture of the compound obtained in Example 22, step f (401 mg, 0.848 mmol), Pd(PPh₃)₂Cl₂ (154 mg, 0.22 mmol) and phenylboronic acid (145 mg, 1.1872 mmol) in toluene (10 mL) and the reaction was heated to reflux. After 5 h, the reaction was cooled to room temperature. The mixture was diluted with EtOAc, and washed with brine. The combined organic layers were dried over anhydrous NaSO₄ and concentrated under vacuum. The residue was purified by silica gel column chromatography which gave the title compound as a white solid (255 mg, 64%).

Step b

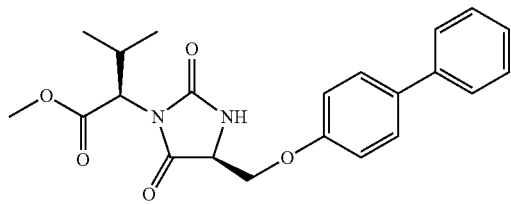

2-[4-(Biphenyl-4-yloxymethyl)-(2,5-dioxo-imidazolidin-1-yl]-3-methyl-butyric acid methyl ester (24b)

The compound obtained in step a (24a) above (764 mg, 1.626 mmol) was stirred in TFA (10 mL) at 0° C. for 5 h, then concentrated under vacuum. The residue was diluted with CH₂Cl₂, washed with saturated NaHCO₃ and brine, dried over anhydrous Na₂SO₄ and concentrated which gave the crude product. The obtained crude product was stirred in dioxane (9 mL) and water (1 mL) at 0° C., DIEA (629 mg, 4.878 mmol) and phenyl chloroformate (382 mg, 2.43 mmol) were added, and the mixture was stirred for 2 h. The solvent was removed under vacuum; the residue was diluted with EtOAc and washed with brine. The combined organic layers were dried and concentrated to give a yellow oil. The obtained oil was then stirred with DIEA (629 mg, 4.878 mmol) in DMF (10 mL) for 30 h. After general workup, the crude product was purified by silica gel column chromatography which gave the title compound as colourless oil (328 mg, 51%).

Step c

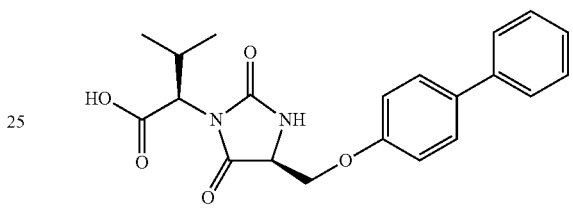

2-[4-(Biphenyl-4-yloxymethyl)-(2,5-dioxo-imidazolidin-1-yl]-3-methyl-butyric acid (24c)

A mixture of the compound obtained in step b above (24b) (320 mg, 0.808 mmol) and 3 N HCl (15 mL) was stirred at 80° C. for 4 h. The reaction mixture was cooled down and then extracted with EtOAc. The combined organic layers were dried and concentrated; the crude product was purified by silica gel column chromatography which gave the title compound as colourless oil (96 mg, 31%).

Step d

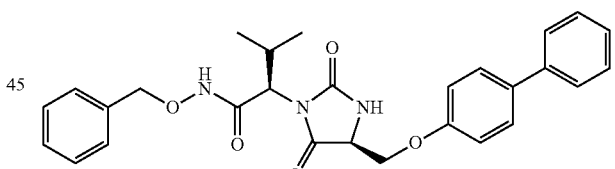

N-Benzyloxy-2-[4-(biphenyl-4-yloxymethyl)-(2,5-dioxo-imidazolidin-1-yl]-3-methylbutyramide (24d)

A solution of the compound obtained in step c above (96 mg, 0.250 mmol), NMM (0.05 mL, 0.448 mmol) and HOBt (58 mg, 0.426 mmol) in DMF (6 mL) were stirred at 0° C. for 10 minutes, then the reaction was cooled to −15° C., and EDCl (53 mg, 0.275 mmol) was added. The reaction was stirred for 30 minutes at −15° C. and then allowed to warm to room temperature, BnONH₂HCl (44 mg, 0.275 mmol) was added. After being stirred overnight, the reaction mixture was concentrated under vacuum, the residue was diluted with EtOAc and washed with brine. The combined organic layers were dried and concentrated, the residue was purified by silica gel column chromatography which gave the title compound as colourless oil (92 mg, 76%).

Step e

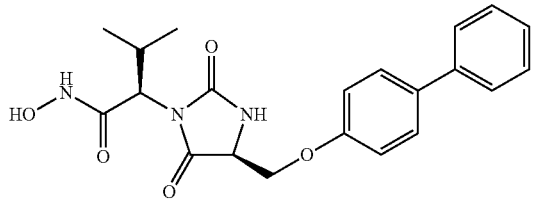

2-[4-(Biphenyl-4-yloxymethyl)-(2,5-dioxo-imidazolidin-1-yl]-N-hydroxy-3-methylbutyramide (24e)

The oil obtained in step d above (24d) (90 mg, 0.185 mmol) and 10% Pd/C (12 mg) were stirred in MeOH (15 mL) at room temperature for 3 h under $H_2$ atmosphere. The mixture was filtered through celite, washed with MeOH several times and then concentrated. The residue was purified by silica gel column chromatography which gave the title compound as an oil (32 mg, 44%).

$^1$H NMR (300 MHz, $CD_3OD$): δ 0.99 (d, J=6.6 Hz, 3H), 1.04 (d, J=6.6 Hz, 3H), 2.82-2.98 (m, 1H), 4.11 (d, J=10.8 Hz, 1H), 4.25-4.40 (m, 2H), 4.43 (s, 1H), 6.98 (d, 2H), 7.22-7.42 (m, 3H), 7.50-7.58 (m, 4H).

Method F

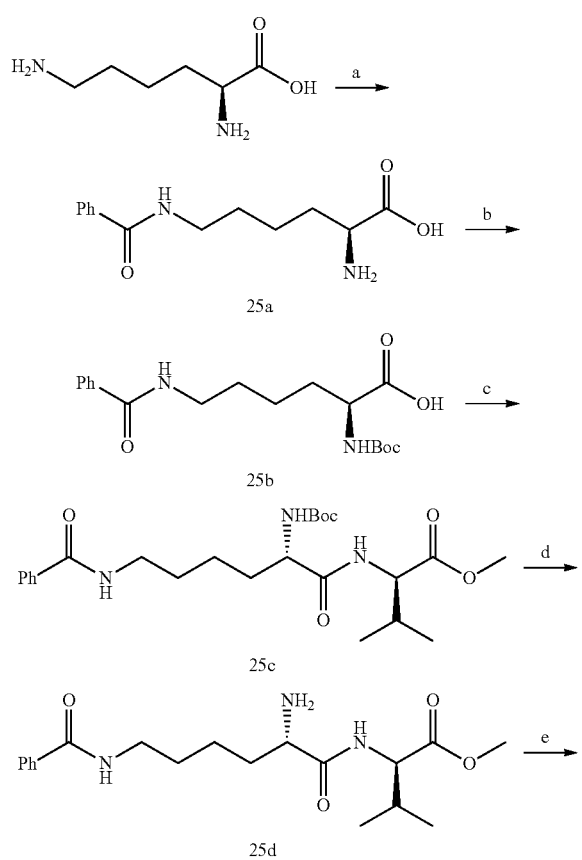

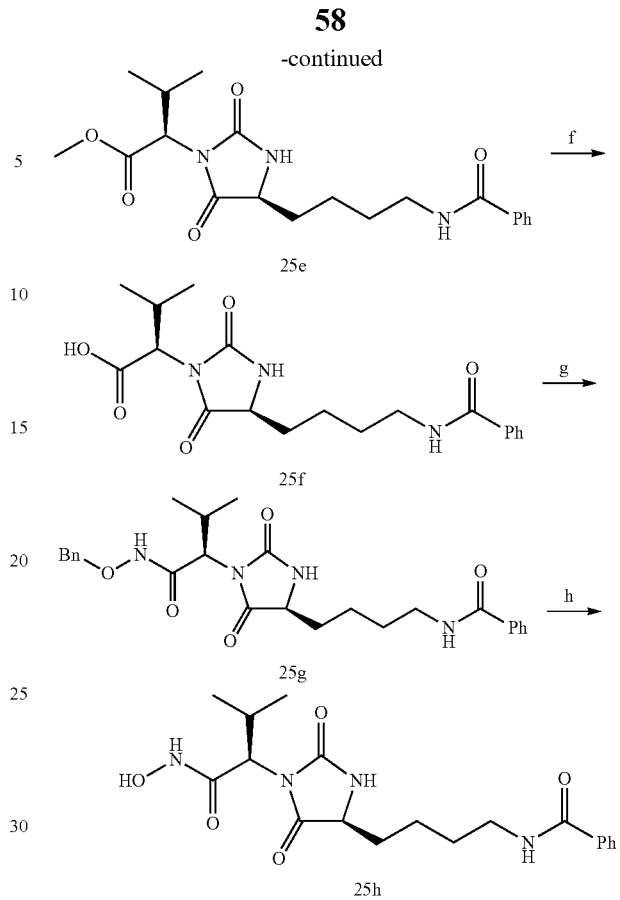

a-i) $CuCO_3$, $H_2O$; a-ii) PhC(=O)Cl, NaOH, $H_2O$; a-iii) EDTA, $H_2O$;
b) $Boc_2O$, $Et_3N$, dioxane/$H_2O$; c) (R)-methyl 2-amino-3-methylbutanoate hydrochloride, HOBt, EDC, $NaHCO_3$; d) $HCO_2H$, e-i) PhOC(=O)Cl, DIEA; e-ii) DIEA, DMF; f) 6M HCl; g) $BnOH_2xHCl$, HOBt, EDC, NMM, DMF; h) $H_2$, Pd/C

Example 25

Step a

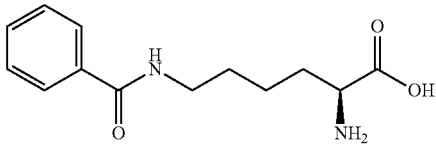

2-Amino-6-benzoylamino-hexanoic acid (25a)

To a solution of L-lysine (1) (3.65 g, 0.02 mol) in water (50 mL) at 90° C. was added $CuCO_3$ (2.5 g) portionwise. After being refluxed for 40 min, the mixture was cooled and filtered. The filtrate was further cooled to 0° C., and a solution of BzCl (3.5 mL, 0.03 mol) and NaOH (2.7 g, 0.0685 mol) in water (20 mL) were added. The reaction was stirred at 0° C. for 1 h and then allowed to warm to room temperature. After 2 days, the reaction mixture was filtered and the solid was washed with water and $Et_2O$. This obtained solid was then added to a solution of EDTA (7.0 g) in water (350 mL), the mixture was heated to reflux until the reaction solution became clear blue. The reaction was cooled which gave a white precipitate. This precipitate was collected and washed with water and Et$_2$O and dried which afforded the title compound as a white solid (1.8 g, 36%).

Step b

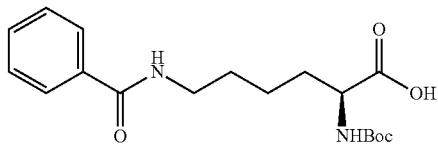

6-Benzoylamino-2-tert-butoxycarbonylamino-hexanoic acid (25b)

To a solution of the compound obtained in step a above (1.0 g, 4.0 mmol) Et$_3$N (0.92 mL, 6.6 mmol) and dioxane/H$_2$O (1:1, v/v) (40 mL) at 0° C. was added Boc$_2$O (0.96 g, 4.4 mmol). The reaction was allowed to warm to room temperature and stirred overnight. The solvent was removed and the residue was partitioned between water and EtOAc. The aqueous layer was acidified and extracted with EtOAc, and the combined organic phases were dried over anhydrous Na$_2$SO$_4$. After concentration under vacuum, the crude title compound (1.4 g) was obtained and used in the next reaction without further purification.

Step c

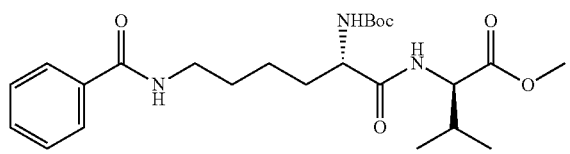

6-Benzoylamino-2-tert-butoxycarbonylamino-hexanoylamino)-3-methyl-butyric acid methyl ester (25c)

EDCl (1.26 g, 6.6 mmol) was added at −15° C. to a mixture of the compound obtained in step b above (25b) (1.0 g, 3.0 mmol), NaHCO$_3$ (0.83 g, 9.8 mmol) and HOBt (1.15 g, 7.5 mmol) in DMF (30 mL). The reaction was stirred for 30 minutes, and then it was allowed to warm to room temperature. (R)-Methyl 2-amino-3-methylbutanoate hydrochloride (0.58 g, 3.3 mmol) was then added and the reaction was stirred overnight. The solvent was removed under vacuum; the residue was diluted with EtOAc and washed with brine. The combined organic layers were dried and concentrated; the crude product was purified by silica gel column chromatography which gave the title compound as a white solid (1.1 g, 79%).

Step d

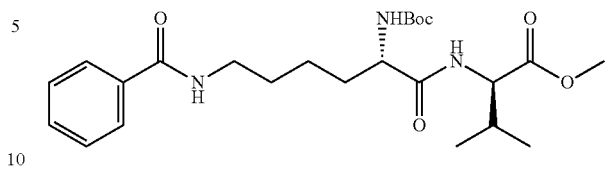

2-(2-Amino-6-benzoylamino-hexanoylamino)-3-methyl-butyric acid methyl ester (25d)

A mixture of the compound obtained in step c above (1.0 g, 2.1 mmol) and HCO$_2$H (20 mL) in CHCl$_3$ (15 mL) was stirred at room temperature overnight. The reaction was diluted with CH$_2$Cl$_2$ and NaHCO$_3$ was added to adjust the pH to 8. The organic layer was washed with brine, dried and concentrated to give crude title compound as a colorless oil (0.6 g, 78% yield).

Step e

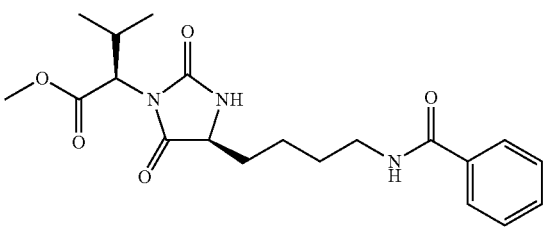

2-[4-(Benzoylamino-butyl)-(2,5-dioxo-imidazolidin-1-yl]-3-methyl-butyric acid methyl ester (25e)

To a mixture of the crude compound obtained in step d above (25d) (0.6 g, 1.65 mmol) in dioxane (18 mL) and water (2 mL) was added phenyl chloroformate (0.21 mL, 1.65 mmol) and DIEA (0.6 mL, 3.3 mmol). The mixture was stirred at room temperature for 3 h and concentrated under reduced pressure. The residue was partitioned between water and EtOAc. The aqueous layer was extracted with EtOAc, the combined organic phases were dried and concentrated which gave a white solid (0.79 g). This white solid was dissolved in DMF (20 mL), and DIEA (0.28 mL, 1.6 mmol) was added. After stirring overnight at room temperature, the solvent was removed. The residue was diluted with EtOAc and washed with water. The organic layer was dried and concentrated under reduced pressure. The residue was purified by silica gel column chromatography which afforded the title compound as a colorless oil (0.43 g, 69%).

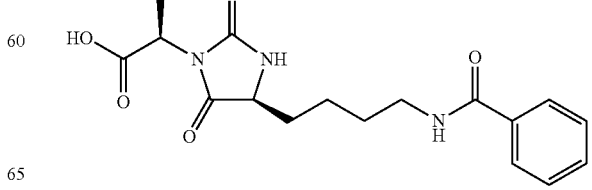

Step f

2-[4-(Benzoylamino-butyl)-(2,5-dioxo-imidazolidin-1-yl]-3-methyl-butyric acid (25f)

A mixture of the compound obtained in step e above (25f) (0.21 g, 0.54 mmol) and 6 N HCl (5 mL) was heated at 70° C. for 6 h. The reaction was diluted with water and extracted with CH$_2$Cl$_2$. The organic layer was washed with brine, dried over Na$_2$SO$_4$, and concentrated under vacuum which gave the title compound as a crude oil (0.2 g, 98%).

Step g

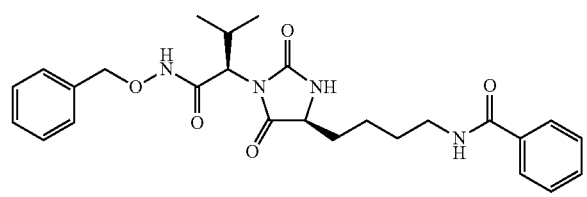

N-{4-[1-(1-Benzyloxycarbamoyl-2-methyl-propyl)-(2,5-dioxo-imidazolidin-4-yl]-butyl}-benzamide (25g)

A solution of the compound obtained in step f above (25f) (200 mg, 0.53 mmol), NMM (0.15 mL, 1.3 mmol) and HOBt (98 mg, 0.64 mmol) in DMF (5 mL) was stirred at 0° C. for 15 minutes, then the reaction was cooled to −15° C., and EDCI (123 mg, 0.64 mmol) was added. The reaction was stirred for 30 minutes at −15° C. and then allowed to warm to room temperature and BnONH$_2$HCl (102 mg, 0.64 mmol) was added. After being stirred overnight, the reaction mixture was concentrated under vacuum; the residue was diluted with EtOAc and washed with brine. The combined organic layers were dried and concentrated, the residue was purified by silica gel column chromatography which gave the title compound as a white solid (150 mg, 59%).

Step h

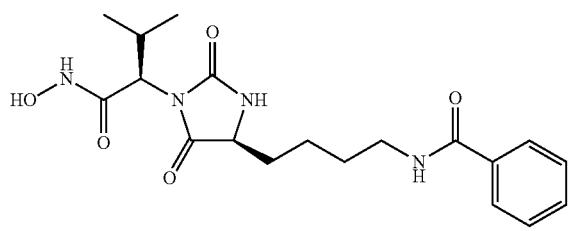

N-{4-[1-(1-Hydroxycarbamoyl-2-methyl-propyl)-(2,5-dioxo-imidazolidin-4-yl]-butyl}-benzamide (25h)

The compound obtained in step g above (25g) (150 mg, 0.312 mmol) and 10% Pd/C (20 mg) were stirred in MeOH (10 mL) at room temperature for 15 h under H$_2$ atmosphere, the mixture was filtered through celite, washed with MeOH several times and then concentrated. The residue was purified by silica gel column chromatography which gave the title compound as a white solid (50 mg, 41%).

$^1$H NMR (300 MHz, CD$_3$OD+CDCl$_3$): δ 0.86 (d, 3H, J=6.9 Hz,), 1.02 (d, 2H, J=6.9 Hz), 1.46-1.91 (m, 6H), 2.83-2.86 (m, 1H), 3.34-3.42 (m, 2H), 4.04-4.08 (m, 2H), 7.41-7.82 (m, 5H).

Example 26

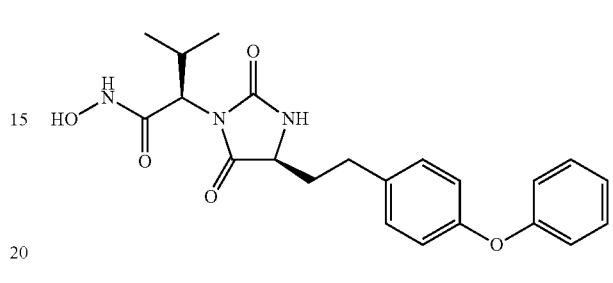

2-{2,5-Dioxo-4-[2-(4-phenoxyphenyl)-ethyl]-imidazolidin-1-yl}-N-hydroxy-3-methyl-butyramide (26)

The procedure described in method A was followed but using 2-tert-butoxycaronylamino-4-(4-phenyoxyphenyl)-butyric acid instead of N-boc-homophenylalanine which gave the title compound (8 mg).

$^1$H NMR (300 MHz, CDCl$_3$): δ 0.82-1.02 (dd, J$_1$=6.3 Hz, J$_2$=53.4 Hz, 6H), 1.90-2.30 (m, 2H), 2.60-2.80 (m, 3H), 4.00-4.08 (m, 1H), 4.19-4.24 (d, J=10.8 Hz, 1H), 6.59 (s, 1H), 6.91-6.99 (m, 4H), 7.05-7.4-0 (m, 5H).

Example 27

Preparation of Substituted N-Boc-L-Homophenylalanine Derivatives

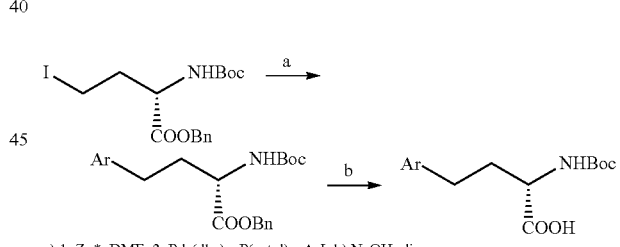

a) 1. Zn*, DMF; 2. Pd$_2$(dba)$_3$, P(o-tol)$_3$, ArI; b) NaOH, dioxane

Step a

A series of substituted homophenylalanine derivatives were synthesized by coupling of the corresponding substituted aryl iodide to 2-tert-butoxy-carbonylamino-4-iodobutyric acid according to the procedure described in J. Org. Chem. 1998, 63, 7875.

Step b

To a solution of the compound obtained in step a above in 1,4-dioxane was added 2N NaOH. After stirring at room temperature for 3 h, the reaction was diluted with EtOAc. The mixture was acidified by slow addition of 1N HCl to PH 6, and then extracted with EtOAc. The organic phases were washed with brine, dried and concentrated. The residue was purified by silica gel column chromatography to afford the acid derivatives 27a-27m.

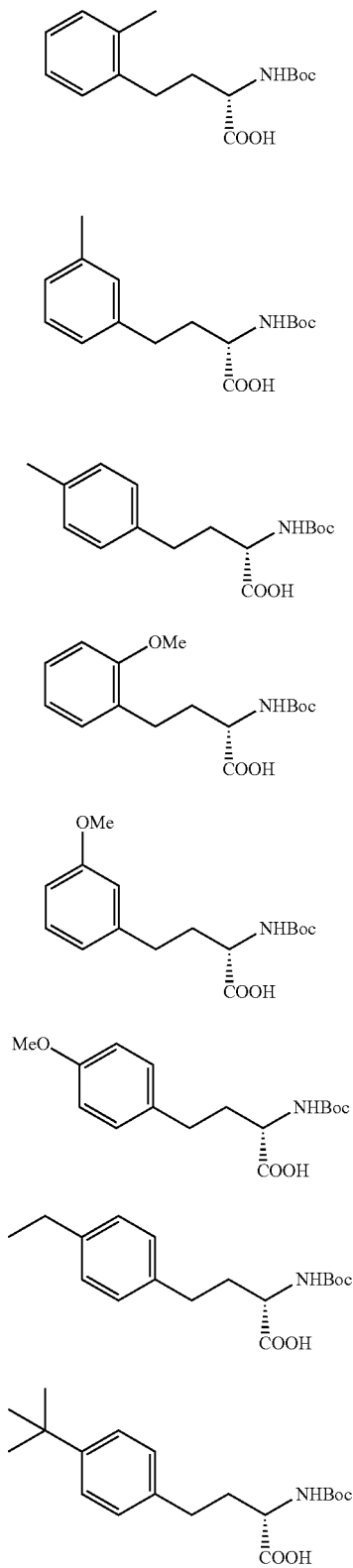

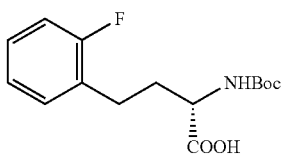

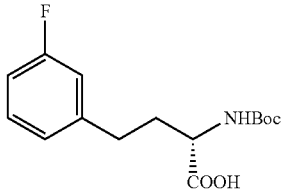

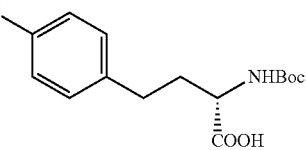

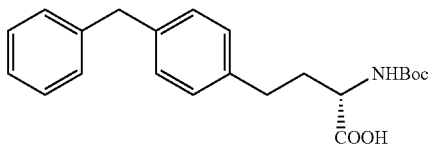

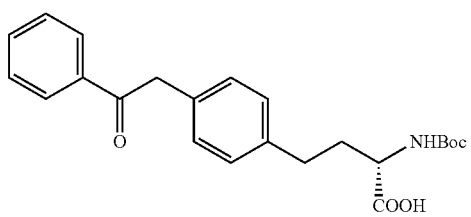

Example 28

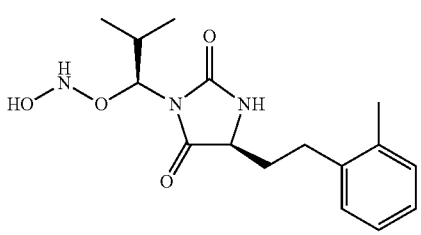

2-[2,5-Dioxo-4-(2-o-tolylethyl)-imidazolidin-1-yl]-N-hydroxy-3-methyl-butyramide (28)

The procedure described in method A was followed but using 27a instead of N-boc-L-homophenylalanine which gave the title compound (8 mg).

$^1$H NMR (300 MHz, CDCl$_3$): δ 0.90 (d, J=6.6 Hz, 3H), 1.12 (d, J=6.6 Hz, 3H), 1.91-2.03 (m, 1H), 2.07-2.23 (m, 1H), 2.29 (s, 3H), 2.60-2.80 (m, 3H), 4.09-4.16 (m, 1H), 4.37 (d, J=8.7 Hz, 1H), 6.78 (s, 1H), 7.13 (m, 4H).

Example 29

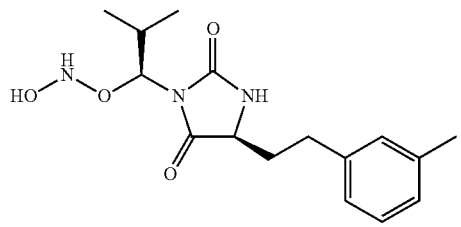

2-[2,5-Dioxo-4-(2-m-tolylethyl)-imidazolidin-1-yl]-N-hydroxy-3-methyl-butyramide (29)

The procedure described in method A was followed but using 27b instead of N-boc-L-homophenylalanine which gave the title compound (13 mg).

$^1$H NMR (300 MHz, CDCl$_3$): δ 0.83 (d, J=6.6 Hz, 3H), 1.01 (d, J=6.6 Hz, 3H), 1.90-2.01 (m, 1H), 2.21-2.29 (m, 1H), 2.32 (s, 3H), 2.62-2.76 (m, 3H), 4.02-4.04 (m, 1H), 4.21 (d, J=11.4 Hz, 1H), 6.52 (s, 1H), 6.98-7.05 (m, 3H), 7.17-7.27 (m, 1H), 8.32 (s, br, 1H), 10.11 (s, 1H).

Example 30

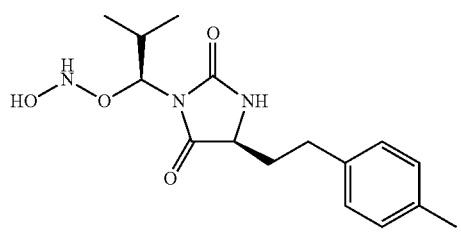

2-[2,5-Dioxo-4-(2-p-tolylethyl)-imidazolidin-1-yl]-N-hydroxy-3-methyl-butyramide (30)

The procedure described in method A was followed but using 27c instead of N-boc-L-homophenylalanine which gave the title compound (12 mg).

$^1$H NMR (300 MHz, CD$_3$OD): δ 0.88 (d, J=6.6 Hz, 3H), 1.01 (d, J=6.6 Hz, 3H), 1.86-1.93 (m, 1H), 2.04-2.09 (m, 1H), 2.28 (s, 3H), 2.66 (t, J=7.8 Hz, 2H), 2.86-2.92 (m, 1H), 4.01-4.06 (m, 2H), 7.08 (s, 4H).

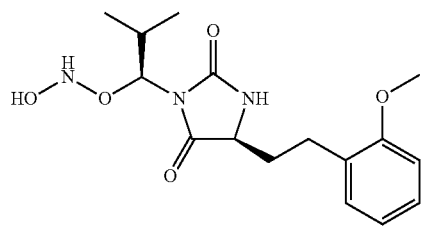

Example 31

N-Hydroxy-2-{4-[2-(2-methoxyphenyl)-ethyl]-2,5-dioxo-imidazolidin-1-yl}-3-methyl-butyramide (31)

The procedure described in method A was followed but using 27d instead of N-boc-L-homophenylalanine which gave the title compound (11 mg).

$^1$H NMR (300 MHz, CD$_3$OD): δ 0.89 (d, J=6.6 Hz, 3H), 1.04 (d, J=6.6 Hz, 3H), 1.84-1.97 (m, 1H), 2.09-2.21 (m, 1H), 2.72-2.91 (m, 3H), 3.84 (s, 3H), 3.97-4.01 (m, 1H), 4.08 (d, J=10.8 Hz, 1H), 6.87-6.91 (m, 2H), 7.14-7.23 (m, 2H), 7.58 (s, 1H).

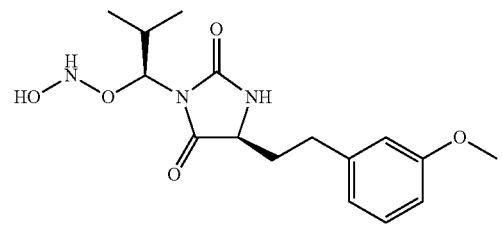

Example 32

N-Hydroxy-2-{4-[2-(3-methoxyphenyl)-ethyl]-2,5-dioxoimidazolidin-1-yl}-3-methylbutyramide (32)

The procedure described in method A was followed but using 27e instead of N-boc-L-homophenylalanine which gave the title compound (8 mg).

$^1$H NMR (300 MHz, CD$_3$OD): δ 0.91 (d, J=6.6 Hz, 3H), 1.04 (d, J=6.6 Hz, 3H), 1.91-1.98 (m, 1H), 2.09-2.14 (m, 1H), 2.71 (t, J=8.1 Hz, 2H), 2.91-2.95 (m, 1H), 3.79 (s, 3H), 4.05-4.09 (m, 2H), 6.76-6.82 (m, 3H), 7.18-7.23 (m, 1H).

Example 33

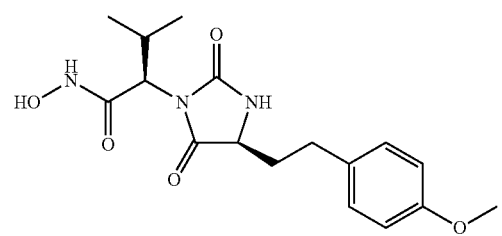

N-Hydroxy-2-{4-[2-(4-methoxyphenyl)-ethyl]-2,5-dioxoimidazolidin-1-yl}-3-methylbutyramide (33)

The procedure described in method A was followed but using 27f instead of N-boc-L-homophenylalanine which gave the title compound (11 mg).

$^1$H NMR (300 MHz, CD$_3$OD): δ 0.91 (d, J=6.6 Hz, 3H), 1.04 (d, J=6.6 Hz, 3H), 1.88-1.95 (m, 1H), 2.04-2.11 (m, 1H), 2.68 (t, J=8.1 Hz, 2H), 2.90-2.98 (m, 1H), 3.78 (s, 3H), 4.06-4.09 (m, 2H), 6.86 (d, J=8.1 Hz, 2H), 7.15 (d, J=8.1 Hz, 2H).

Example 34

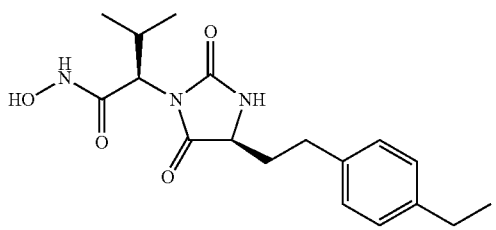

2-{4-[2-(4-Ethylphenyl)-ethyl]-2,5-dioxoimidazolidin-1-yl}-N-hydroxy-3-methyl-butyramide (34)

The procedure described in method A was followed but using 27g instead of N-boc-L-homophenylalanine which gave the title compound (14 mg).

¹H NMR (300 MHz, CDCl₃): δ 0.82 (d, J=6.6 Hz, 3H), 1.00 (d, J=6.6 Hz, 3H), 1.21 (t, J=7.5 Hz, 3H), 1.90-2.03 (m, 1H), 2.21-2.27 (m, 1H), 2.61 (q, J=7.5 Hz, 2H), 2.68-2.76 (m, 3H), 4.03 (s, br, 1H), 4.22 (d, J=11.4 Hz, 1H), 6.42 (s, 1H), 7.10-7.26 (m, 4H), 8.24 (s, br, 1H), 10.09 (s, br, 1H).

Example 35

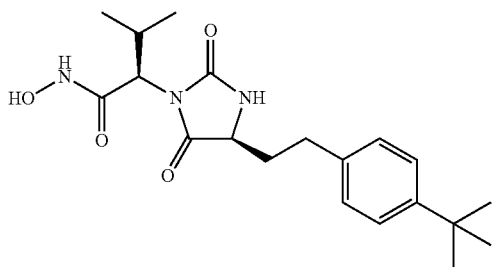

2-{4-[2-(4-tert-Butylphenyl)-ethyl]-2,5-dioxoimidazolidin-1-yl}-N-hydroxy-3-methylbutyramid (35)

The procedure described in method A was followed but using 27h instead of N-boc-L-homophenylalanine which gave the title compound (13 mg).

¹H NMR (300 MHz, CDCl₃): δ 0.82 (d, J=6.3 Hz, 3H), 1.00 (d, J=6.3 Hz, 3H), 1.29 (s, 9H), 1.90-2.04 (m, 1H), 2.20 (m, 1H), 2.62-2.73 (m, 3H), 4.05-4.10 (m, 1H), 4.18-4.28 (m, 1H), 6.64 (s, 1H), 7.12 (d, J=8.1 Hz, 2H), 7.31 (d, J=8.1 Hz, 2H), 8.35 (s, br, 1H), 10.12 (s, br, 1H).

Example 36

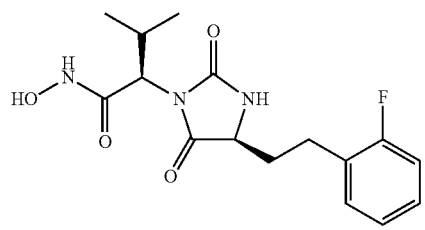

2-{4-[2-(2-Fluorophenyl)-ethyl]-2,5-dioxoimidazolidin-1-yl}-N-hydroxy-3-methylbutyramide (36)

The procedure described in method A was followed but using 27i instead of N-boc-L-homophenylalanine which gave the title compound (7 mg).

¹H NMR (300 MHz, CD₃OD): δ 0.91 (d, J=6.6 Hz, 3H), 1.04 (d, J=6.6 Hz, 3H), 1.91-2.02 (m, 1H), 2.05-2.13 (m, 1H), 2.75-2.81 (m, 2H), 2.90-2.98 (m, 1H), 4.06-4.13 (m, 2H), 7.03-7.14 (m, 2H), 7.21-7.29 (m, 2H).

Example 37

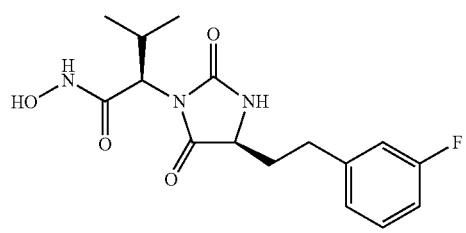

2-{4-[2-(3-Fluoro-phenyl)-ethyl]-2,5-dioxoimidazolidin-1-yl}-N-hydroxy-3-methylbutyramide (37)

The procedure described in method A was followed but using 27j instead of N-boc-L-homophenylalanine which gave the title compound (15 mg).

¹H NMR (300 MHz, CD₃OD): δ 0.87 (d, J=6.9 Hz, 3H), 1.00 (d, J=6.9 Hz, 3H), 1.88-1.96 (m, 1H), 2.06-2.10 (m, 1H), 2.71 (t, J=8.1 Hz, 2H), 2.86-2.92 (m, 1H), 4.01-4.06 (m, 2H), 6.87-7.03 (m, 3H), 7.24-7.29 (m, 1H).

Example 38

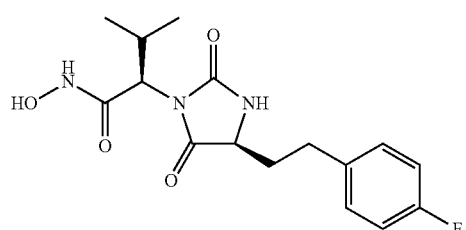

2-{4-[2-(4-Fluoro-phenyl)-ethyl]-2,5-dioxoimidazolidin-1-yl}-N-hydroxy-3-methylbutyramide (38)

The procedure described in method A was followed but using 27k instead of N-boc-L-homophenylalanine which gave the title compound (11 mg).

$^1$H NMR (300 MHz, CD$_3$OD): δ 0.88 (d, J=6.9 Hz, 3H), 1.01 (d, J=6.9 Hz, 3H), 1.91-1.95 (m, 1H), 2.05-2.10 (m, 1H), 2.70 (t, J=7.8 Hz, 2H), 2.89-2.93 (m, 1H), 4.03-4.06 (m, 2H), 6.97-7.03 (m, 2H), 7.20-7.24 (m, 2H).

Example 39

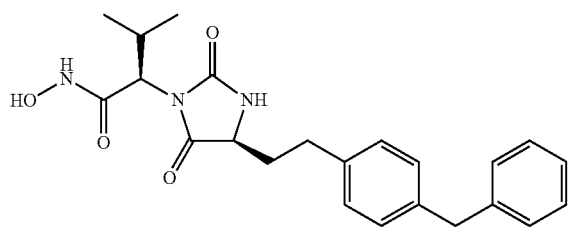

2-{4-[2-(4-Benzylphenyl)-ethyl]-2,5-dioxoimidazolidin-1-yl}-N-hydroxy-3-methylbutyramide (39)

The procedure described in method A was followed but using 27l instead of N-boc-L-homophenylalanine which gave the title compound (12 mg).

$^1$H NMR (300 MHz, CDCl$_3$): δ 0.82 (d, J=6.6 Hz, 3H), 1.01 (d, J=6.6 Hz, 3H), 1.88-2.00 (m, 1H), 2.15-2.28 (m, 1H), 2.60-2.76 (m, 3H), 3.95 (s, 2H), 4.00-4.04 (m, 1H), 4.22 (d, J=11.7 Hz, 1H), 6.23 (s, 1H), 7.12-7.31 (m, 9H), 8.12 s, br, 1H), 10.10 (s, 1H).

Example 40

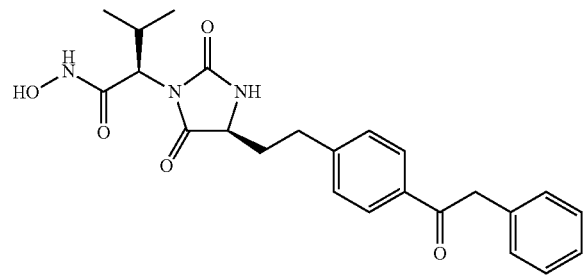

2-{2,5-Dioxo-4-[2-(4-phenylacetyl-phenyl)-ethyl]-imidazolidin-1-yl}-N-hydroxy-3-methylbutyramide (40)

The procedure described in method A was followed but using 27m instead of N-Boc-L-homophenylalanine which gave the title compound (7 mg.)

$^1$H NMR (300 MHz, CD$_3$OD): δ 0.91 (d, J=6.6 Hz, 3H), 1.04 (d, J=6.6 Hz, 3H), 1.98-2.03 (m, 1H), 2.12-2.16 (m, 1H), 2.78-2.83 (m, 2H), 2.91-2.95 (m, 1H), 4.05-4.11 (m, 2H), 4.33 (s, 2H), 7.23-7.38 (m, 7H), 8.01 (d, J=7.8 Hz, 2H).

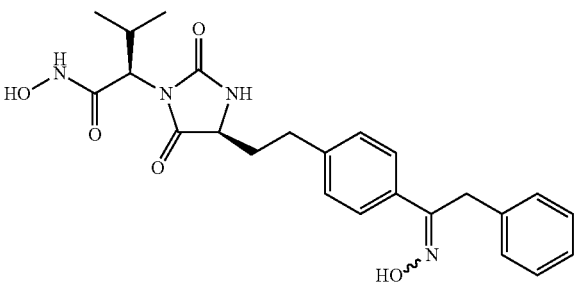

Example 41

N-Hydroxy-2-(4-{2-[4-(1-hydroxyimino-2-phenyl-ethyl)-phenyl]-ethyl}-2,5-dioxoimidazolidin-1-yl)-3-methylbutyramide (41)

To a solution compound 40 (140 mg, 0.32 mmol) in CHCl$_3$/CH$_3$OH (10 mL) was added HONH$_2$×HCl (44 mg, 0.64 mmol) and N-methylmorpholine (0.071 mL, 0.64 mmol). After stirring for 5 min, one drop of CH$_3$COOH was added and the reaction was stirred overnight at room temperature. The solvent was removed and the residue was purified by preparative thin layer chromatography to afford the title compound as a white solid (20 mg).

$^1$H NMR (300 MHz, CD$_3$OD): δ 0.89 (d, J=6.6 Hz, 3H), 1.03 (d, J=6.6 Hz, 3H), 1.89-1.96 (m, 1H), 2.08-2.11 (m, 1H), 2.68-2.73 (m, 2H), 2.91-2.94 (m, 1H), 4.04-4.07 (m, 2H), 4.19 (s, 2H), 7.17-7.24 (m, 7H), 7.57 (d, J=7.5 Hz, 2H).

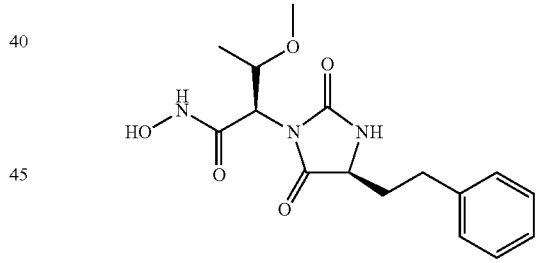

Example 42

2-(2,5-Dioxo-4-phenethyl-imidazolidin-1-yl)-N-hydroxy-3-methoxybutyramide (42)

The procedure described in method A was followed but using (R)-methyl 2-amino-3-methoxybutanoate instead of D-valine methyl ester hydrochloride which gave the title compound (6 mg).

$^1$H NMR (300 MHz, CDCl$_3$): δ 1.13 (d, J=6.3 Hz, 3H), 2.01-1.91 (m, 1H), 2.19-2.10 (m, 1H), 2.74-2.69 (m, 2H), 3.40 (s, 3H), 4.11-4.04 (m, 1H), 4.33-4.26 (m, 1H), 4.51-4.46 (m, 1H), 6.83 (s, 1H), 7.30-7.16 (m, 5H), 8.46-8.24 (m, 1H), 9.77 (s, 1H).

Example 43

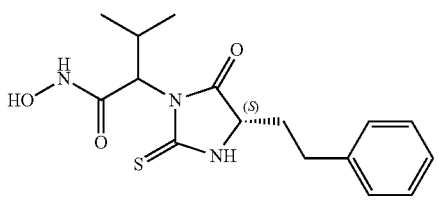

N-hydroxy-3-methyl-2-hydroxy-(5-oxo-4-phenethyl-2-thioxo-imidazolidin-1-yl)-butyramide Method H

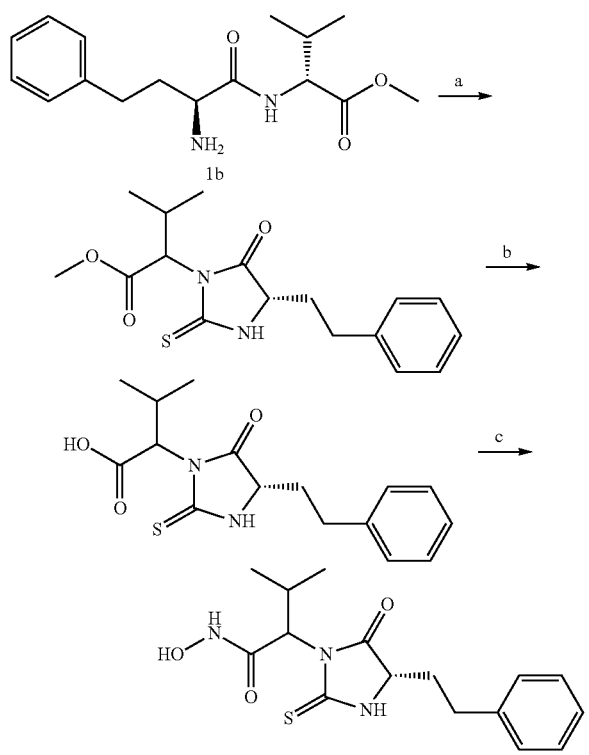

a) 1,1'–thiocarbonyldiimidazole, CH₂Cl₂; b) 6N HCl, dioxane/H₂O; c) BOP, NMM, NH₂OHHCl, DMF.

Step a

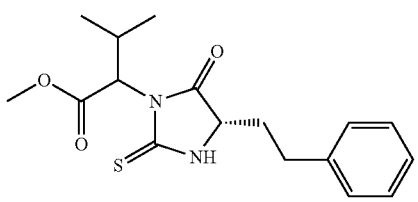

Under nitrogen, to a solution of 1b (440 mg, 1.50 mmol) in CH₂Cl₂ (15 mL) prepared according to Method A above, was added 1,1'-thiocarbonyldiimidazole (1.34 g, 7.52 mmol). The mixture was stirred at room temperature for 3 h and concentrated under reduced pressure. The residue was diluted with EtOAc and washed with brine. The putative diastereomers at the valine alpha carbon co-migrate under TLC and were confirmed by NMR below. The organic layer was dried and concentrated under reduced pressure. The residue was purified by silica gel column chromatography to afford the title compound as a pale yellow oil (200 mg, 40%).

$^1$H NMR (300 MHz, CDCl$_3$): δ 0.87, 0.88 (for two epimers, d, J=6.6 Hz, 3H), 1.20, 1.21 (for two epimers, d, J=6.6 Hz, 3H), 2.01-2.12 (m, 1H), 2.21-2.33 (m, 1H), 2.72-2.85 (m, 3H), 3.71 (s, 3H), 4.08-4.16 (m, 1H), 4.92, 4.94 (for two epimers, d, J=9.0 Hz, 1H), 7.19-7.36 (m, 5H).

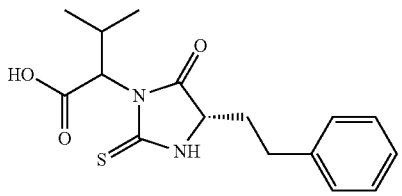

Step b

To a solution of the above obtained compound (200 mg, 0.6 mmol) in dioxane (2.5 mL) was added 10 mL of 6N HCl. The mixture was stirred at 90° C. for 2 days. The reaction solvent was removed under reduced pressure. The residue was purified by flash silica gel column chromatography to afford the title compound as a pale yellow oil (160 mg, 83%).

$^1$H NMR (300 MHz, CDCl$_3$): δ 0.88 (d, J=6.6 Hz, 3H), 1.21 (d, J=6.6 Hz, 3H), 1.94-2.06 (m, 1H), 2.16-2.30 (m, 1H), 2.57-2.88 (m, 3H), 4.04-4.14 (m, 1H), 4.99, 5.01 (for two epimers, d, J=9.3 Hz, 1H), 7.16-7.32 (m, 5H), 8.57 (d, J=10.8 Hz, 1H), 9.84 (s, br, 1H).

Step c

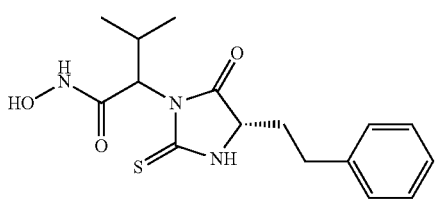

A solution of the above obtained compound (160 mg, 0.50 mmol) in DMF (5 mL) was added N-methylmorpholine (0.23 mL, 2.09 mmol). The mixture was cooled to 0 degrees and BOP (250 mg, 0.57 mmol) added. After stirring for 30 min at 0 degrees HONH₂×HCl (73 mg, 1.04 mmol) was added. The reaction was then allowed to warm to room temperature and stirred overnight. The reaction solvent was removed under reduced pressure. The residue was diluted with EtOAc, washed with 1N HCl, saturated NaHCO₃ and brine, dried over anhydrous Na₂SO₄, and concentrated under reduced pressure. The obtained residue was carefully purified by silica gel column chromatography to afford two epimers of the title compound both as a pale yellow oil (60+60 mg, 72%). Conventional preparative HPLC would allow purification of the diastereomers.

Less polar epimer: $^1$H NMR (300 MHz, CD$_3$OD): δ 0.88 (d, J=6.6 Hz, 3H), 1.07 (d, J=6.6 Hz, 3H), 1.95-2.17 (m, 2H), 2.61-2.76 (m, 2H), 3.06-3.14 (m, 1H), 4.16 (t, J=5.1 Hz, 1H), 4.79 (d, J=11.1 Hz, 1H), 7.15-7.30 (m, 5H).

More polar epimer: $^1$H NMR (300 MHz, CD$_3$OD): δ 0.88 (d, J=6.6 Hz, 3H), 1.07 (d, J=6.6 Hz, 3H), 1.91-2.18 (m, 2H), 2.65-2.77 (m, 2H), 3.01-3.11 (m, 1H), 4.10 (dd, J=5.1 Hz, 7.2 Hz, 1H), 4.89 (d, J=11.1 Hz, 1H), 7.16-7.32 (m, 5H).

Biological Examples

A typical MMP-12 enzyme assay employs recombinant human MMP-12 catalytic domain expressed and purified as described by Parkar A. A. et al, (2000), Protein Expression and Purification, 20:152. The purified enzyme can be used to monitor inhibitors of activity as follows: MMP-12 (50 ng/ml final concentration) is incubated for 60 minutes at room temperature with the synthetic substrate Mac-Pro-Cha-Gly-Nva-His-Ala-Dpa-NH$_2$ in assay buffer (0.1M "Tris-HCl" (trade mark) buffer, pH 7.3 containing O.1M NaCl, 20 mM CaCl$_2$, 0.020 mM ZnCl and 0.05% (w/v) "Brij 35" (trade mark) detergent) in the presence (5 concentrations) or absence of inhibitors. Activity is determined by measuring the fluorescence at λ$_{ex}$ 320 nm and λ$_{em}$ 405 nm. Percent inhibition is calculated as follows: % Inhibition is equal to the (Fluorescence$_{plus\ inhibitor}$–Fluorescence$_{background}$); divided by the (Fluorescence$_{minus\ inhibitor}$–Fluorescence$_{background}$);

A favoured assay employs full length recombinant human MMP-12, amino acid residues 1 to 470 (Shapiro et al 1993, J Biol Chem 268:23824-23829) expressed in mouse myeloma cell line NS-40. The purified rhMMP-12 typically has the N terminal sequence L$_{17}$PLNSSTSLE and an SDS-PAGE apparent molecular mass of approx. 56 kDa. Such proteins are available from R&D Systems, USA as a lyophilised 0.2 um filtered solution of 25 mM MES, 0.15M NaCl, 10 mMCaCl$_2$, 0.15% Brij 35, pH 5.5. Auto-activation of the rhMMP-12 can be achieved by dilution to 0.05 mg/ml into TCNB buffer (50 mMTris, 10 mM CaCl$_2$, 0.15M NaCl, 0.05% Brij 35, pH 7) and incubation at 37 degrees for 30 hours. A preferred buffer for MMP work is 50 mM Tris.HCl, pH 7.5, 200 mM Ca acetate.

Suitable FRET substrates include (7-methoxycoumarin-4-yl)acetyl-Pro-Leu-Gly-Leu-(3-(2,4-dinitrophenoyl)-L-2,3-diaminopropionyl)-Ala-Arg-NH$_2$, commercially available from R&D Systems, USA. Typical specific activities are >500 picomol/min/ug, with rhMMP-12 measured with 10 uM of this substrate, 20 ng activated enzyme in 100 ul TCNB buffer at room temperature.

An alternative general MMP substrate is Dnp-PLGLWA$_D$-R-NH$_2$.

Counterscreening for MMP selectivity is carried out analogously to the above using commercially available recombinant enzymes (R& D Systems USA) such as MMP-1, 2 & 9 (same substrate as MMP-12) or 3 & 10 (substrate: Mca-RPKPVE-Nva-WRK(Dnp)-AR-NH$_2$).

For example, Table 1 shows the Ki-value expressed in nM for a representative selection of compounds according to the invention when tested in an MMP-12 enzyme assay such as those described above. Category A indicates ≦50 nM inhibition, category B indicates 51-200 nM inhibition and category C indicates >200 nM:

| Example No. | Ki |
| --- | --- |
| 7 | B |
| 10 | A |
| 14 | A |
| 15 | B |
| 25h | C |
| 26 | A |
| 28 | A |
| 29 | A |
| 30 | A |
| 31 | A |
| 33 | A |
| 34 | A |
| 36 | A |
| 37 | A |
| 38 | A |
| 39 | A |
| 40 | A |

Selectivity Profiles

To evaluate the enzymatic inhibition of Tumour Necrosis Factor-α Converting Enzyme (TACE) exhibited by the compounds, an assay wherein a FRET substrate was utilized to generate a spectroscopic response to peptidase cleavage. The activity was measured by a continuous detection of increased fluorescence intensity during 12 min. The substrate consisted of a peptide with a fluorescent donor 7-methoxycoumarin (Mca) and a quenching acceptor 2,4-dinitrophenyl group (Dpa), typically Mca-P-L-A-Q-A-V-Dpa-R-S-S-S-R-NH$_2$ (R&D Systems, ES003). The cleavage site by TACE is the peptide bond between Ala and Val. The compounds were tested at a range of concentrations while the enzyme and substrate concentrations were fixed. A typical TACE assay employs recombinant human TACE (supplied by R&D Systems) in an assay buffer (25 mM Tris-HCl, pH=9.0, 2.5 μM ZnCl$_2$, 0.005% Brij 35). The enzyme concentration (TACE) used was 100 ng/ml, the substrate was prepared at a 100 μM stock solution in DMSO and a 96-well polypropylene plate was used for the reaction mixtures. To each well of the plate was added assay buffer 90.0 μl, enzyme (TACE) 0.09 μl and inhibitor 1 μl. The reactions were started by addition of substrate 10 μl/well, giving a substrate concentration of 10 μM and a total volume of 100 μl/well. The total concentration of DMSO was not above 1%. The assay was performed at ambient temperature. Product fluorescence (emission filter 320 nM, excitation filter 405 nM) was monitored with a Thermo Labsystems Fluoroskan Ascent plate reader. The Ki was determined by Prism Software.

To evaluate the enzymatic inhibition of Human Matrix Metalloproteinase (MMP-3) exhibited by the compounds, an assay wherein FRET was utilized to generate a spectroscopic response to peptidase cleavage, was used. The activity was measured by a continuous detection of increased fluorescence intensity during 12 min. The substrate consisted of a peptide with a fluorescent donor 7-methoxycoumarin (Mca) and a quenching acceptor 2,4-dinitrophenyl group (Dpa), typically Mca-Arg-Pro-Lys-Pro-Val-Glu-Nval-Trp-Arg-Lys(Dnp)-NH$_2$ (R&D Systems, ES002). The cleavage site by MMP-3 is the peptide bond between Glu and Nval. The compounds were tested at a range of concentrations, the enzyme concentration (MMP-3) was fixed at 400 ng/ml and the substrate concentrations was 10 μM. The MMP-3 assay used employs recombinant human MMP-3 (supplied by R&D Systems) in an assay buffer of 50 mM Tris-HCl, 200 mM calcium acetate at pH=7.5. The MMP-3 enzyme was preactivated by dilution to 0.119 mg/ml into 1 mM APMA (p-aminophenylmercuric acetate) followed by incubation at 37° C. for 24 hours. The substrate was prepared at a 100 μM stock solution in DMSO and a 96-well polypropylene plate was used for the reaction mixtures. To each well of the plate was added assay buffer 90.0 μl, enzyme (MMP-3) 0.3 μl and inhibitor 1 μl. The reactions were started by addition of substrate, 10 μl/well, to a total volume of 100 μl/well. The total concentration of DMSO was not above 1%. The assay was performed at ambient temperature. Product fluorescence (emission filter 320 nM, excitation filter 405 nM) was monitored with a Thermo Labsystems Fluoroskan Ascent plate reader. The Ki was determined by Prism Software.

The selectivity for MMP-12 over MMP-3 and TACE was evaluated for a representative selection of the compounds of the invention by comparing the Ki figures obtained when tested in the corresponding enzyme assays, such as those described above. The selectivity is presented as the fold difference in Ki for TACE and MMP-3 compared to MMP-12 and is calculated as the ratio $Ki_{(TACE)}/Ki_{MMP-12}$ and $Ki_{(MMP-3)}/Ki_{MMP-12}$ respectively. The result is summarized in Table 2.

| Example | $Ki_{(TACE)}/Ki_{(MMP-12)}$ | $Ki_{(MMP-3)}/Ki_{(MMP-12)}$ |
|---|---|---|
| 1 | 380 | 140 |
| 5 | >4500 | 71 |
| 7 | >80 | 53 |
| 10 | >150 | 34 |
| 12 | 245 | 122 |
| 13i | >190 | >190 |
| 14 | >500 | >500 |
| 15 | >700 | 120 |
| 30 | 2200 | 75 |
| 32 | 140 | >200 |
| 36 | 280 | 240 |
| 38 | 390 | 150 |

The invention claimed is:

1. A compound of the formula:

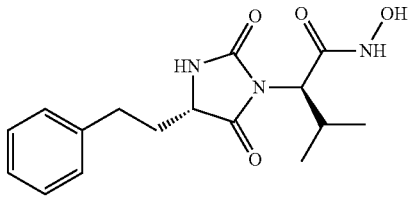

or a pharmaceutically acceptable salt thereof.

2. A compound according to claim 1 wherein the salt is a an acid addition salt selected from hydrochloride, hydrobromide, citrate, tosylate, maleate, a salt formed with tartaric acid or a salt formed with sulphuric acid.

3. A compound according to claim 1, wherein the salt is an alkali metal salt selected from sodium or potassium, an alkaline earth metal salt selected from calcium and magnesium or a triethylamine salt.

4. A compound of the formula:

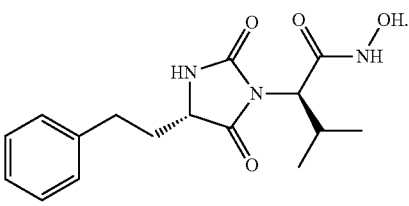

5. A pharmaceutical composition comprising a compound according to claim 1, or a pharmaceutically acceptable salt thereof, and a pharmaceutically acceptable adjuvant, diluent or carrier.

6. A method for the treatment of a disease or condition mediated by MMP-12 selected from the group consisting of asthma and chronic obstructive pulmonary disease, the method comprising the administration of an effective amount of a compound according to claim 1, or a pharmaceutically acceptable salt thereof, to a patient in need thereof.

7. A method according to claim 6 wherein the disease is chronic obstructive pulmonary disease.

8. A method according to claim 7, wherein the compound or pharmaceutically acceptable salt thereof is administered by the inhaled route.

9. A method according to claim 7, wherein the compound or pharmaceutically acceptable salt thereof is administered by the oral delivery route as a capsule or tablet.

* * * * *